United States Patent
Muehlebach et al.

(10) Patent No.: US 9,988,366 B2
(45) Date of Patent: Jun. 5, 2018

(54) PESTICIDALLY ACTIVE HETEROCYCLIC DERIVATIVES WITH SULPHUR CONTAINING SUBSTITUENTS

(71) Applicant: Syngenta Participations AG, Basel (CH)

(72) Inventors: Michel Muehlebach, Stein (CH); Ruud Titulaer, Nijmegen (NL); Daniel Emery, Basel (CH); Andrew Edmunds, Stein (CH); Andre Stoller, Stein (CH); Pierre Joseph Marcel Jung, Stein (CH); Anke Buchholz, Stein (CH); Peter Renold, Stein (CH)

(73) Assignee: Syngenta Participations AG, Basel (CH)

( * ) Notice: Subject to any disclaimer, the term of this patent is extended or adjusted under 35 U.S.C. 154(b) by 0 days. days.

(21) Appl. No.: 15/129,460

(22) PCT Filed: Mar. 27, 2015

(86) PCT No.: PCT/EP2015/056747
§ 371 (c)(1),
(2) Date: Sep. 27, 2016

(87) PCT Pub. No.: WO2015/144895
PCT Pub. Date: Oct. 1, 2015

(65) Prior Publication Data
US 2017/0107201 A1 Apr. 20, 2017

(30) Foreign Application Priority Data

Mar. 28, 2014 (EP) .................. 14162290

(51) Int. Cl.
| | |
|---|---|
| *C07D 233/54* | (2006.01) |
| *C07D 233/64* | (2006.01) |
| *C07D 401/04* | (2006.01) |
| *C07D 401/14* | (2006.01) |
| *A01N 43/50* | (2006.01) |
| *A01N 43/54* | (2006.01) |
| *A01N 43/58* | (2006.01) |
| *A01N 43/60* | (2006.01) |
| *A01N 43/88* | (2006.01) |
| *A01N 47/02* | (2006.01) |

(52) U.S. Cl.
CPC .......... *C07D 401/14* (2013.01); *A01N 43/50* (2013.01); *A01N 43/54* (2013.01); *A01N 43/58* (2013.01); *A01N 43/60* (2013.01); *A01N 43/88* (2013.01); *A01N 47/02* (2013.01); *C07D 233/54* (2013.01); *C07D 233/64* (2013.01); *C07D 401/04* (2013.01)

(58) Field of Classification Search
CPC .. C07D 401/04; C07D 401/14; C07D 233/54; C07D 233/61; A01N 43/50; A01N 43/54; A01N 43/58; A01N 43/60; A01N 43/88; A01N 47/02
See application file for complete search history.

(56) References Cited

U.S. PATENT DOCUMENTS 4,822,805 A * 4/1989 Takasugi .............. C07D 401/04
514/341

FOREIGN PATENT DOCUMENTS

| DE | 4343613 A1 | 6/1995 |
| EP | 0712847 A1 | 5/1996 |
| WO | 2012084678 A1 | 6/2012 |

OTHER PUBLICATIONS

Tanaka, Akito et al.: "Studies on Antiplatelet Agents. I. Synthesis and Platelet Inhibitory Activity of 5-Alkyl-2-aryl-4-pyridylimidazoles" in: Chem. Pharm. Bull. 40(12) 3206-3213 (1992).
International Search Report for PCT/EP2015/056747, dated Jun. 2, 2015.
Demuth, Thomas P. et al.: "Heteroatomfacilitated ortho directed lithiatns of 2-arylimidazoles" in: Journal of Organic Chemistry 57/10, 1992, pp. 2963-2965. XP002739950.
Extended European Search Report for EP14162290.2, dated Sep. 30, 2014.

* cited by examiner

*Primary Examiner* — John Pak
*Assistant Examiner* — Nathan W Schlientz
(74) *Attorney, Agent, or Firm* — James Cueva

(57) ABSTRACT

Compounds of formula (I), wherein the substituents are as defined in claim 1, and the agrochemically acceptable salts, stereoismers, enantiomers, tautomers and N-oxides of those compounds, can be used as insecticides and can be prepared in a manner known per se.

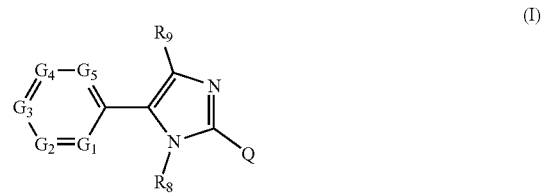

(I)

15 Claims, No Drawings

PESTICIDALLY ACTIVE HETEROCYCLIC DERIVATIVES WITH SULPHUR CONTAINING SUBSTITUENTS

RELATED APPLICATION INFORMATION

This application is a 371 of International Application No. PCT/EP2015/056747, filed 27 Mar. 2015, which claims priority to EP 14162290.2, filed 28 Mar. 2014, the contents of which are incorporated herein by reference herein.

The present invention relates to insecticidally active heterocyclic derivatives containing sulphur substituents, to processes for their preparation, to compositions comprising those compounds, and to their use for controlling animal pests (including arthropods and in particular insects or representatives of the order Acarina).

Heterocyclic compounds with pesticidal action are known and described, for example, in WO 2010/125985 and WO 2013/018928.

There have now been found novel pesticidally active heterocyclic imidazole derivatives with sulphur containing phenyl- and pyridyl substituents.

The present invention accordingly relates to compounds of formula I,

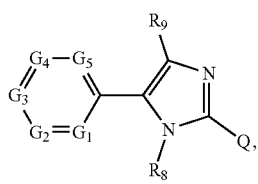

(I)

wherein
$G_1$ is nitrogen or $CR_2$;
$G_2$ is nitrogen or $CR_3$;
$G_3$ is nitrogen or $CR_4$;
$G_4$ is nitrogen or $CR_5$;
$G_5$ is nitrogen or $CR_6$, with the proviso that not more than 2 nitrogens as G may follow consecutively;
$R_2$, $R_3$, $R_4$, $R_5$ or $R_6$ are, independently from each other, hydrogen, halogen, $C_1$-$C_4$haloalkyl, $C_1$-$C_4$haloalkyl substituted by one or two hydroxy, $C_1$-$C_4$haloalkyl substituted by one or two methoxy, $C_1$-$C_4$haloalkyl substituted by one or two cyano; or
$R_2$, $R_3$, $R_4$, $R_5$ or $R_6$ are independently from each other, $C_1$-$C_4$haloalkylthio, $C_1$-$C_4$haloalkylsulfinyl, $C_1$-$C_4$haloalkylsulfonyl, O($C_1$-$C_4$haloalkyl), $SF_5$, phenylcarbonylthio, cyano, mercapto, $C_1$-$C_4$alkoxycarbonyl, $C_1$-$C_4$alkylcarbonyl or —C(O)$C_1$-$C_4$haloalkyl; or
two adjacent $R_i$, wherein $R_i$ is selected from $R_2$, $R_3$, $R_4$, $R_5$ and $R_6$, taken together may form a fragment —OCH$_2$O— or —OCF$_2$O—;
Q is a radical selected from the group consisting of formula $Q_1$ and $Q_2$

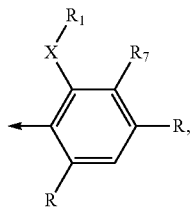

$Q_1$

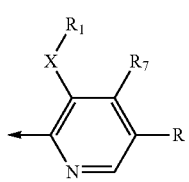

$Q_2$ wherein the arrow denotes the point of attachment to the imidazole ring;
and wherein X is S, SO or $SO_2$;
each R is, independently from each other, hydrogen, halogen, $C_1$-$C_4$haloalkoxy or $C_1$-$C_4$haloalkyl;
each $R_1$ is, independently from each other, $C_1$-$C_4$alkyl, $C_1$-$C_4$haloalkyl, $C_3$-$C_6$cycloalkyl, $C_3$-$C_6$cycloalkyl-$C_1$-$C_4$alkyl, $C_3$-$C_6$halocycloalkyl, $C_2$-$C_6$alkenyl, $C_2$-$C_6$haloalkenyl or $C_2$-$C_6$alkynyl;
each $R_7$ is, independently from each other, hydrogen or halogen;
$R_8$ is hydrogen, $C_1$-$C_4$alkyl or $C_1$-$C_4$haloalkyl; and
$R_9$ is hydrogen, $C_1$-$C_4$alkyl, $C_1$-$C_4$haloalkyl or halogen;
and agrochemically acceptable salts, stereoismers, enantiomers, tautomers and N-oxides of those compounds; with the exception of the compound 2-[5-methyl-4-(3-pyridyl)-1H-imidazol-2-yl]-3-methylsulfanyl-pyridine.

Compounds of formula I which have at least one basic centre can form, for example, acid addition salts, for example with strong inorganic acids such as mineral acids, for example perchloric acid, sulfuric acid, nitric acid, nitrose acid, a phosphorus acid or a hydrohalic acid, with strong organic carboxylic acids, such as $C_1$-$C_4$alkanecarboxylic acids which are unsubstituted or substituted, for example by halogen, for example acetic acid, such as saturated or unsaturated dicarboxylic acids, for example oxalic acid, malonic acid, succinic acid, maleic acid, fumaric acid or phthalic acid, such as hydroxycarboxylic acids, for example ascorbic acid, lactic acid, malic acid, tartaric acid or citric acid, or such as benzoic acid, or with organic sulfonic acids, such as $C_1$-$C_4$alkane- or arylsulfonic acids which are unsubstituted or substituted, for example by halogen, for example methane- or p-toluenesulfonic acid. Compounds of formula I which have at least one acidic group can form, for example, salts with bases, for example mineral salts such as alkali metal or alkaline earth metal salts, for example sodium, potassium or magnesium salts, or salts with ammonia or an organic amine, such as morpholine, piperidine, pyrrolidine, a mono-, di- or tri-lower-alkylamine, for example ethyl-, diethyl-, triethyl- or dimethylpropylamine, or a mono-, di- or trihydroxy-lower-alkylamine, for example mono-, di- or triethanolamine.

The alkyl groups occurring in the definitions of the substituents can be straight-chain or branched and are, for example, methyl, ethyl, n-propyl, isopropyl, n-butyl, sec-butyl, iso-butyl, tert-butyl, pentyl, hexyl, nonyl, decyl and their branched isomers. Alkoxy, alkenyl and alkynyl radicals are derived from the alkyl radicals mentioned. The alkenyl and alkynyl groups can be mono- or polyunsaturated.

Halogen is generally fluorine, chlorine, bromine or iodine. This also applies, correspondingly, to halogen in combination with other meanings, such as haloalkyl or halophenyl.

Haloalkyl groups preferably have a chain length of from 1 to 6 carbon atoms. Haloalkyl is, for example, fluoromethyl, difluoromethyl, trifluoromethyl, chloromethyl, dichloromethyl, trichloromethyl, 2,2,2-trifluoroethyl, 2-fluoroethyl, 2-chloroethyl, pentafluoroethyl, 1,1-difluoro-2,2,2-trichloroethyl, 2,2,3,3-tetrafluoroethyl and 2,2,2-trichloroethyl; preferably trichloromethyl, difluorochloromethyl, difluoromethyl, trifluoromethyl and dichlorofluoromethyl.

Alkoxy groups preferably have a preferred chain length of from 1 to 6 carbon atoms. Alkoxy is, for example, methoxy, ethoxy, propoxy, i-propoxy, n-butoxy, isobutoxy, sec-butoxy and tert-butoxy and also the isomeric pentyloxy and hexyloxy radicals; preferably methoxy and ethoxy.

Alkoxyalkyl groups preferably have a chain length of 1 to 6 carbon atoms.

Alkoxyalkyl is, for example, methoxymethyl, methoxyethyl, ethoxymethyl, ethoxyethyl, n-propoxymethyl, n-propoxyethyl, isopropoxymethyl or isopropoxyethyl.

The cycloalkyl groups preferably have from 3 to 6 ring carbon atoms, for example cyclopropyl, cyclobutyl, cyclopentyl and cyclohexyl.

According to the present invention, $O(C_1-C_4haloalkyl)$ is equivalent to $C_1-C_4haloalkoxy$. Haloalkoxy groups preferably have a chain length of from 1 to 4 carbon atoms. Haloalkoxy is, for example, difluoromethoxy, trifluoromethoxy or 2,2,2-trifluoroethoxy.

According to the present invention, $C_1-C_4haloalkylthio$ is equivalent to $C_1-C_4haloalkylsulfanyl$. Haloalkylsulfanyl groups preferably have a chain length of from 1 to 4 carbon atoms. Haloalkylsulfanyl is, for example, difluoromethylsulfanyl, trifluoromethylsulfanyl or 2,2,2-trifluoroethylsulfanyl. Similar considerations apply to the radicals $C_1-C_4haloalkylsulfinyl$ and $C_1-C_4haloalkylsulfonyl$, which may be, for example, trifluoromethylsulfinyl, trifluoromethylsulfonyl or 2,2,2-trifluoroethylsulfonyl.

According to the present invention, when two adjacent $R_i$, wherein $R_i$ is selected from $R_2$, $R_3$, $R_4$, $R_5$ and $R_6$, taken together form a fragment —$OCH_2O$— or —$OCF_2O$— then an additional five-membered dioxolane or difluoro-dioxolane ring is formed. For example, compounds of the formula I, wherein $G_2$ is $CR_3$, $G_3$ is $CR_4$, and in which $R_3$ and $R_4$ taken together form the fragment —$OCF_2O$—, will have the following structure:

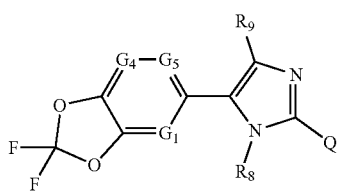

According to the present invention, when two groups G are nitrogen then the radical consisting of $G_1$ to $G_5$ together with the carbon atom to which $G_1$ and $G_5$ are attached form a diazine ring. The diazine ring may be selected from the group consisting of pyrimidinyl, pyrazinyl and pyridazinyl.

In a preferred embodiment of the invention,
$R_2$, $R_3$, $R_4$, $R_5$ or $R_6$ are, independently from each other, hydrogen, halogen, $C_1-C_4haloalkyl$, $C_1-C_4haloalkyl$ substituted by one or two hydroxy, $C_1-C_4haloalkyl$ substituted by one or two methoxy; or
$R_2$, $R_3$, $R_4$, $R_5$ or $R_6$ are independently from each other, $C_1-C_4haloalkylthio$, $C_1-C_4haloalkylsulfonyl$, $O(C_1-C_4haloalkyl)$, $SF_5$, phenylcarbonylthio, cyano, mercapto, or $C_1-C_4alkoxycarbonyl$;

each R is, independently from each other, hydrogen, halogen or $C_1-C_4haloalkyl$; and
each $R_1$ is, independently from each other, $C_1-C_4alkyl$, $C_1-C_4haloalkyl$, $C_3-C_6cycloalkyl$, $C_3-C_6cycloalkyl-C_1-C_4alkyl$, $C_3-C_6halocycloalkyl$, $C_2-C_6alkenyl$, $C_2-C_6haloalkenyl$ or $C_2-C_6alkynyl$.

A preferred group of compounds of formula I is represented by the compounds of formula I-1

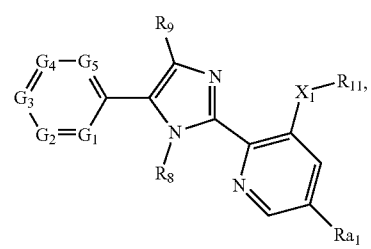

wherein $G_1$, $G_2$, $G_3$, $G_4$, and $G_5$ are as defined under formula I above; and wherein $X_1$ is S, SO or $SO_2$;
$Ra_1$ is hydrogen, halogen or $C_1-C_4haloalkyl$; and $R_{11}$ is methyl, ethyl, n-propyl,
i-propyl or cyclopropylmethyl; $R_8$ is as defined above under formula I, preferably methyl, $R_9$ is as defined above under formula I, preferably hydrogen, and agrochemically acceptable salts, stereoismers, enantiomers, tautomers and N-oxides of those compounds.

Also preferred are compounds of formula I-1 with $G_1$ defined as N, $G_2$ defined as $C(CF_3)$, and $G_3$, $G_4$ and $G_5$ defined as CH.

Yet other preferred compounds of formula I-1 have $G_1$ defined as N, $G_3$ defined as $C(CF_3)$, and $G_2$, $G_4$ and $G_5$ defined as CH.

Further preferred compounds of formula I-1 have $G_1$ defined as N, $G_4$ defined as $C(CF_3)$, and $G_2$, $G_3$ and $G_5$ defined as CH.

Other preferred compounds of formula I-1 have $G_1$, $G_4$ and $G_5$ defined as CH, $G_2$ defined as N and $G_3$ defined as $C(CF_3)$.

Also preferred are compounds of formula I-1 with $G_1$, $G_3$ and $G_5$ defined as CH, $G_2$ defined as N and $G_4$ defined as $C(CF_3)$.

Yet other preferred compounds of formula I-1 have $G_1$, $G_4$ and $G_5$ defined as CH, $G_3$ defined as N and $G_2$ defined as $C(CF_3)$.

Another group of preferred compounds of formula I-1 have $G_1$ and $G_3$ defined as N, $G_4$ and $G_5$ defined as CH, and $G_2$ defined as $C(CF_3)$.

Other preferred compounds of formula I-1 have $G_1$ and $G_4$ defined as N, $G_2$ and $G_5$ defined as CH, and $G_3$ defined as $C(CF_3)$.

Also preferred are compounds of formula I-1 with $G_1$ and $G_4$ defined as N, $G_3$ and $G_5$ defined as CH, and $G_2$ defined as $C(CF_3)$.

Yet other preferred compounds of formula I-1 have $G_1$ and $G_5$ defined as N, $G_2$ and $G_4$ defined as CH, and $G_3$ defined as $C(CF_3)$.

Further preferred compounds of formula I-1 have $G_1$ and $G_5$ defined as N, $G_3$ and $G_4$ defined as CH, and $G_2$ defined as $C(CF_3)$.

Other preferred compounds of formula I-1 have $G_2$ and $G_4$ defined as N, $G_1$ and $G_5$ defined as CH, and $G_3$ defined as $C(CF_3)$.

Also preferred are compounds of formula I-1 with $G_1$ and $G_2$ defined as N, $G_4$ and $G_5$ defined as CH, and $G_3$ defined as $C(CF_3)$.

Yet other preferred compounds of formula I-1 have $G_1$ and $G_2$ defined as N, $G_3$ and $G_5$ defined as CH, and $G_4$ defined as $C(CF_3)$.

In further preferred compounds of formula I-1, $G_1$ and $G_3$ are N, $G_2$ and $G_5$ are CH, and $G_4$ is $C(CF_3)$.

In an especially preferred group of compounds of formula I-1, $G_1$ is N, $G_2$ is CH or C(halogen), $G_3$ is CH, $G_4$ is $C(CF_3)$ and $G_5$ is CH.

In an especially preferred group of compounds of formula I-1, $G_1$ is CH, $G_2$ is N, $G_3$ is CH, $G_4$ is $C(CF_3)$ or C(CN) and $G_5$ is CH.

In an especially preferred group of compounds of formula I-1, $G_1$ is CH, $G_2$ is N, $G_3$ is $C(CF_3)$, C(halogen) or C(CN), $G_4$ is CH and $G_5$ is CH.

In an especially preferred group of compounds of formula I-1, $G_1$ is CH, $G_2$ is CH, $G_3$ is N, $G_4$ is $C(CF_3)$ or C(halogen) and $G_5$ is CH.

In an especially preferred group of compounds of formula I-1, $G_1$ is N, $G_2$ is CH, $G_3$ is C(CN), $G_4$ is CH and $G_5$ is CH.

In an especially preferred group of compounds of formula I-1, $G_1$ is N, $G_2$ is $C(CF_3)$ or C(CN), $G_3$ is CH, $G_4$ is CH and $G_5$ is CH.

In an especially preferred group of compounds of formula I-1, $G_1$ is CH, $G_2$ is N, $G_3$ is CH, $G_4$ is CH and $G_5$ is $C(CF_3)$.

In an especially preferred group of compounds of formula I-1, $G_1$ is CH, $G_2$ is CH, $G_3$ is $C(CF_3)$, $C(OCF_3)$, C(CN), $C(C(O)CH_3)$, $C(SCF_3)$, $C(SO_2CF_3)$ or C(halogen), $G_4$ is CH and $G_5$ is CH.

In an especially preferred group of compounds of formula I-1, $G_1$ is CH, $G_2$ is $C(CF_3)$, $C(OCF_3)$, C(CN), $C(C(O)CH_3)$, $C(SCF_3)$, $C(SO_2CF_3)$ or C(halogen), $G_3$ is CH, $G_4$ is CH and $G_5$ is CH. In said especially preferred group of compounds of formula I-1, $R_8$ is preferably methyl and $R_9$ is preferably hydrogen.

Another preferred group of compounds of formula I is represented by the compounds of formula I-2

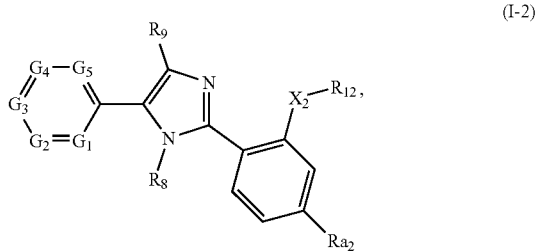

wherein $G_1$, $G_2$, $G_3$, $G_4$, and $G_5$ are as defined under formula I above; and wherein $X_2$ is S, SO or $SO_2$; $Ra_2$ is hydrogen, halogen or $C_1$-$C_4$haloalkyl; and $R_{12}$ is methyl, ethyl, n-propyl, i-propyl or cyclopropylmethyl; $R_8$ is as defined above under formula I, preferably methyl, $R_9$ is as defined above under formula I, preferably hydrogen, and agrochemically acceptable salts, stereoismers, enantiomers, tautomers and N-oxides of those compounds.

Also preferred are compounds of formula I-2 with $G_1$ defined as N, $G_2$ defined as $C(CF_3)$, and $G_3$, $G_4$ and $G_5$ defined as CH.

Yet other preferred compounds of formula I-2 have $G_1$ defined as N, $G_3$ defined as $C(CF_3)$, and $G_2$, $G_4$ and $G_5$ defined as CH.

Further preferred compounds of formula I-2 have $G_1$ defined as N, $G_4$ defined as $C(CF_3)$, and $G_2$, $G_3$ and $G_5$ defined as CH.

Other preferred compounds of formula I-2 have $G_1$, $G_4$ and $G_5$ defined as CH, $G_2$ defined as N and $G_3$ defined as $C(CF_3)$.

Also preferred are compounds of formula I-2 with $G_1$, $G_3$ and $G_5$ defined as CH, $G_2$ defined as N and $G_4$ defined as $C(CF_3)$.

Yet other preferred compounds of formula I-2 have $G_1$, $G_4$ and $G_5$ defined as CH, $G_3$ defined as N and $G_2$ defined as $C(CF_3)$.

Another group of preferred compounds of formula I-2 have $G_1$ and $G_3$ defined as N, $G_4$ and $G_5$ defined as CH, and $G_2$ defined as $C(CF_3)$.

Other preferred compounds of formula I-2 have $G_1$ and $G_4$ defined as N, $G_2$ and $G_5$ defined as CH, and $G_3$ defined as $C(CF_3)$.

Also preferred are compounds of formula I-2 with $G_1$ and $G_4$ defined as N, $G_3$ and $G_5$ defined as CH, and $G_2$ defined as $C(CF_3)$.

Yet other preferred compounds of formula I-2 have $G_1$ and $G_5$ defined as N, $G_2$ and $G_4$ defined as CH, and $G_3$ defined as $C(CF_3)$.

Further preferred compounds of formula I-2 have $G_1$ and $G_5$ defined as N, $G_3$ and $G_4$ defined as CH, and $G_2$ defined as $C(CF_3)$.

Other preferred compounds of formula I-2 have $G_2$ and $G_4$ defined as N, $G_1$ and $G_5$ defined as CH, and $G_3$ defined as $C(CF_3)$.

Also preferred are compounds of formula I-2 with $G_1$ and $G_2$ defined as N, $G_4$ and $G_5$ defined as CH, and $G_3$ defined as $C(CF_3)$.

Yet other preferred compounds of formula I-2 have $G_1$ and $G_2$ defined as N, $G_3$ and $G_5$ defined as CH, and $G_4$ defined as $C(CF_3)$.

In further preferred compounds of formula I-2, $G_1$ and $G_3$ are N, $G_2$ and $G_5$ are CH, and $G_4$ is $C(CF_3)$.

In an especially preferred group of compounds of formula I-1, $G_1$ is N, $G_2$ is CH or C(halogen), $G_3$ is CH, $G_4$ is $C(CF_3)$ and $G_5$ is CH.

In an especially preferred group of compounds of formula I-1, $G_1$ is CH, $G_2$ is N, $G_3$ is CH, $G_4$ is $C(CF_3)$ or C(CN) and $G_5$ is CH.

In an especially preferred group of compounds of formula I-1, $G_1$ is CH, $G_2$ is N, $G_3$ is $C(CF_3)$, C(halogen) or C(CN), $G_4$ is CH and $G_5$ is CH.

In an especially preferred group of compounds of formula I-1, $G_1$ is CH, $G_2$ is CH, $G_3$ is N, $G_4$ is $C(CF_3)$ or C(halogen) and $G_5$ is CH.

In an especially preferred group of compounds of formula I-1, $G_1$ is N, $G_2$ is CH, $G_3$ is C(CN), $G_4$ is CH and $G_5$ is CH.

In an especially preferred group of compounds of formula I-1, $G_1$ is N, $G_2$ is $C(CF_3)$ or C(CN), $G_3$ is CH, $G_4$ is CH and $G_5$ is CH.

In an especially preferred group of compounds of formula I-1, $G_1$ is CH, $G_2$ is N, $G_3$ is CH, $G_4$ is CH and $G_5$ is $C(CF_3)$.

In an especially preferred group of compounds of formula I-1, $G_1$ is CH, $G_2$ is CH, $G_3$ is $C(CF_3)$, $C(OCF_3)$, C(CN), $C(C(O)CH_3)$, $C(SCF_3)$, $C(SO_2CF_3)$ or C(halogen), $G_4$ is CH and $G_5$ is CH.

In an especially preferred group of compounds of formula I-1, $G_1$ is CH, $G_2$ is $C(CF_3)$, $C(OCF_3)$, C(CN), $C(C(O)CH_3)$, $C(SCF_3)$, $C(SO_2CF_3)$ or C(halogen), $G_3$ is CH, $G_4$ is CH and $G_5$ is CH. In said especially preferred group of compounds of formula I-1, $R_8$ is preferably methyl and $R_9$ is preferably hydrogen.

A further preferred embodiment of the invention comprises compounds of formula I represented by the compounds of formula I-3

(I-3)

wherein
A is N or CH;
$R_{10}$ is phenyl mono- or polysubstituted by substituents independently selected from the group consisting of halogen, cyano, $C_1$-$C_4$haloalkoxy, $C_1$-$C_4$haloalkyl and $C_1$-$C_4$alkylcarbonyl; or
$R_{10}$ is phenyl monosubstituted by substituents independently selected from the group consisting of $C_1$-$C_4$haloalkylsulfanyl, $C_1$-$C_4$haloalkylsulfinyl and $C_1$-$C_4$haloalkylsulfonyl, in particular trifluoromethylsulfanyl, trifluoromethylsulfinyl and trifluoromethylsulfonyl; or
$R_{10}$ is phenyl substituted by a fragment —$OCF_2O$— on two adjacent positions; or
$R_{10}$ is pyridyl mono- or polysubstituted by substituents independently selected from the group consisting of halogen, cyano, $C_1$-$C_4$haloalkoxy, $C_1$-$C_4$haloalkyl and $C_1$-$C_4$alkylcarbonyl; or
$R_{10}$ is pyridyl monosubstituted by substituents independently selected from the group consisting of $C_1$-$C_4$haloalkylsulfanyl, $C_1$-$C_4$haloalkylsulfinyl and $C_1$-$C_4$haloalkylsulfonyl, in particular trifluoromethylsulfanyl, trifluoromethylsulfinyl and trifluoromethylsulfonyl; or
$R_{10}$ is pyridyl substituted by a fragment —$OCF_2O$— on two adjacent positions;
$X_3$ is S, SO or $SO_2$, in particular S or $SO_2$;
$Ra_3$ is hydrogen or $C_1$-$C_4$haloalkyl, in particular trifluoromethyl;
$R_{13}$ is $C_1$-$C_4$alkyl, in particular methyl or ethyl;
$R_8$ is hydrogen or $C_1$-$C_4$alkyl, in particular methyl or ethyl;
$R_9$ is hydrogen, $C_1$-$C_4$alkyl or halogen, in particular hydrogen, chlorine or methyl;
and agrochemically acceptable salts, stereoisomers, enantiomers, tautomers and N-oxides of the compounds of formula I-3.

In said preferred embodiment comprising compounds of formula I-3, $R_{10}$ is preferably phenyl or pyridyl monosubstituted by substituents independently selected from the group consisting of halogen, cyano, $C_1$-$C_4$haloalkoxy, $C_1$-$C_4$haloalkyl, $C_1$-$C_4$alkylcarbonyl, $C_1$-$C_4$haloalkylsulfanyl, $C_1$-$C_4$haloalkylsulfinyl and $C_1$-$C_4$haloalkylsulfonyl. Especially preferred $R_{10}$ is selected from fluorine, chlorine, cyano, difluoromethoxy, trifluoromethoxy, trifluoromethyl, pentafluoroethyl, trifluoromethylsulfanyl, trifluoromethylsulfinyl and trifluoromethylsulfonyl.

A further preferred embodiment of the invention comprises compounds of formula I represented by the compounds of formula I-4

(I-4)

wherein
A is N or CH;
$R_{10}'$ is a diazine radical selected from the group consisting of formula DA1 to DA5,

DA1

DA2

DA3

DA4

DA5 wherein the arrow denotes the point of attachment to the triazole ring, and said group $R_{10}'$ can be mono- or polysubstituted by substituents independently selected from the group consisting of halogen, cyano, $C_1$-$C_4$haloalkoxy and $C_1$-$C_4$haloalkyl;
$X_4$ is S, SO or $SO_2$, in particular S or $SO_2$;
$Ra_4$ is hydrogen or $C_1$-$C_4$haloalkyl, in particular trifluoromethyl;
$R_{14}$ is $C_1$-$C_4$alkyl, in particular methyl or ethyl;
$R_8$ is hydrogen or $C_1$-$C_4$alkyl, in particular methyl or ethyl;
$R_9$ is hydrogen, $C_1$-$C_4$alkyl or halogen, in particular hydrogen, chlorine or methyl;
and agrochemically acceptable salts, stereoisomers, enantiomers, tautomers and N-oxides of the compounds of formula I-4.

In said preferred embodiment comprising compounds of formula I-4, $R_{10}'$ is preferably a diazine radical selected from the group consisting of formula DA1 to DA5 monosubstituted by substituents independently selected from the group consisting of halogen, cyano, $C_1$-$C_4$haloalkoxy and $C_1$-$C_4$haloalkyl. Especially preferred is a substituent selected from fluorine, chlorine, cyano, difluoromethoxy, trifluoromethoxy, trifluoromethyl and pentafluoroethyl. Yet further preferred compounds of formula I-4 have $R_{10}'$ defined as DA5, wherein $R_{10}'$ is monosubstituted by substituents independently selected from the group consisting of halogen, cyano, $C_1$-$C_4$haloalkoxy and $C_1$-$C_4$haloalkyl, in particular from fluorine, chlorine, cyano, difluoromethoxy, trifluoromethoxy, trifluoromethyl and pentafluoroethyl.

The process according to the invention for preparing compounds of formula I is carried out in principle by methods known to those skilled in the art. More specifically, the subgroup of compounds of formula I, wherein X is SO (sulfoxide) and/or $SO_2$ (sulfone), may be obtained by means of an oxidation reaction of the corresponding sulfide compounds of formula I, wherein X is S, involving reagents such as, for example, m-chloroperoxybenzoic acid (mCPBA), hydrogen peroxide, oxone, sodium periodate, sodium hypochlorite or tert-butyl hypochlorite amongst other oxidants. The oxidation reaction is generally conducted in the presence of a solvent. Examples of the solvent to be used in the reaction include aliphatic halogenated hydrocarbons such as dichloromethane and chloroform; alcohols such as methanol and ethanol; acetic acid; water; and mixtures thereof. The amount of the oxidant to be used in the reaction is generally 1 to 3 moles, preferably 1 to 1.2 moles, relative to 1 mole of the sulfide compounds I to produce the sulfoxide compounds I, and preferably 2 to 2.2 moles of oxidant, relative to 1 mole of the sulfide compounds I to produce the sulfone compounds I. Such oxidation reactions are disclosed, for example, in WO 2013/018928.

In the following schemes, the radical J represents the group

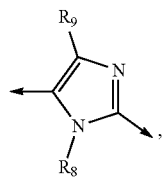
(J)

wherein the arrow to the left of J denotes the point of attachment to the fragment

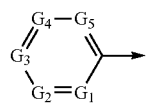

and wherein the arrow to the right of J denotes the point of attachment to the radical Q; and wherein $R_8$ and $R_9$ is as defined under formula I above.

Compounds of formula I

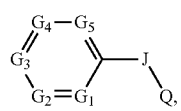
(I)

wherein $G_1$, $G_2$, $G_3$, $G_4$, $G_5$, J and Q are as defined above may be prepared by reacting a compound of formula II

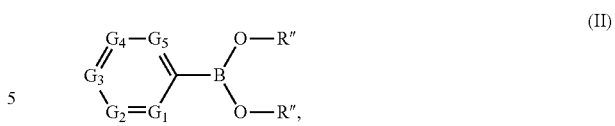
(II)

wherein $G_1$, $G_2$, $G_3$, $G_4$ and $G_5$ are as defined above, and wherein R" is for example hydrogen (in that case the compound of the formula II is a boronic acid) or $C_1$-$C_4$alkyl (boronic ester), with a compound of formula III

(III)

wherein J and Q are as defined above and $L_G$ is a halogen, preferably bromine or iodine, or a pseudohalogen such as $C_{1-4}$haloalkylsulfonate, especially triflate, by means of a transition metal-catalyzed reaction. Indeed, the boronic acid of the formula II, or a suitable salt or ester thereof, will react with a compound of the formula III under palladium- or nickel-catalyzed conditions, such as for example the Suzuki-Miyaura conditions. Such cross coupling reactions are carried out in the presence of a base, such as sodium, potassium or cesium carbonate, in an inert solvent, such as tetrahydrofuran, N,N-dimethylformamide, dioxane or 1,2-dimethoxyethane, or such as 1,2-dimethoxyethane-water mixtures, at temperatures between 25-200° C., preferably 50-150° C., optionally under microwave irradiation. A variety of metals, catalysts and ligands may be used in this reaction type, such as for example [1,1-bis(diphenylphosphino)ferrocene]dichloropalladium(II) ($PdCl_2$(dppf)) or bis(triphenylphosphine) palladium(II) dichloride ($PdCl_2(PPh_3)_2$). Reaction conditions and catalytic systems for such a transformation have been described, for example, in WO08/071405. Alternative boron-based reagents of the formula type II may include boronic esters (also named boronate esters) derived from 2,3-dimethyl-2,3-butanediol (IIa), 2,2-dimethyl-1,3-propanediol (IIb), and 1,3-propanediol (IIc), and salt analogues of II, such as organotrifluoroborates, for example potassium trifluoroborate salts (IId).

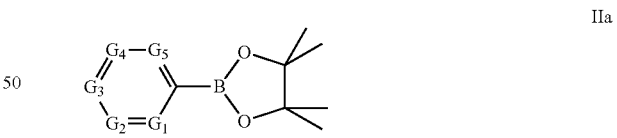
IIa

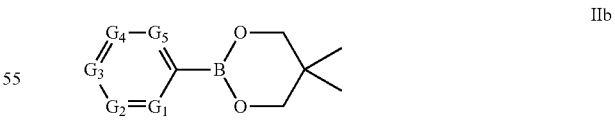
IIb

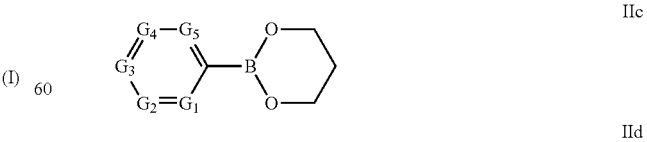
IIc

IId

Compounds of formula (IIIa)

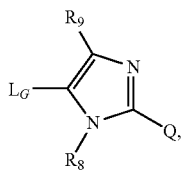

wherein Q and $R_8$ are as defined under formula I above, and wherein $L_G$ is a halogen, preferably iodine or bromine, and wherein $R_9$ is preferably hydrogen, are novel and especially developed for the preparation of the compounds of formula I of this invention. The compounds of formula (IIIa) therefore constitute a further object of the invention. The preferred substituent definitions for the compounds of formula I are also valid for the compounds of formula (IIIa).

Compounds of formula III

wherein J and Q are as defined above, and wherein $L_G$ is a halogen, preferably bromine or iodine, may be prepared by reacting a compound of formula IV

wherein J and Q are as defined above, with a reagent such as N-chlorosuccinimide (NCS), N-bromosuccinimide (NBS) or N-iodosuccinimide (NIS), or alternatively chlorine, bromine or iodine. Such halogenation reactions are carried out in an inert solvent, such as chloroform, carbon tetrachloride, 1,2-dichloroethane, acetic acid, ethers, acetonitrile or N,N-dimethylformamide, at temperatures between 25-200° C., preferably 25-100° C., as described, for example, in K. G. Holden et al., J. Org. Chem. 2002, 67, 5913-5918.

Compounds of formula IVa

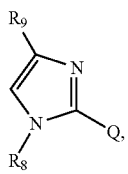

wherein Q and $R_8$ are as defined under formula I above, and wherein $R_9$ is preferably hydrogen, are novel and especially developed for the preparation of the compounds of formula I of this invention. The compounds of formula IVa therefore constitute a further object of the invention. The preferred substituent definitions for the compounds of formula I are also valid for the compounds of formula IVa.

The subgroup of compounds of formula III and IV, wherein J, Q and $L_G$ are as defined above and wherein X is SO (sulfoxide) and/or $SO_2$ (sulfone), may be obtained by means of an oxidation reaction of the corresponding sulfide compounds of formula III or IV, wherein X is S (sulfide), involving reagents such as, for example, m-chloroperoxybenzoic acid (mCPBA), hydrogen peroxide, oxone, sodium periodate, sodium hypochlorite or tert-butyl hypochlorite amongst other oxidants. The oxidation reaction is generally conducted in the presence of a solvent. Examples of the solvent to be used in the reaction include aliphatic halogenated hydrocarbons such as dichloromethane and chloroform; alcohols such as methanol and ethanol; acetic acid; water; and mixtures thereof. The amount of the oxidant to be used in the reaction is generally 1 to 3 moles, preferably 1 to 1.2 moles, relative to 1 mole of the sulfide compounds III or IV to produce the sulfoxide compounds III or IV, and preferably 2 to 2.2 moles of oxidant, relative to 1 mole of the sulfide compounds III or IV to produce the sulfone compounds III or IV. Such oxidation reactions are disclosed, for example, in WO 2013/018928.

Compounds of formula IV, wherein J and Q are as defined above and wherein X is S (sulfide), can be prepared by reacting a compound of formula V

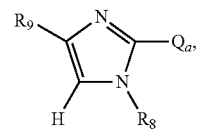

wherein $R_8$ and $R_9$ are as described in formula I and wherein $Q_a$ is a radical selected from the group consisting of formula $Q_{1a}$ to $Q_{2a}$:

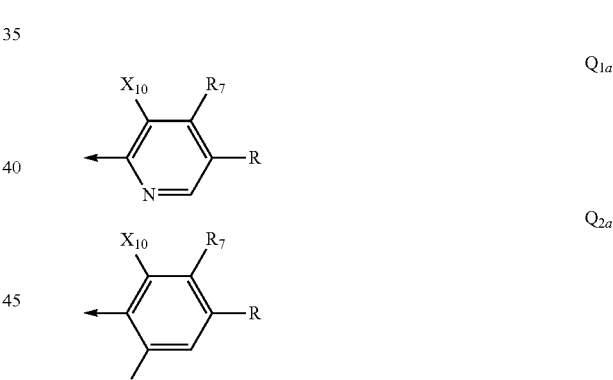

wherein R and $R_7$ are as defined above, and wherein $X_{10}$ is a halogen,
with a compound of formula VI $R_1$—SH     (VI), or a salt thereof, wherein $R_1$ is as defined in formula I, optionally in the presence of a suitable base, such as alkali metal carbonates, for example sodium carbonate and potassium carbonate, or alkali metal hydrides such as sodium hydride, or alkali metal hydroxides such as sodium hydroxide and potassium hydroxide, in an inert solvent at temperatures preferably between 25-120° C. Examples of solvent to be used include ethers such as THF, ethylene glycol dimethyl ether, tert-butylmethyl ether, and 1,4-dioxane, aromatic hydrocarbons such as toluene and xylene, nitriles such as acetonitrile or polar aprotic solvents such as N,N-dimethylformamide, N,N-dimethylacetamide, N-methyl-2-pyrrolidone or dimethyl sulfoxide. Examples of salts of the compound of formula VI include compounds of the formula VIa

 (VIa), wherein $R_1$ is as defined above and wherein M is, for example, sodium or potassium.

Compounds of formula V, wherein $R_8$, $R_9$ and $Q_a$ are as defined above, can be prepared by reacting a compound of formula VII

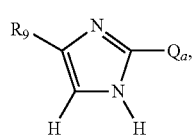

or a salt and/or a tautomer thereof, wherein $R_9$ and $Q_a$ are as described above,
with an alkylating agent of the formula

 (VIII), wherein $R_8$ is as defined above, and wherein $L_{G2}$ is a halogen (especially bromine or iodine), or a leaving group $OSO_2R_{38}$, wherein $R_{38}$ is $C_1$-$C_6$alkyl, $C_1$-$C_6$haloalkyl, or phenyl optionally substituted by nitro or $C_1$-$C_3$alkyl (especially a sulfonate such as mesylate, triflate or tosylate) or a sulfate (forming the alkylating agent VIII dimethylsulfate, in the particular situation where $R_8$ is methyl), preferably in the presence of a suitable base, such as sodium hydride or sodium, potassium or cesium carbonate, in an inert solvent such as tetrahydrofuran, dioxane, acetonitrile, N,N-dimethylformamide, N,N-dimethylacetamide, N-methyl-2-pyrrolidone or dimethyl sulfoxide, at temperatures between 20-150° C.

Compounds of formula VII, or a salt and/or a tautomer thereof, wherein $R_9$ and $Q_a$ are as defined above, can be prepared by reacting a nitrile compound of formula IX

 (IX), wherein $Q_a$ is as described above,
sequentially with
i) a catalytic amount, preferably 0.01 to 0.5 equivalent, of a base such as an alkoxide, preferably sodium methoxide NaOMe or sodium ethoxide NaOEt, in an alcoholic solvent, such as methanol or ethanol, at temperatures between 0-100° C., to generate an imidate intermediate of the formula $INT_1$ (or a salt and/or a tautomer thereof); followed by
ii) acidification of the reaction mixture with, for example, acetic acid or the like, and treatment with an aminoacetal reagent of formula X

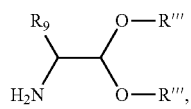 (X)

or a salt thereof, wherein R''' is $C_1$-$C_6$alkyl and $R_9$ is as defined above, at temperatures between 0-150° C., to generate an amidine-acetal intermediate of the formula $INT_2$ (or a salt and/or a tautomer thereof); followed by
iii) deprotection of the acetal with, for example, aqueous hydrochloric acid or the like, and concomitant cyclization, at temperatures between 0-150° C., to form the compound of the formula VII, or a salt and/or a tautomer thereof. The described process to prepare compounds of the formula VII from compounds of the formula IX may include isolation and purification of the intermediates $INT_1$ and $INT_2$, (which may be isolated as free bases or as salts (e.g. a hydrohalide salt, more specifically a hydrochloride or hydrobromide salt, or any other equivalent salt)), however, this process is advantageously conducted as a one-pot preparation as described, for example, in M. E. Voss et al., Tetrahedron 2008, 64, 645-651. The process is summarized in scheme 1 for the particular situation where $R_9$ is hydrogen:

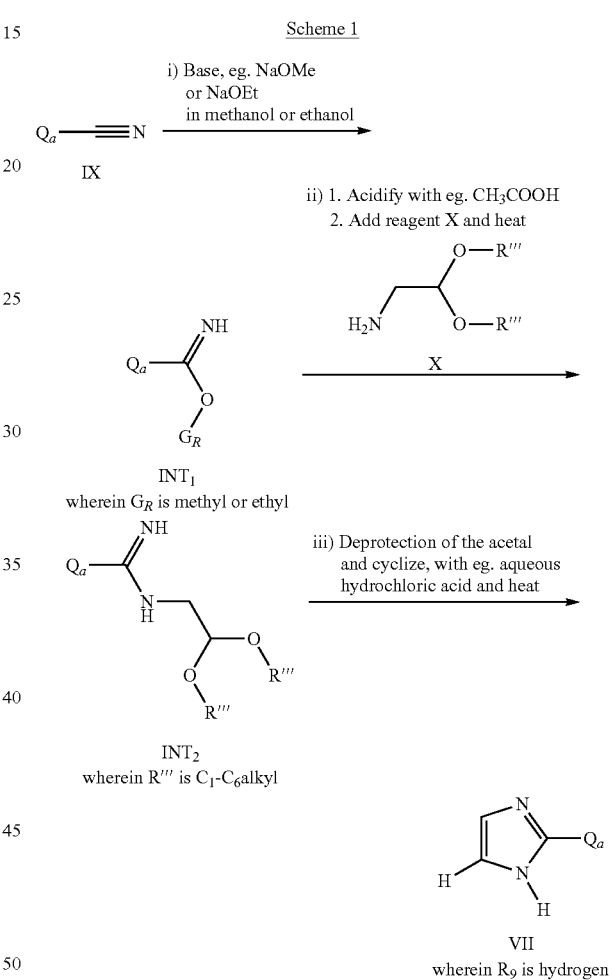

Compounds of the formula INT1 may alternatively be prepared under conditions and variants of the Pinner reaction known to a person skilled in the art, typically by treating a compound of the formula IX with a hydrohalide acid, preferably hydrochloric acid, in presence of alcoholic reagents such as methanol or ethanol, preferably in an inert solvent such as diethyl ether, tetrahydrofuran or dioxane, at temperatures between −40 and 50° C., preferably between −20 and 20° C.

Compounds of formula IX, wherein Qa is as described above and reagents of formula X, wherein $R_9$ and R''' are as described above, are known compounds or can be prepared by known methods, described in the literature.

Alternatively, compounds of formula I may be prepared from compounds of formula V involving the same chemistry as described above, but by changing the order of the steps. This alternative route is summarized in scheme 2.

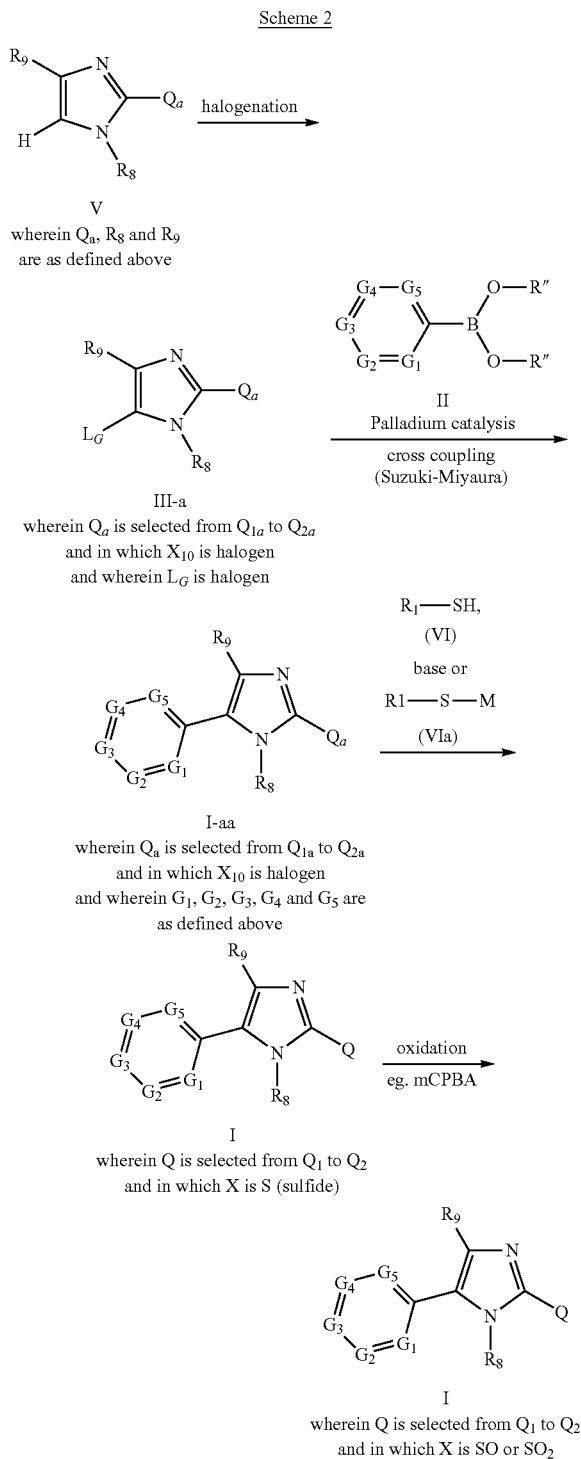

The reactants can be reacted in the presence of a base. Examples of suitable bases are alkali metal or alkaline earth metal hydroxides, alkali metal or alkaline earth metal hydrides, alkali metal or alkaline earth metal amides, alkali metal or alkaline earth metal alkoxides, alkali metal or alkaline earth metal acetates, alkali metal or alkaline earth metal carbonates, alkali metal or alkaline earth metal dialkylamides or alkali metal or alkaline earth metal alkylsilylamides, alkylamines, alkylenediamines, free or N-alkylated saturated or unsaturated cycloalkylamines, basic heterocycles, ammonium hydroxides and carbocyclic amines. Examples which may be mentioned are sodium hydroxide, sodium hydride, sodium amide, sodium methoxide, sodium acetate, sodium carbonate, potassium tert-butoxide, potassium hydroxide, potassium carbonate, potassium hydride, lithium diisopropylamide, potassium bis(trimethylsilyl)amide, calcium hydride, triethylamine, diisopropylethylamine, triethylenediamine, cyclohexylamine, N-cyclohexyl-N,N-dimethylamine, N,N-diethylaniline, pyridine, 4-(N,N-dimethylamino)pyridine, quinuclidine, N-methylmorpholine, benzyltrimethylammonium hydroxide and 1,8-diazabicyclo [5.4.0]undec-7-ene (DBU).

The reactants can be reacted with each other as such, i.e. without adding a solvent or diluent. In most cases, however, it is advantageous to add an inert solvent or diluent or a mixture of these. If the reaction is carried out in the presence of a base, bases which are employed in excess, such as triethylamine, pyridine, N-methylmorpholine or N,N-diethylaniline, may also act as solvents or diluents.

The reaction is advantageously carried out in a temperature range from approximately −80° C. to approximately +140° C., preferably from approximately −30° C. to approximately +100° C., in many cases in the range between ambient temperature and approximately +80° C.

A compound of formula I can be converted in a manner known per se into another compound of formula I by replacing one or more substituents of the starting compound of formula I in the customary manner by (an)other substituent(s) according to the invention.

Depending on the choice of the reaction conditions and starting materials which are suitable in each case, it is possible, for example, in one reaction step only to replace one substituent by another substituent according to the invention, or a plurality of substituents can be replaced by other substituents according to the invention in the same reaction step.

Salts of compounds of formula I can be prepared in a manner known per se. Thus, for example, acid addition salts of compounds of formula I are obtained by treatment with a suitable acid or a suitable ion exchanger reagent and salts with bases are obtained by treatment with a suitable base or with a suitable ion exchanger reagent.

Salts of compounds of formula I can be converted in the customary manner into the free compounds I, acid addition salts, for example, by treatment with a suitable basic compound or with a suitable ion exchanger reagent and salts with bases, for example, by treatment with a suitable acid or with a suitable ion exchanger reagent.

Salts of compounds of formula I can be converted in a manner known per se into other salts of compounds of formula I, acid addition salts, for example, into other acid addition salts, for example by treatment of a salt of inorganic acid such as hydrochloride with a suitable metal salt such as a sodium, barium or silver salt, of an acid, for example with silver acetate, in a suitable solvent in which an inorganic salt which forms, for example silver chloride, is insoluble and thus precipitates from the reaction mixture.

Depending on the procedure or the reaction conditions, the compounds of formula I, which have salt-forming properties can be obtained in free form or in the form of salts.

The compounds of formula I and, where appropriate, the tautomers thereof, in each case in free form or in salt form, can be present in the form of one of the isomers which are possible or as a mixture of these, for example in the form of pure isomers, such as antipodes and/or diastereomers, or as isomer mixtures, such as enantiomer mixtures, for example racemates, diastereomer mixtures or racemate mixtures, depending on the number, absolute and relative configuration of asymmetric carbon atoms which occur in the molecule and/or depending on the configuration of non-aromatic double bonds which occur in the molecule; the invention relates to the pure isomers and also to all isomer mixtures which are possible and is to be understood in each case in this sense hereinabove and hereinbelow, even when stereochemical details are not mentioned specifically in each case.

Diastereomer mixtures or racemate mixtures of compounds of formula I, in free form or in salt form, which can be obtained depending on which starting materials and procedures have been chosen can be separated in a known manner into the pure diasteromers or racemates on the basis of the physicochemical differences of the components, for example by fractional crystallization, distillation and/or chromatography.

Enantiomer mixtures, such as racemates, which can be obtained in a similar manner can be resolved into the optical antipodes by known methods, for example by recrystallization from an optically active solvent, by chromatography on chiral adsorbents, for example high-performance liquid chromatography (HPLC) on acetyl celulose, with the aid of suitable microorganisms, by cleavage with specific, immobilized enzymes, via the formation of inclusion compounds, for example using chiral crown ethers, where only one enantiomer is complexed, or by conversion into diastereomeric salts, for example by reacting a basic end-product racemate with an optically active acid, such as a carboxylic acid, for example camphor, tartaric or malic acid, or sulfonic acid, for example camphorsulfonic acid, and separating the diastereomer mixture which can be obtained in this manner, for example by fractional crystallization based on their differing solubilities, to give the diastereomers, from which the desired enantiomer can be set free by the action of suitable agents, for example basic agents.

Pure diastereomers or enantiomers can be obtained according to the invention not only by separating suitable isomer mixtures, but also by generally known methods of diastereoselective or enantioselective synthesis, for example by carrying out the process according to the invention with starting materials of a suitable stereochemistry.

N-oxides can be prepared by reacting a compound of the formula I with a suitable oxidizing agent, for example the $H_2O_2$/urea adduct in the presence of an acid anhydride, e.g. trifluoroacetic anhydride. Such oxidations are known from the literature, for example from J. Med. Chem., 32 (12), 2561-73, 1989 or WO 00/15615.

It is advantageous to isolate or synthesize in each case the biologically more effective isomer, for example enantiomer or diastereomer, or isomer mixture, for example enantiomer mixture or diastereomer mixture, if the individual components have a different biological activity.

The compounds of formula I and, where appropriate, the tautomers thereof, in each case in free form or in salt form, can, if appropriate, also be obtained in the form of hydrates and/or include other solvents, for example those which may have been used for the crystallization of compounds which are present in solid form.

The compounds according to the following Tables 1 to 6 below can be prepared according to the methods described above. The examples which follow are intended to illustrate the invention and show preferred compounds of formula I.

Table 1:

This table discloses the 118 compounds 1.001 to 1.118 of the formula I-1a:

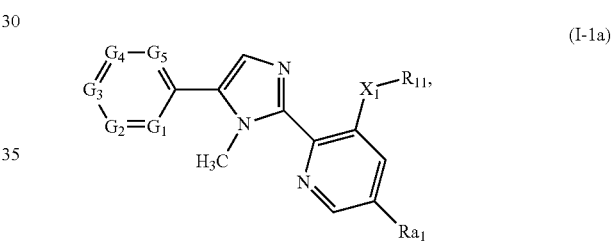

wherein $X_1$ is S, and $Ra_1$, $R_{11}$, $G_1$, $G_2$, $G_3$, $G_4$ and $G_5$ are as defined below:

TABLE 1

| Comp. No | $Ra_1$ | $R_{11}$ | $G_1$ | $G_2$ | $G_3$ | $G_4$ | $G_5$ |
|---|---|---|---|---|---|---|---|
| 1.001 | H | —CH$_2$CH$_3$ | CH | CH | C(CF$_3$) | CH | CH |
| 1.002 | CF$_3$ | —CH$_2$CH$_3$ | CH | CH | C(CF$_3$) | CH | CH |
| 1.003 | H | —CH$_2$CH$_3$ | CH | C(CF$_3$) | CH | CH | CH |
| 1.004 | CF$_3$ | —CH$_2$CH$_3$ | CH | C(CF$_3$) | CH | CH | CH |
| 1.005 | H | —CH$_2$CH$_3$ | N | C(CF$_3$) | CH | CH | CH |
| 1.006 | CF$_3$ | —CH$_2$CH$_3$ | N | C(CF$_3$) | CH | CH | CH |
| 1.007 | H | —CH$_2$CH$_3$ | N | CH | C(CF$_3$) | CH | CH |
| 1.008 | CF$_3$ | —CH$_2$CH$_3$ | N | CH | C(CF$_3$) | CH | CH |
| 1.009 | H | —CH$_2$CH$_3$ | N | CH | CH | C(CF$_3$) | CH |
| 1.010 | CF$_3$ | —CH$_2$CH$_3$ | N | CH | CH | C(CF$_3$) | CH |
| 1.011 | H | —CH$_2$CH$_3$ | CH | N | C(CF$_3$) | CH | CH |
| 1.012 | CF$_3$ | —CH$_2$CH$_3$ | CH | N | C(CF$_3$) | CH | CH |
| 1.013 | H | —CH$_2$CH$_3$ | CH | N | CH | C(CF$_3$) | CH |
| 1.014 | CF$_3$ | —CH$_2$CH$_3$ | CH | N | CH | C(CF$_3$) | CH |
| 1.015 | H | —CH$_2$CH$_3$ | CH | C(CF$_3$) | N | CH | CH |
| 1.016 | CF$_3$ | —CH$_2$CH$_3$ | CH | C(CF$_3$) | N | CH | CH |
| 1.017 | H | —CH$_3$ | CH | CH | C(CF$_3$) | CH | CH |
| 1.018 | CF$_3$ | —CH$_3$ | CH | CH | C(CF$_3$) | CH | CH |
| 1.019 | OCF$_3$ | —CH$_2$CH$_3$ | CH | CH | C(CF$_3$) | CH | CH |
| 1.020 | OCHF$_2$ | —CH$_2$CH$_3$ | CH | CH | C(CF$_3$) | CH | CH |
| 1.021 | CF$_2$CF$_3$ | —CH$_2$CH$_3$ | CH | CH | C(CF$_3$) | CH | CH |
| 1.022 | CF$_3$ | —CH$_2$CH$_3$ | CH | CH | C(CN) | CH | CH |
| 1.023 | H | —CH$_2$CH$_3$ | CH | CH | C(OCF$_3$) | CH | CH |
| 1.024 | CF$_3$ | —CH$_2$CH$_3$ | CH | CH | C(OCF$_3$) | CH | CH |
| 1.025 | CF$_3$ | —CH$_3$ | CH | CH | C(OCF$_3$) | CH | CH |

TABLE 1-continued

| Comp. No | Ra$_1$ | R$_{11}$ | G$_1$ | G$_2$ | G$_3$ | G$_4$ | G$_5$ |
|---|---|---|---|---|---|---|---|
| 1.026 | H | —CH$_2$CH$_3$ | CH | CH | C(CF$_2$CF$_3$) | CH | CH |
| 1.027 | CF$_3$ | —CH$_2$CH$_3$ | CH | CH | C(CF$_2$CF$_3$) | CH | CH |
| 1.028 | CF$_3$ | —CH$_3$ | CH | CH | C(CF$_2$CF$_3$) | CH | CH |
| 1.029 | H | —CH$_3$ | CH | C(CF$_3$) | CH | CH | CH |
| 1.030 | CF$_3$ | —CH$_3$ | CH | C(CF$_3$) | CH | CH | CH |
| 1.031 | OCF$_3$ | —CH$_2$CH$_3$ | CH | C(CF$_3$) | CH | CH | CH |
| 1.032 | OCHF$_2$ | —CH$_2$CH$_3$ | CH | C(CF$_3$) | CH | CH | CH |
| 1.033 | CF$_2$CF$_3$ | —CH$_2$CH$_3$ | CH | C(CF$_3$) | CH | CH | CH |
| 1.034 | CF$_3$ | —CH$_2$CH$_3$ | CH | C(CN) | CH | CH | CH |
| 1.035 | H | —CH$_2$CH$_3$ | CH | C(OCF$_3$) | CH | CH | CH |
| 1.036 | CF$_3$ | —CH$_2$CH$_3$ | CH | C(OCF$_3$) | CH | CH | CH |
| 1.037 | CF$_3$ | —CH$_3$ | CH | C(OCF$_3$) | CH | CH | CH |
| 1.038 | H | —CH$_2$CH$_3$ | CH | C(CF$_2$CF$_3$) | CH | CH | CH |
| 1.039 | CF$_3$ | —CH$_2$CH$_3$ | CH | C(CF$_2$CF$_3$) | CH | CH | CH |
| 1.040 | CF$_3$ | —CH$_3$ | CH | C(CF$_2$CF$_3$) | CH | CH | CH |
| 1.041 | H | —CH$_3$ | N | CH | C(CF$_3$) | CH | CH |
| 1.042 | CF$_3$ | —CH$_3$ | N | CH | C(CF$_3$) | CH | CH |
| 1.043 | OCF$_3$ | —CH$_2$CH$_3$ | N | CH | C(CF$_3$) | CH | CH |
| 1.044 | OCHF$_2$ | —CH$_2$CH$_3$ | N | CH | C(CF$_3$) | CH | CH |
| 1.045 | CF$_2$CF$_3$ | —CH$_2$CH$_3$ | N | CH | C(CF$_3$) | CH | CH |
| 1.046 | CF$_3$ | —CH$_2$CH$_3$ | N | CH | C(CN) | CH | CH |
| 1.047 | H | —CH$_2$CH$_3$ | N | CH | C(OCF$_3$) | CH | CH |
| 1.048 | CF$_3$ | —CH$_2$CH$_3$ | N | CH | C(OCF$_3$) | CH | CH |
| 1.049 | CF$_3$ | —CH$_3$ | N | CH | C(OCF$_3$) | CH | CH |
| 1.050 | H | —CH$_2$CH$_3$ | N | CH | C(CF$_2$CF$_3$) | CH | CH |
| 1.051 | CF$_3$ | —CH$_2$CH$_3$ | N | CH | C(CF$_2$CF$_3$) | CH | CH |
| 1.052 | CF$_3$ | —CH$_3$ | N | CH | C(CF$_2$CF$_3$) | CH | CH |
| 1.053 | H | —CH$_3$ | N | CH | CH | C(CF$_3$) | CH |
| 1.054 | CF$_3$ | —CH$_3$ | N | CH | CH | C(CF$_3$) | CH |
| 1.055 | OCF$_3$ | —CH$_2$CH$_3$ | N | CH | CH | C(CF$_3$) | CH |
| 1.056 | OCHF$_2$ | —CH$_2$CH$_3$ | N | CH | CH | C(CF$_3$) | CH |
| 1.057 | CF$_2$CF$_3$ | —CH$_2$CH$_3$ | N | CH | CH | C(CF$_3$) | CH |
| 1.058 | CF$_3$ | —CH$_2$CH$_3$ | N | CH | CH | C(CN) | CH |
| 1.059 | H | —CH$_2$CH$_3$ | N | CH | CH | C(OCF$_3$) | CH |
| 1.060 | CF$_3$ | —CH$_2$CH$_3$ | N | CH | CH | C(OCF$_3$) | CH |
| 1.061 | CF$_3$ | —CH$_3$ | N | CH | CH | C(OCF$_3$) | CH |
| 1.062 | H | —CH$_2$CH$_3$ | N | CH | CH | C(CF$_2$CF$_3$) | CH |
| 1.063 | CF$_3$ | —CH$_2$CH$_3$ | N | CH | CH | C(CF$_2$CF$_3$) | CH |
| 1.064 | CF$_3$ | —CH$_3$ | N | CH | CH | C(CF$_2$CF$_3$) | CH |
| 1.065 | H | —CH$_3$ | CH | N | C(CF$_3$) | CH | CH |
| 1.066 | CF$_3$ | —CH$_3$ | CH | N | C(CF$_3$) | CH | CH |
| 1.067 | OCF$_3$ | —CH$_2$CH$_3$ | CH | N | C(CF$_3$) | CH | CH |
| 1.068 | OCHF$_2$ | —CH$_2$CH$_3$ | CH | N | C(CF$_3$) | CH | CH |
| 1.069 | CF$_2$CF$_3$ | —CH$_2$CH$_3$ | CH | N | C(CF$_3$) | CH | CH |
| 1.070 | CF$_3$ | —CH$_2$CH$_3$ | CH | N | C(CN) | CH | CH |
| 1.071 | H | —CH$_2$CH$_3$ | CH | N | C(OCF$_3$) | CH | CH |
| 1.072 | CF$_3$ | —CH$_2$CH$_3$ | CH | N | C(OCF$_3$) | CH | CH |
| 1.073 | CF$_3$ | —CH$_3$ | CH | N | C(OCF$_3$) | CH | CH |
| 1.074 | H | —CH$_2$CH$_3$ | CH | N | C(CF$_2$CF$_3$) | CH | CH |
| 1.075 | CF$_3$ | —CH$_2$CH$_3$ | CH | N | C(CF$_2$CF$_3$) | CH | CH |
| 1.076 | CF$_3$ | —CH$_3$ | CH | N | C(CF$_2$CF$_3$) | CH | CH |
| 1.077 | H | —CH$_3$ | CH | N | CH | C(CF$_3$) | CH |
| 1.078 | CF$_3$ | —CH$_3$ | CH | N | CH | C(CF$_3$) | CH |
| 1.079 | OCF$_3$ | —CH$_2$CH$_3$ | CH | N | CH | C(CF$_3$) | CH |
| 1.080 | OCHF$_2$ | —CH$_2$CH$_3$ | CH | N | CH | C(CF$_3$) | CH |
| 1.081 | CF$_2$CF$_3$ | —CH$_2$CH$_3$ | CH | N | CH | C(CF$_3$) | CH |
| 1.082 | CF$_3$ | —CH$_2$CH$_3$ | CH | N | CH | C(CN) | CH |
| 1.083 | H | —CH$_2$CH$_3$ | CH | N | CH | C(OCF$_3$) | CH |
| 1.084 | CF$_3$ | —CH$_2$CH$_3$ | CH | N | CH | C(OCF$_3$) | CH |
| 1.085 | CF$_3$ | —CH$_3$ | CH | N | CH | C(OCF$_3$) | CH |
| 1.086 | H | —CH$_2$CH$_3$ | CH | N | CH | C(CF$_2$CF$_3$) | CH |
| 1.087 | CF$_3$ | —CH$_2$CH$_3$ | CH | N | CH | C(CF$_2$CF$_3$) | CH |
| 1.088 | CF$_3$ | —CH$_3$ | CH | N | CH | C(CF$_2$CF$_3$) | CH |
| 1.089 | CF$_3$ | —CH$_2$CH$_3$ | N | —OCF2O— | | CH | CH |
| 1.090 | CF$_3$ | —CH$_2$CH$_3$ | N | CH | —OCF2O— | | CH |
| 1.091 | CF$_3$ | —CH$_2$CH$_3$ | N | CH | CH | —OCF2O— | |
| 1.092 | CF$_3$ | —CH$_2$CH$_3$ | CH | N | —OCF2O— | | CH |
| 1.093 | CF$_3$ | —CH$_2$CH$_3$ | CH | N | CH | —OCF2O— | |
| 1.094 | CF$_3$ | —CH$_2$CH$_3$ | N | C(CF$_3$) | N | C(CF$_3$) | CH |
| 1.095 | CF$_3$ | —CH$_2$CH$_3$ | N | CH | N | C(CF$_3$) | CH |
| 1.096 | CF$_3$ | —CH$_2$CH$_3$ | N | C(CF$_3$) | CH | N | CH |
| 1.097 | CF$_3$ | —CH$_2$CH$_3$ | N | CH | C(CF$_3$) | N | CH |
| 1.098 | CF$_3$ | —CH$_2$CH$_3$ | N | C(CF$_3$) | CH | CH | N |
| 1.099 | CF$_3$ | —CH$_2$CH$_3$ | N | CH | C(CF$_3$) | CH | N |
| 1.100 | CF$_3$ | —CH$_2$CH$_3$ | N | N | C(CF$_3$) | CH | CH |
| 1.101 | CF$_3$ | —CH$_2$CH$_3$ | N | N | CH | C(CF$_3$) | CH |
| 1.102 | CF$_3$ | —CH$_2$CH$_3$ | CH | N | C(CF$_3$) | N | CH |
| 1.103 | H | —CH$_2$CH$_3$ | CH | CH | C(SCF$_3$) | CH | CH |

TABLE 1-continued

| Comp. No | Ra$_1$ | R$_{11}$ | G$_1$ | G$_2$ | G$_3$ | G$_4$ | G$_5$ |
|---|---|---|---|---|---|---|---|
| 1.104 | CF$_3$ | —CH$_2$CH$_3$ | CH | CH | C(SCF$_3$) | CH | CH |
| 1.105 | H | —CH$_2$CH$_3$ | CH | C(SCF$_3$) | CH | CH | CH |
| 1.106 | CF$_3$ | —CH$_2$CH$_3$ | CH | C(SCF$_3$) | CH | CH | CH |
| 1.107 | H | —CH$_2$CH$_3$ | CH | N | C(SCF$_3$) | CH | CH |
| 1.108 | CF$_3$ | —CH$_2$CH$_3$ | CH | N | C(SCF$_3$) | CH | CH |
| 1.109 | H | —CH$_2$CH$_3$ | N | CH | CH | C(SCF$_3$) | CH |
| 1.110 | CF$_3$ | —CH$_2$CH$_3$ | N | CH | CH | C(SCF$_3$) | CH |
| 1.111 | H | —CH$_2$CH$_3$ | CH | CH | C(SO$_2$CF$_3$) | CH | CH |
| 1.112 | CF$_3$ | —CH$_2$CH$_3$ | CH | CH | C(SO$_2$CF$_3$) | CH | CH |
| 1.113 | H | —CH$_2$CH$_3$ | CH | C(SO$_2$CF$_3$) | CH | CH | CH |
| 1.114 | CF$_3$ | —CH$_2$CH$_3$ | CH | C(SO$_2$CF$_3$) | CH | CH | CH |
| 1.115 | H | —CH$_2$CH$_3$ | CH | N | C(SO$_2$CF$_3$) | CH | CH |
| 1.116 | CF$_3$ | —CH$_2$CH$_3$ | CH | N | C(SO$_2$CF$_3$) | CH | CH |
| 1.117 | H | —CH$_2$CH$_3$ | N | CH | CH | C(SO$_2$CF$_3$) | CH |
| 1.118 | CF$_3$ | —CH$_2$CH$_3$ | N | CH | CH | C(SO$_2$CF$_3$) | CH | and the N-oxides of the compounds of Table 1.

Table 2:

This table discloses the 118 compounds 2.001 to 2.118 of the formula I-1a, wherein X$_1$ is SO, and Ra$_1$, R$_{11}$, G$_1$, G$_2$, G$_3$, G$_4$ and G$_5$ are as defined in Table 1.

Table 3:

This table discloses the 118 compounds 3.001 to 3.118 of the formula I-1a, wherein X$_1$ is SO$_2$, and Ra$_1$, R$_{11}$, G$_1$, G$_2$, G$_3$, G$_4$ and G$_5$ are as defined in Table 1.

Table 4:

This table discloses the 118 compounds 4.001 to 4.118 of the formula I-2a:

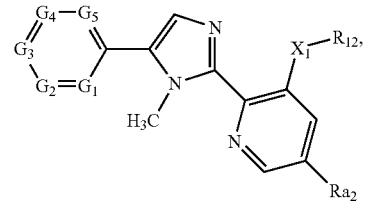

(I-2a)

wherein X$_2$ is S, and Ra$_2$, R$_{12}$, G$_1$, G$_2$, G$_3$, G$_4$ and G$_5$ are as defined below:

TABLE 4

| Comp. No | Ra$_2$ | R$_{12}$ | G$_1$ | G$_2$ | G$_3$ | G$_4$ | G$_5$ |
|---|---|---|---|---|---|---|---|
| 4.001 | H | —CH$_2$CH$_3$ | CH | CH | C(CF$_3$) | CH | CH |
| 4.002 | CF$_3$ | —CH$_2$CH$_3$ | CH | CH | C(CF$_3$) | CH | CH |
| 4.003 | H | —CH$_2$CH$_3$ | CH | C(CF$_3$) | CH | CH | CH |
| 4.004 | CF$_3$ | —CH$_2$CH$_3$ | CH | C(CF$_3$) | CH | CH | CH |
| 4.005 | H | —CH$_2$CH$_3$ | N | C(CF$_3$) | CH | CH | CH |
| 4.006 | CF$_3$ | —CH$_2$CH$_3$ | N | C(CF$_3$) | CH | CH | CH |
| 4.007 | H | —CH$_2$CH$_3$ | N | CH | C(CF$_3$) | CH | CH |
| 4.008 | CF$_3$ | —CH$_2$CH$_3$ | N | CH | C(CF$_3$) | CH | CH |
| 4.009 | H | —CH$_2$CH$_3$ | N | CH | CH | C(CF$_3$) | CH |
| 4.010 | CF$_3$ | —CH$_2$CH$_3$ | N | CH | CH | C(CF$_3$) | CH |
| 4.011 | H | —CH$_2$CH$_3$ | CH | N | C(CF$_3$) | CH | CH |
| 4.012 | CF$_3$ | —CH$_2$CH$_3$ | CH | N | C(CF$_3$) | CH | CH |
| 4.013 | H | —CH$_2$CH$_3$ | CH | N | CH | C(CF$_3$) | CH |
| 4.014 | CF$_3$ | —CH$_2$CH$_3$ | CH | N | CH | C(CF$_3$) | CH |
| 4.015 | H | —CH$_2$CH$_3$ | CH | C(CF$_3$) | N | CH | CH |
| 4.016 | CF$_3$ | —CH$_2$CH$_3$ | CH | C(CF$_3$) | N | CH | CH |
| 4.017 | H | —CH$_3$ | CH | CH | C(CF$_3$) | CH | CH |
| 4.018 | CF$_3$ | —CH$_3$ | CH | CH | C(CF$_3$) | CH | CH |
| 4.019 | OCF$_3$ | —CH$_2$CH$_3$ | CH | CH | C(CF$_3$) | CH | CH |
| 4.020 | OCHF$_2$ | —CH$_2$CH$_3$ | CH | CH | C(CF$_3$) | CH | CH |
| 4.021 | CF$_2$CF$_3$ | —CH$_2$CH$_3$ | CH | CH | C(CF$_3$) | CH | CH |
| 4.022 | CF$_3$ | —CH$_2$CH$_3$ | CH | CH | C(CN) | CH | CH |
| 4.023 | H | —CH$_2$CH$_3$ | CH | CH | C(OCF$_3$) | CH | CH |
| 4.024 | CF$_3$ | —CH$_2$CH$_3$ | CH | CH | C(OCF$_3$) | CH | CH |
| 4.025 | CF$_3$ | —CH$_3$ | CH | CH | C(OCF$_3$) | CH | CH |
| 4.026 | H | —CH$_2$CH$_3$ | CH | CH | C(CF$_2$CF$_3$) | CH | CH |
| 4.027 | CF$_3$ | —CH$_2$CH$_3$ | CH | CH | C(CF$_2$CF$_3$) | CH | CH |
| 4.028 | CF$_3$ | —CH$_3$ | CH | CH | C(CF$_2$CF$_3$) | CH | CH |
| 4.029 | H | —CH$_3$ | CH | C(CF$_3$) | CH | CH | CH |
| 4.030 | CF$_3$ | —CH$_3$ | CH | C(CF$_3$) | CH | CH | CH |
| 4.031 | OCF$_3$ | —CH$_2$CH$_3$ | CH | C(CF$_3$) | CH | CH | CH |
| 4.032 | OCHF$_2$ | —CH$_2$CH$_3$ | CH | C(CF$_3$) | CH | CH | CH |
| 4.033 | CF$_2$CF$_3$ | —CH$_2$CH$_3$ | CH | C(CF$_3$) | CH | CH | CH |
| 4.034 | CF$_3$ | —CH$_2$CH$_3$ | CH | C(CN) | CH | CH | CH |
| 4.035 | H | —CH$_2$CH$_3$ | CH | C(OCF$_3$) | CH | CH | CH |
| 4.036 | CF$_3$ | —CH$_2$CH$_3$ | CH | C(OCF$_3$) | CH | CH | CH |
| 4.037 | CF$_3$ | —CH$_3$ | CH | C(OCF$_3$) | CH | CH | CH |

TABLE 4-continued

| Comp. No | Ra₂ | R₁₂ | G₁ | G₂ | G₃ | G₄ | G₅ |
|---|---|---|---|---|---|---|---|
| 4.038 | H | —CH₂CH₃ | CH | C(CF₂CF₃) | CH | CH | CH |
| 4.039 | CF₃ | —CH₂CH₃ | CH | C(CF₂CF₃) | CH | CH | CH |
| 4.040 | CF₃ | —CH₃ | CH | C(CF₂CF₃) | CH | CH | CH |
| 4.041 | H | —CH₃ | N | CH | C(CF₃) | CH | CH |
| 4.042 | CF₃ | —CH₃ | N | CH | C(CF₃) | CH | CH |
| 4.043 | OCF₃ | —CH₂CH₃ | N | CH | C(CF₃) | CH | CH |
| 4.044 | OCHF₂ | —CH₂CH₃ | N | CH | C(CF₃) | CH | CH |
| 4.045 | CF₂CF₃ | —CH₂CH₃ | N | CH | C(CF₃) | CH | CH |
| 4.046 | CF₃ | —CH₂CH₃ | N | CH | C(CN) | CH | CH |
| 4.047 | H | —CH₂CH₃ | N | CH | C(OCF₃) | CH | CH |
| 4.048 | CF₃ | —CH₂CH₃ | N | CH | C(OCF₃) | CH | CH |
| 4.049 | CF₃ | —CH₃ | N | CH | C(OCF₃) | CH | CH |
| 4.050 | H | —CH₂CH₃ | N | CH | C(CF₂CF₃) | CH | CH |
| 4.051 | CF₃ | —CH₂CH₃ | N | CH | C(CF₂CF₃) | CH | CH |
| 4.052 | CF₃ | —CH₃ | N | CH | C(CF₂CF₃) | CH | CH |
| 4.053 | H | —CH₃ | N | CH | CH | C(CF₃) | CH |
| 4.054 | CF₃ | —CH₃ | N | CH | CH | C(CF₃) | CH |
| 4.055 | OCF₃ | —CH₂CH₃ | N | CH | CH | C(CF₃) | CH |
| 4.056 | OCHF₂ | —CH₂CH₃ | N | CH | CH | C(CF₃) | CH |
| 4.057 | CF₂CF₃ | —CH₂CH₃ | N | CH | CH | C(CF₃) | CH |
| 4.058 | CF₃ | —CH₂CH₃ | N | CH | CH | C(CN) | CH |
| 4.059 | H | —CH₂CH₃ | N | CH | CH | C(OCF₃) | CH |
| 4.060 | CF₃ | —CH₂CH₃ | N | CH | CH | C(OCF₃) | CH |
| 4.061 | CF₃ | —CH₃ | N | CH | CH | C(OCF₃) | CH |
| 4.062 | H | —CH₂CH₃ | N | CH | CH | C(CF₂CF₃) | CH |
| 4.063 | CF₃ | —CH₂CH₃ | N | CH | CH | C(CF₂CF₃) | CH |
| 4.064 | CF₃ | —CH₃ | N | CH | CH | C(CF₂CF₃) | CH |
| 4.065 | H | —CH₃ | CH | N | C(CF₃) | CH | CH |
| 4.066 | CF₃ | —CH₃ | CH | N | C(CF₃) | CH | CH |
| 4.067 | OCF₃ | —CH₂CH₃ | CH | N | C(CF₃) | CH | CH |
| 4.068 | OCHF₂ | —CH₂CH₃ | CH | N | C(CF₃) | CH | CH |
| 4.069 | CF₂CF₃ | —CH₂CH₃ | CH | N | C(CF₃) | CH | CH |
| 4.070 | CF₃ | —CH₂CH₃ | CH | N | C(CN) | CH | CH |
| 4.071 | H | —CH₂CH₃ | CH | N | C(OCF₃) | CH | CH |
| 4.072 | CF₃ | —CH₂CH₃ | CH | N | C(OCF₃) | CH | CH |
| 4.073 | CF₃ | -CH₃ | CH | N | C(OCF₃) | CH | CH |
| 4.074 | H | —CH₂CH₃ | CH | N | C(CF₂CF₃) | CH | CH |
| 4.075 | CF₃ | —CH₂CH₃ | CH | N | C(CF₂CF₃) | CH | CH |
| 4.076 | CF₃ | —CH₃ | CH | N | C(CF₂CF₃) | CH | CH |
| 4.077 | H | —CH₃ | CH | N | CH | C(CF₃) | CH |
| 4.078 | CF₃ | —CH₃ | CH | N | CH | C(CF₃) | CH |
| 4.079 | OCF₃ | —CH₂CH₃ | CH | N | CH | C(CF₃) | CH |
| 4.080 | OCHF₂ | —CH₂CH₃ | CH | N | CH | C(CF₃) | CH |
| 4.081 | CF₂CF₃ | —CH₂CH₃ | CH | N | CH | C(CF₃) | CH |
| 4.082 | CF₃ | —CH₂CH₃ | CH | N | CH | C(CN) | CH |
| 4.083 | H | —CH₂CH₃ | CH | N | CH | C(OCF₃) | CH |
| 4.084 | CF₃ | —CH₂CH₃ | CH | N | CH | C(OCF₃) | CH |
| 4.085 | CF₃ | —CH₃ | CH | N | CH | C(OCF₃) | CH |
| 4.086 | H | —CH₂CH₃ | CH | N | CH | C(CF₂CF₃) | CH |
| 4.087 | CF₃ | —CH₂CH₃ | CH | N | CH | C(CF₂CF₃) | CH |
| 4.088 | CF₃ | —CH₃ | CH | N | CH | C(CF₂CF₃) | CH |
| 4.089 | CF₃ | —CH₂CH₃ | N | —OCF2O— | | CH | CH |
| 4.090 | CF₃ | —CH₂CH₃ | N | CH | —OCF2O— | | CH |
| 4.091 | CF₃ | —CH₂CH₃ | N | CH | CH | —OCF2O— | |
| 4.092 | CF₃ | —CH₂CH₃ | CH | N | —OCF2O— | | CH |
| 4.093 | CF₃ | —CH₂CH₃ | CH | N | CH | —OCF2O— | |
| 4.094 | CF₃ | —CH₂CH₃ | N | C(CF₃) | N | CH | CH |
| 4.095 | CF₃ | —CH₂CH₃ | N | CH | N | C(CF₃) | CH |
| 4.096 | CF₃ | —CH₂CH₃ | N | C(CF₃) | CH | N | CH |
| 4.097 | CF₃ | —CH₂CH₃ | N | CH | C(CF₃) | N | CH |
| 4.098 | CF₃ | —CH₂CH₃ | N | C(CF₃) | CH | CH | N |
| 4.099 | CF₃ | —CH₂CH₃ | N | CH | C(CF₃) | CH | N |
| 4.100 | CF₃ | —CH₂CH₃ | N | N | C(CF₃) | CH | CH |
| 4.101 | CF₃ | —CH₂CH₃ | N | N | CH | C(CF₃) | CH |
| 4.102 | CF₃ | —CH₂CH₃ | CH | N | C(CF₃) | N | CH |
| 4.103 | H | —CH₂CH₃ | CH | CH | C(SCF₃) | CH | CH |
| 4.104 | CF₃ | —CH₂CH₃ | CH | CH | C(SCF₃) | CH | CH |
| 4.105 | H | —CH₂CH₃ | CH | C(SCF₃) | CH | CH | CH |
| 4.106 | CF₃ | —CH₂CH₃ | CH | C(SCF₃) | CH | CH | CH |
| 4.107 | H | —CH₂CH₃ | CH | N | C(SCF₃) | CH | CH |
| 4.108 | CF₃ | —CH₂CH₃ | CH | N | C(SCF₃) | CH | CH |
| 4.109 | H | —CH₂CH₃ | N | CH | CH | C(SCF₃) | CH |
| 4.110 | CF₃ | —CH₂CH₃ | N | CH | CH | C(SCF₃) | CH |
| 4.111 | H | —CH₂CH₃ | CH | CH | C(SO₂CF₃) | CH | CH |
| 4.112 | CF₃ | —CH₂CH₃ | CH | CH | C(SO₂CF₃) | CH | CH |
| 4.113 | H | —CH₂CH₃ | CH | C(SO₂CF₃) | CH | CH | CH |
| 4.114 | CF₃ | —CH₂CH₃ | CH | C(SO₂CF₃) | CH | CH | CH |

TABLE 4-continued

| Comp. No | Ra$_2$ | R$_{12}$ | G$_1$ | G$_2$ | G$_3$ | G$_4$ | G$_5$ |
|---|---|---|---|---|---|---|---|
| 4.115 | H | —CH$_2$CH$_3$ | CH | N | C(SO$_2$CF$_3$) | CH | CH |
| 4.116 | CF$_3$ | —CH$_2$CH$_3$ | CH | N | C(SO$_2$CF$_3$) | CH | CH |
| 4.117 | H | —CH$_2$CH$_3$ | N | CH | CH | C(SO$_2$CF$_3$) | CH |
| 4.118 | CF$_3$ | —CH$_2$CH$_3$ | N | CH | CH | C(SO$_2$CF$_3$) | CH | and the N-oxides of the compounds of Table 4.

Table 5:

This table discloses the 118 compounds 5.001 to 5.118 of the formula I-2a, wherein X$_1$ is SO, and Ra$_2$, R$_{12}$, G$_1$, G$_2$, G$_3$, G$_4$ and G$_5$ are as defined in Table 4.

Table 6:

This table discloses the 118 compounds 6.001 to 6.118 of the formula I-2a, wherein X$_1$ is SO$_2$, and Ra$_1$, R$_{12}$, G$_1$, G$_2$, G$_3$, G$_4$ and G$_5$ are as defined in Table 4.

The compounds of formula I according to the invention are preventively and/or curatively valuable active ingredients in the field of pest control, even at low rates of application, which have a very favorable biocidal spectrum and are well tolerated by warm-blooded species, fish and plants. The active ingredients according to the invention act against all or individual developmental stages of normally sensitive, but also resistant, animal pests, such as insects or representatives of the order Acarina. The insecticidal or acaricidal activity of the active ingredients according to the invention can manifest itself directly, i.e. in destruction of the pests, which takes place either immediately or only after some time has elapsed, for example during ecdysis, or indirectly, for example in a reduced oviposition and/or hatching rate, a good activity corresponding to a destruction rate (mortality) of at least 50 to 60%.

Examples of the abovementioned animal pests are:

from the order Acarina, for example,

*Acalitus* spp, *Aculus* spp, *Acaricalus* spp, *Aceria* spp, *Acarus siro*, *Amblyomma* spp., *Argas* spp., *Boophilus* spp., *Brevipalpus* spp., *Bryobia* spp, *Calipitrimerus* spp., *Chorioptes* spp., *Dermanyssus gallinae*, *Dermatophagoides* spp, *Eotetranychus* spp, *Eriophyes* spp., *Hemitarsonemus* spp, *Hyalomma* spp., *Ixodes* spp., *Olygonychus* spp, *Ornithodoros* spp., *Polyphagotarsone latus*, *Panonychus* spp., *Phyllocoptruta oleivora*, *Phytonemus* spp, *Polyphagotarsonemus* spp, *Psoroptes* spp., *Rhipicephalus* spp., *Rhizoglyphus* spp., *Sarcoptes* spp., *Steneotarsonemus* spp, *Tarsonemus* spp. and *Tetranychus* spp.;

from the order Anoplura, for example,

*Haematopinus* spp., *Linognathus* spp., *Pediculus* spp., *Pemphigus* spp. and *Phylloxera* spp.;

from the order Coleoptera, for example,

*Agriotes* spp., *Amphimallon majale*, *Anomala orientalis*, *Anthonomus* spp., *Aphodius* spp, *Astylus atromaculatus*, *Ataenius* spp, *Atomaria linearis*, *Chaetocnema tibialis*, *Cerotoma* spp, *Conoderus* spp, *Cosmopolites* spp., *Cotinis nitida*, *Curculio* spp., *Cyclocephala* spp, *Dermestes* spp., *Diabrotica* spp., *Diloboderus abderus*, *Epilachna* spp., *Eremnus* spp., *Heteronychus arator*, *Hypothenemus hampei*, *Lagria vilosa*, *Leptinotarsa decemLineata*, *Lissorhoptrus* spp., *Liogenys* spp., *Maecolaspis* spp, *Maladera castanea*, *Megascelis* spp, *Melighetes aeneus*, *Melolontha* spp., *Myochrous armatus*, *Orycaephilus* spp., *Otiorhynchus* spp., *Phyllophaga* spp, *Phlyctinus* spp., *Popillia* spp, *Psylliodes* spp., *Rhyssomatus aubtilis*, *Rhizopertha* spp., *Scarabeidae*, *Sitophilus* spp., *Sitotroga* spp., *Somaticus* spp, *Sphenophorus* spp, *Sternechus subsignatus*, *Tenebrio* spp., *Tribolium* spp. and *Trogoderma* spp.;

from the order Diptera, for example,

*Aedes* spp., *Anopheles* spp, *Antherigona soccata*, *Bactrocea oleae*, *Bibio hortulanus*, *Bradysia* spp, *Calliphora erythrocephala*, *Ceratitis* spp., *Chrysomyia* spp., *Culex* spp., *Cuterebra* spp., *Dacus* spp., *Delia* spp, *Drosophila melanogaster*, *Fannia* spp., *Gastrophilus* spp., *Geomyza tripunctata*, *Glossina* spp., *Hypoderma* spp., *Hyppobosca* spp., *Liriomyza* spp., *Lucilia* spp., *Melanagromyza* spp., *Musca* spp., *Oestrus* spp., *Orseolia* spp., *Oscinella frit*, *Pegomyia hyoscyami*, *Phorbia* spp., *Rhagoletis* spp, *Rivelia quadrifasciata*, *Scatella* spp, *Sciara* spp., *Stomoxys* spp., *Tabanus* spp., *Tannia* spp. and *Tipula* spp.;

from the order Hemiptera, for example,

*Acanthocoris scabrator*, *Acrosternum* spp, *Adelphocoris lineolatus*, *Amblypelta nitida*, *Bathycoelia thalassina*, *Blissus* spp, *Cimex* spp., *Clavigralla tomentosicollis*, *Creontiades* spp, *Distantiella theobroma*, *Dichelops furcatus*, *Dysdercus* spp., *Edessa* spp, *Euchistus* spp., *Eurydema pulchrum*, *Eurygaster* spp., *Halyomorpha halys*, *Horcias nobilellus*, *Leptocorisa* spp., *Lygus* spp, *Margarodes* spp, *Murgantia histrionic*, *Neomegalotomus* spp, *Nesidiocoris tenuis*, *Nezara* spp., *Nysius simulans*, *Oebalus insularis*, *Piesma* spp., *Piezodorus* spp, *Rhodnius* spp., *Sahlbergella singularis*, *Scaptocoris castanea*, *Scotinophara* spp., *Thyanta* spp, *Triatoma* spp., *Vatiga illudens*;

*Acyrthosium pisum*, *Adalges* spp., *Agalliana ensigera*, *Agonoscena targionii*, *Aleurodicus* spp., *Aleurocanthus* spp, *Aleurolobus barodensis*, *Aleurothrixus floccosus*, *Aleyrodes brassicae*, *Amarasca biguttula*, *Amritodus atkinsoni*, *Aonidiella* spp., *Aphididae*, *Aphis* spp., *Aspidiotus* spp., *Aulacorthum solani*, *Bactericera cockerelli*, *Bemisia* spp, *Brachycaudus* spp, *Brevicoryne brassicae*, *Cacopsylla* spp, *Cavariella aegopodii* Scop., *Ceroplaster* spp., *Chrysomphalus aonidium*, *Chrysomphalus dictyospermi*, *Cicadella* spp, *Cofana spectra*, *Cryptomyzus* spp, *Cicadulina* spp, *Coccus hesperidum*, *Dalbulus maidis*, *Dialeurodes* spp, *Diaphorina citri*, *Diuraphis noxia*, *Dysaphis* spp, *Empoasca* spp., *Eriosoma larigerum*, *Erythroneura* spp., *Gascardia* spp., *Glycaspis brimblecombei*, *Hyadaphis pseudobrassicae*, *Hyalopterus* spp, *Hyperomyzus pallidus*, *Idioscopus clypealis*, *Jacobiasca lybica*, *Laodelphax* spp., *Lecanium corni*, *Lepidosaphes* spp., *Lopaphis erysimi*, *Lyogenys maidis*, *Macrosiphum* spp., *Mahanarva* spp, *Metcalfa pruinosa*, *Metopolophium dirhodum*, *Myndus crudus*, *Myzus* spp., *Neotoxoptera* sp, *Nephotettix* spp., *Nilaparvata* spp., *Nippolachnus piri* Mats, *Odonaspis ruthae*, *Oregma lanigera* Zehnter, *Parabemisia myricae*, *Paratrioza cockerelli*, *Parlatoria* spp., *Pemphigus* spp., *Peregrinus maidis*, *Perkinsiella* spp, *Phorodon humuli*, *Phylloxera* spp, *Planococcus* spp., *Pseudaulacaspis* spp., *Pseudococcus* spp., *Pseudatomoscelis seriatus*, *Psylla* spp., *Pulvinaria aethiopica*, *Quadraspidiotus* spp., *Quesada gigas*, *Recilia dorsalis*, *Rhopalosiphum* spp., *Saissetia* spp., *Scaphoideus* spp., *Schizaphis* spp., *Sitobion* spp., *Sogatella furcifera*, *Spissistilus festinus*, *Taro-*

*phagus Proserpina, Toxoptera* spp, *Trialeurodes* spp, *Tridiscus sporoboli, Trionymus* spp, *Trioza erytreae, Unaspis citri, Zygina flammigera, Zyginidia scutellaris;*
from the order Hymenoptera, for example,
*Acromyrmex, Arge* spp, *Atta* spp., *Cephus* spp., *Diprion* spp., *Diprionidae, Gilpinia polytoma, Hoplo-campa* spp., *Lasius* spp., *Monomorium pharaonis, Neodiprion* spp., *Pogonomyrmex* spp, *Slenopsis invicta, Solenopsis* spp. and *Vespa* spp.;
from the order Isoptera, for example,
*Coptotermes* spp, *Corniternes cumulans, Incisitermes* spp, *Macrotermes* spp, *Mastotermes* spp, *Microtermes* spp, *Reticulitermes* spp.; *Solenopsis geminate*
from the order Lepidoptera, for example,
*Acleris* spp., *Adoxophyes* spp., *Aegeria* spp., *Agrotis* spp., *Alabama argillaceae, Amylois* spp., *Anticarsia gemmatalis, Archips* spp., *Argyresthia* spp, *Argyrotaenia* spp., *Autographa* spp., *Bucculatrix thurberiella, Busseola fusca, Cadra cautella, Carposina nipponensis, Chilo* spp., *Choristoneura* spp., *Chrysoteuchia topiaria, Clysia ambiguella, Cnaphalocrocis* spp., *Cnephasia* spp., *Cochylis* spp., *Coleophora* spp., *Colias lesbia, Cosmophila flava, Crambus* spp, *Crocidolomia binotalis, Cryptophlebia leucotreta, Cydalima perspectalis, Cydia* spp., *Diaphania perspectalis, Diatraea* spp., *Diparopsis castanea, Earias* spp., *Eldana saccharina, Ephestia* spp., *Epinotia* spp, *Estigmene acrea, Etiella zinckinella, Eucosma* spp., *Eupoecilia ambiguella, Euproctis* spp., *Euxoa* spp., *Feltia jaculiferia, Gra-pholita* spp., *Hedya nubiferana, Heliothis* spp., *Hellula undalis, Herpetogramma* spp, *Hyphantria cunea, Keiferia lycopersicella, Lasmopalpus lignosellus, Leucoptera scitella, Lithocollethis* spp., *Lobesia botrana, Loxostege bifidalis, Lymantria* spp., *Lyonetia* spp., *Malacosoma* spp., *Mamestra brassicae, Manduca sexta, Mythimna* spp, *Noctua* spp, *Operophtera* spp., *Orniodes indica, Ostrinia nubilalis, Pammene* spp., *Pandemis* spp., *Panolis flammea, Papaipema nebris, Pectinophora gossypi-ela, Perileucoptera coffeella, Pseudaletia unipuncta, Phthorimaea operculella, Pieris rapae, Pieris* spp., *Plutella xylostella, Prays* spp., *Pseudoplusia* spp, *Rachiplusia nu, Richia albicosta, Scirpophaga* spp., *Sesamia* spp., *Sparganothis* spp., *Spodoptera* spp., *Sylepta derogate, Synanthedon* spp., *Thaumetopoea* spp., *Tortrix* spp., *Trichoplusia ni, Tuta absoluta,* and *Yponomeuta* spp.;
from the order Mallophaga, for example,
*Damalinea* spp. and *Trichodectes* spp.;
from the order Orthoptera, for example,
*Blatta* spp., *Blattella* spp., *Gryllotalpa* spp., *Leucophaea maderae, Locusta* spp., *Neocurtilla hexadactyla, Periplaneta* spp., *Scapteriscus* spp, and *Schistocerca* spp.;
from the order Psocoptera, for example,
*Liposcelis* spp.;
from the order Siphonaptera, for example,
*Ceratophyllus* spp., *Ctenocephalides* spp. and *Xenopsylla cheopis;*
from the order Thysanoptera, for example,
*Calliothrips phaseoli, Frankliniella* spp., *Heliothrips* spp, *Hercinothrips* spp., *Parthenothrips* spp, *Scirtothrips aurantii, Sericothrips variabilis, Taeniothrips* spp., *Thrips* spp;
from the order Thysanura, for example, *Lepisma saccharina.*

The active ingredients according to the invention can be used for controlling, i.e. containing or destroying, pests of the abovementioned type which occur in particular on plants, especially on useful plants and ornamentals in agriculture, in horticulture and in forests, or on organs, such as fruits, flowers, foliage, stalks, tubers or roots, of such plants, and in some cases even plant organs which are formed at a later point in time remain protected against these pests.

Suitable target crops are, in particular, cereals, such as wheat, barley, rye, oats, rice, maize or sorghum; beet, such as sugar or fodder beet; fruit, for example pomaceous fruit, stone fruit or soft fruit, such as apples, pears, plums, peaches, almonds, cherries or berries, for example strawberries, raspberries or blackberries; leguminous crops, such as beans, lentils, peas or soya; oil crops, such as oilseed rape, mustard, poppies, olives, sunflowers, coconut, castor, cocoa or ground nuts; cucurbits, such as pumpkins, cucumbers or melons; fibre plants, such as cotton, flax, hemp or jute; citrus fruit, such as oranges, lemons, grapefruit or tangerines; vegetables, such as spinach, lettuce, asparagus, cabbages, carrots, onions, tomatoes, potatoes or bell peppers; Lauraceae, such as avocado, Cinnamonium or camphor; and also tobacco, nuts, coffee, eggplants, sugarcane, tea, pepper, grapevines, hops, the plantain family, latex plants and ornamentals.

The active ingredients according to the invention are especially suitable for controlling *Aphis craccivora, Diabrotica balteata, Heliothis virescens, Myzus persicae, Plutella xylostella* and *Spodoptera littoralis* in cotton, vegetable, maize, rice and soya crops. The active ingredients according to the invention are further especially suitable for controlling *Mamestra* (preferably in vegetables), *Cydia pomonella* (preferably in apples), *Empoasca* (preferably in vegetables, vineyards), *Leptinotarsa* (preferably in potatoes) and *Chilo supressalis* (preferably in rice).

In a further aspect, the invention may also relate to a method of controlling damage to plant and parts thereof by plant parasitic nematodes (Endoparasitic-, Semiendoparasitic- and Ectoparasitic nematodes), especially plant parasitic nematodes such as root knot nematodes, *Meloidogyne hapla, Meloidogyne incognita, Meloidogyne javanica, Meloidogyne arenaria* and other *Meloidogyne* species; cyst-forming nematodes, *Globodera rostochiensis* and other *Globodera* species; *Heterodera avenae, Heterodera glycines, Heterodera schachtii, Heterodera trifolii,* and other *Heterodera* species; Seed gall nematodes, *Anguina* species; Stem and foliar nematodes, *Aphelenchoides* species; Sting nematodes, *Belonolaimus longicaudatus* and other *Belonolaimus* species; Pine nematodes, *Bursaphelenchus xylophilus* and other *Bursaphelenchus* species; Ring nematodes, *Criconema* species, *Criconemella* species, *Criconemoides* species, *Mesocriconema* species; Stem and bulb nematodes, *Ditylenchus destructor, Ditylenchus dipsaci* and other *Ditylenchus* species; Awl nematodes, *Dolichodorus* species; Spiral nematodes, *Heliocotylenchus multicinctus* and other *Helicotylenchus* species; Sheath and sheathoid nematodes, *Hemicycliophora* species and *Hemicriconemoides* species; *Hirshmanniella* species; Lance nematodes, *Hoploaimus* species; false rootknot nematodes, *Nacobbus* species; Needle nematodes, *Longidorus elongatus* and other *Longidorus* species; Pin nematodes, *Paratylenchus* species; Lesion nematodes, *Pratylenchus neglectus, Pratylenchus penetrans, Pratylenchus curvitatus, Pratylenchus goodeyi* and other *Pratylenchus* species; Burrowing nematodes, *Radopholus similis* and other *Radopholus* species; Reniform nematodes, *Rotylenchus robustus, Rotylenchus reniformis* and other *Rotylenchus* species; *Scutellonema* species; Stubby root nematodes, *Trichodorus primitivus* and other *Trichodorus* species, *Paratrichodorus* species; Stunt nematodes, *Tylenchorhynchus claytoni, Tylenchorhynchus dubius* and other *Tylenchorhynchus* species; Citrus nematodes, *Tylenchulus* species; Dagger nematodes, *Xiphinema* species; and other plant parasitic nematode species, such as *Subanguina* spp.,

*Hypsoperine* spp., *Macroposthonia* spp., *Melinius* spp., *Punctodera* spp., and *Quinisulcius* spp.

The compounds of the invention may also have activity against the molluscs. Examples of which include, for example, Ampullariidae; *Arion* (*A. ater, A. circumscriptus, A. hortensis, A. rufus*); Bradybaenidae (*Bradybaena fruticum*); *Cepaea* (*C. hortensis, C. Nemoralis*); *ochlodina; Deroceras* (*D. agrestis, D. empiricorum, D. laeve, D. reticulatum*); *Discus* (*D. rotundatus*); *Euomphalia; Galba* (*G. trunculata*); *Helicelia* (*H. itala, H. obvia*); Helicidae *Helicigona arbustorum*); *Helicodiscus; Helix* (*H. aperta*); *Limax* (*L. cinereoniger, L. flavus, L. marginatus, L. maximus, L. tenellus*); *Lymnaea; Milax* (*M. gagates, M. marginatus, M. sowerbyi*); *Opeas; Pomacea* (*P. canaticulata*); *Vallonia* and *Zanitoides*.

The term "crops" is to be understood as including also crop plants which have been so transformed by the use of recombinant DNA techniques that they are capable of synthesising one or more selectively acting toxins, such as are known, for example, from toxin-producing bacteria, especially those of the genus *Bacillus*.

Toxins that can be expressed by such transgenic plants include, for example, insecticidal proteins, for example insecticidal proteins from *Bacillus cereus* or *Bacillus popilliae*; or insecticidal proteins from *Bacillus thuringiensis*, such as δ-endotoxins, e.g. Cry1Ab, Cry1Ac, Cry1F, Cry1Fa2, Cry2Ab, Cry3A, Cry3Bb1 or Cry9C, or vegetative insecticidal proteins (Vip), e.g. Vip1, Vip2, Vip3 or Vip3A; or insecticidal proteins of bacteria colonising nematodes, for example *Photorhabdus* spp. or *Xenorhabdus* spp., such as *Photorhabdus luminescens, Xenorhabdus nematophilus*; toxins produced by animals, such as scorpion toxins, arachnid toxins, wasp toxins and other insect-specific neurotoxins; toxins produced by fungi, such as *Streptomycetes* toxins, plant lectins, such as pea lectins, barley lectins or snowdrop lectins; agglutinins; proteinase inhibitors, such as trypsin inhibitors, serine protease inhibitors, patatin, cystatin, papain inhibitors; ribosome-inactivating proteins (RIP), such as ricin, maize-RIP, abrin, luffin, saporin or bryodin; steroid metabolism enzymes, such as 3-hydroxysteroidoxidase, ecdysteroid-UDP-glycosyl-transferase, cholesterol oxidases, ecdysone inhibitors, HMG-COA-reductase, ion channel blockers, such as blockers of sodium or calcium channels, juvenile hormone esterase, diuretic hormone receptors, stilbene synthase, bibenzyl synthase, chitinases and glucanases.

In the context of the present invention there are to be understood by δ-endotoxins, for example Cry1Ab, Cry1Ac, Cry1F, Cry1Fa2, Cry2Ab, Cry3A, Cry3Bb1 or Cry9C, or vegetative insecticidal proteins (Vip), for example Vip1, Vip2, Vip3 or Vip3A, expressly also hybrid toxins, truncated toxins and modified toxins. Hybrid toxins are produced recombinantly by a new combination of different domains of those proteins (see, for example, WO 02/15701). Truncated toxins, for example a truncated Cry1Ab, are known. In the case of modified toxins, one or more amino acids of the naturally occurring toxin are replaced. In such amino acid replacements, preferably non-naturally present protease recognition sequences are inserted into the toxin, such as, for example, in the case of Cry3A055, a cathepsin-G-recognition sequence is inserted into a Cry3A toxin (see WO 03/018810). Examples of such toxins or transgenic plants capable of synthesising such toxins are disclosed, for example, in EP-A-0 374 753, WO 93/07278, WO 95/34656, EP-A-0 427 529, EP-A-451 878 and WO 03/052073.

The processes for the preparation of such transgenic plants are generally known to the person skilled in the art and are described, for example, in the publications mentioned above. Cry1-type deoxyribonucleic acids and their preparation are known, for example, from WO 95/34656, EP-A-0 367 474, EP-A-0 401 979 and WO 90/13651.

The toxin contained in the transgenic plants imparts to the plants tolerance to harmful insects. Such insects can occur in any taxonomic group of insects, but are especially commonly found in the beetles (Coleoptera), two-winged insects (Diptera) and moths (Lepidoptera).

Transgenic plants containing one or more genes that code for an insecticidal resistance and express one or more toxins are known and some of them are commercially available. Examples of such plants are: YieldGard® (maize variety that expresses a Cry1Ab toxin); YieldGard Rootworm® (maize variety that expresses a Cry3Bb1 toxin); YieldGard Plus® (maize variety that expresses a Cry1Ab and a Cry3Bb1 toxin); Starlink® (maize variety that expresses a Cry9C toxin); Herculex I® (maize variety that expresses a Cry1Fa2 toxin and the enzyme phosphinothricine N-acetyltransferase (PAT) to achieve tolerance to the herbicide glufosinate ammonium); NuCOTN 33B® (cotton variety that expresses a Cry1Ac toxin); Bollgard I® (cotton variety that expresses a Cry1Ac toxin); Bollgard I® (cotton variety that expresses a Cry1Ac and a Cry2Ab toxin); VipCot® (cotton variety that expresses a Vip3A and a Cry1Ab toxin); NewLeaf® (potato variety that expresses a Cry3A toxin); NatureGard®, Agrisure® GT Advantage (GA21 glyphosate-tolerant trait), Agrisure® CB Advantage (Bt11 corn borer (CB) trait) and Protecta®.

Further examples of such transgenic crops are:
1. Bt11 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a truncated Cry1Ab toxin. Bt11 maize also transgenically expresses the enzyme PAT to achieve tolerance to the herbicide glufosinate ammonium.
2. Bt176 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a Cry1Ab toxin. Bt176 maize also transgenically expresses the enzyme PAT to achieve tolerance to the herbicide glufosinate ammonium.
3. MIR604 Maize from Syngenta Seeds SAS, Chemin de l'Hobit 27, F-31 790 St. Sauveur, France, registration number C/FR/96/05/10. Maize which has been rendered insect-resistant by transgenic expression of a modified Cry3A toxin. This toxin is Cry3A055 modified by insertion of a cathepsin-G-protease recognition sequence. The preparation of such transgenic maize plants is described in WO 03/018810.
4. MON 863 Maize from Monsanto Europe S.A. 270-272 Avenue de Tervuren, B-1150 Brussels, Belgium, registration number C/DE/02/9. MON 863 expresses a Cry3Bb1 toxin and has resistance to certain Coleoptera insects.
5. IPC 531 Cotton from Monsanto Europe S.A. 270-272 Avenue de Tervuren, B-1150 Brussels, Belgium, registration number C/ES/96/02.
6. 1507 Maize from Pioneer Overseas Corporation, Avenue Tedesco, 7 B-1160 Brussels, Belgium, registration number C/NL/00/10. Genetically modified maize for the expression of the protein Cry1F for achieving resistance to certain Lepidoptera insects and of the PAT protein for achieving tolerance to the herbicide glufosinate ammonium.

7. NK603×MON 810 Maize from Monsanto Europe S.A. 270-272 Avenue de Tervuren, B-1150 Brussels, Belgium, registration number C/GB/02/M3/03. Consists of conventionally bred hybrid maize varieties by crossing the genetically modified varieties NK603 and MON 810. NK603× MON 810 Maize transgenically expresses the protein CP4 EPSPS, obtained from *Agrobacterium* sp. strain CP4, which imparts tolerance to the herbicide Roundup® (contains glyphosate), and also a Cry1Ab toxin obtained from *Bacillus thuringiensis* subsp. *kurstaki* which brings about tolerance to certain Lepidoptera, include the European corn borer.

Transgenic crops of insect-resistant plants are also described in BATS (Zentrum für Biosicherheit and Nachhaltigkeit, Zentrum BATS, Clarastrasse 13, 4058 Basel, Switzerland) Report 2003, (http://bats.ch).

The term "crops" is to be understood as including also crop plants which have been so transformed by the use of recombinant DNA techniques that they are capable of synthesising antipathogenic substances having a selective action, such as, for example, the so-called "pathogenesis-related proteins" (PRPs, see e.g. EP-A-0 392 225). Examples of such antipathogenic substances and transgenic plants capable of synthesising such antipathogenic substances are known, for example, from EP-A-0 392 225, WO 95/33818 and EP-A-0 353 191. The methods of producing such transgenic plants are generally known to the person skilled in the art and are described, for example, in the publications mentioned above.

Antipathogenic substances which can be expressed by such transgenic plants include, for example, ion channel blockers, such as blockers for sodium and calcium channels, for example the viral KP1, KP4 or KP6 toxins; stilbene synthases; bibenzyl synthases; chitinases; glucanases; the so-called "pathogenesis-related proteins" (PRPs; see e.g. EP-A-0 392 225); antipathogenic substances produced by microorganisms, for example peptide antibiotics or heterocyclic antibiotics (see e.g. WO 95/33818) or protein or polypeptide factors involved in plant pathogen defence (so-called "plant disease resistance genes", as described in WO 03/000906).

Further areas of use of the compositions according to the invention are the protection of stored goods and store rooms and the protection of raw materials, such as wood, textiles, floor coverings or buildings, and also in the hygiene sector, especially the protection of humans, domestic animals and productive livestock against pests of the mentioned type.

The present invention also provides a method for controlling pests (such as mosquitoes and other disease vectors; see also http://www.who.int/malaria/vector_control/irs/en/). In one embodiment, the method for controlling pests comprises applying the compositions of the invention to the target pests, to their locus or to a surface or substrate by brushing, rolling, spraying, spreading or dipping. By way of example, an IRS (indoor residual spraying) application of a surface such as a wall, ceiling or floor surface is contemplated by the method of the invention. In another embodiment, it is contemplated to apply such compositions to a substrate such as non-woven or a fabric material in the form of (or which can be used in the manufacture of) netting, clothing, bedding, curtains and tents.

In one embodiment, the method for controlling such pests comprises applying a pesticidally effective amount of the compositions of the invention to the target pests, to their locus, or to a surface or substrate so as to provide effective residual pesticidal activity on the surface or substrate. Such application may be made by brushing, rolling, spraying, spreading or dipping the pesticidal composition of the invention. By way of example, an IRS application of a surface such as a wall, ceiling or floor surface is contemplated by the method of the invention so as to provide effective residual pesticidal activity on the surface. In another embodiment, it is contemplated to apply such compositions for residual control of pests on a substrate such as a fabric material in the form of (or which can be used in the manufacture of) netting, clothing, bedding, curtains and tents.

Substrates including non-woven, fabrics or netting to be treated may be made of natural fibres such as cotton, raffia, jute, flax, sisal, hessian, or wool, or synthetic fibres such as polyamide, polyester, polypropylene, polyacrylonitrile or the like. The polyesters are particularly suitable. The methods of textile treatment are known, e.g. WO 2008/151984, WO 2003/034823, U.S. Pat. No. 5,631,072, WO 2005/64072, WO2006/128870, EP 1724392, WO2005113886 or WO 2007/090739.

Further areas of use of the compositions according to the invention are the field of tree injection/trunk treatment for all ornamental trees as well all sort of fruit and nut trees.

In the field of tree injection/trunk treatment, the compounds according to the present invention are especially suitable against wood-boring insects from the order Lepidoptera as mentioned above and from the order Coleoptera, especially against woodborers listed in the following tables A and B:

TABLE A

Examples of exotic woodborers of economic importance.

| Family | Species | Host or Crop Infested |
| --- | --- | --- |
| Buprestidae | *Agrilus planipennis* | Ash |
| Cerambycidae | *Anoplura glabripennis* | Hardwoods |
| Scolytidae | *Xylosandrus crassiusculus* | Hardwoods |
|  | *X. mutilatus* | Hardwoods |
|  | *Tomicus piniperda* | Conifers |

TABLE B

Examples of native woodborers of economic importance.

| Family | Species | Host or Crop Infested |
| --- | --- | --- |
| Buprestidae | *Agrilus anxius* | Birch |
|  | *Agrilus politus* | Willow, Maple |
|  | *Agrilus sayi* | Bayberry, Sweetfern |
|  | *Agrilus vittaticolllis* | Apple, Pear, Cranberry, Serviceberry, Hawthorn |
|  | *Chrysobothris femorata* | Apple, Apricot, Beech, Boxelder, Cherry, Chestnut, Currant, Elm, Hawthorn, Hackberry, Hickory, Horsechestnut, Linden, Maple, |

TABLE B-continued

Examples of native woodborers of economic importance.

| Family | Species | Host or Crop Infested |
| --- | --- | --- |
| | | Mountain-ash, Oak, Pecan, Pear, Peach, Persimmon, Plum, Poplar, Quince, Redbud, Serviceberry, Sycamore, Walnut, Willow |
| | Texania campestris | Basswood, Beech, Maple, Oak, Sycamore, Willow, Yellow-poplar |
| Cerambycidae | Goes pulverulentus | Beech, Elm, Nuttall, Willow, Black oak, Cherrybark oak, Water oak, Sycamore |
| | Goes tigrinus | Oak |
| | Neoclytus acuminatus | Ash, Hickory, Oak, Walnut, Birch, Beech, Maple, Eastern hophornbeam, Dogwood, Persimmon, Redbud, Holly, Hackberry, Black locust, Honeylocust, Yellow-poplar, Chestnut, Osage-orange, Sassafras, Lilac, Mountain-mahogany, Pear, Cherry, Plum, Peach, Apple, Elm, Basswood, Sweetgum |
| | Neoptychodes trilineatus | Fig, Alder, Mulberry, Willow, Netleaf hackberry |
| | Oberea ocellata | Sumac, Apple, Peach, Plum, Pear, Currant, Blackberry |
| | Oberea tripunctata | Dogwood, Viburnum, Elm, Sourwood, Blueberry, Rhododendron, Azalea, Laurel, Poplar, Willow, Mulberry |
| | Oncideres cingulata | Hickory, Pecan, Persimmon, Elm, Sourwood, Basswood, Honeylocust, Dogwood, Eucalyptus, Oak, Hackberry, Maple, Fruit trees |
| | Saperda calcarata | Poplar |
| | Strophiona nitens | Chestnut, Oak, Hickory, Walnut, Beech, Maple |
| Scolytidae | Corthylus columbianus | Maple, Oak, Yellow-poplar, Beech, Boxelder, Sycamore, Birch, Basswood, Chestnut, Elm |
| | Dendroctonus frontalis | Pine |
| | Dryocoetes betulae | Birch, Sweetgum, Wild cherry, Beech, Pear |
| | Monarthrum fasciatum | Oak, Maple, Birch, Chestnut, Sweetgum, Blackgum, Poplar, Hickory, Mimosa, Apple, Peach, Pine |
| | Phloeotribus liminaris | Peach, Cherry, Plum, Black cherry, Elm, Mulberry, Mountain-ash |
| | Pseudopityophthorus pruinosus | Oak, American beech, Black cherry, Chickasaw plum, Chestnut, Maple, Hickory, Hornbeam, Hophornbeam |
| Sesiidae | Paranthrene simulans | Oak, American chestnut |
| | Sannina uroceriformis | Persimmon |
| | Synanthedon exitiosa | Peach, Plum, Nectarine, Cherry, Apricot, Almond, Black cherry |
| | Synanthedon pictipes | Peach, Plum, Cherry, Beach, Black Cherry |
| | Synanthedon rubrofascia | Tupelo |
| | Synanthedon scitula | Dogwood, Pecan, Hickory, Oak, Chestnut, Beech, Birch, Black cherry, Elm, Mountain-ash, Viburnum, Willow, Apple, Loquat, Ninebark, Bayberry |
| | Vitacea polistiformis | Grape |

The present invention may be also used to control any insect pests that may be present in turfgrass, including for example beetles, caterpillars, fire ants, ground pearls, millipedes, sow bugs, mites, mole crickets, scales, mealybugs ticks, spittlebugs, southern chinch bugs and white grubs. The present invention may be used to control insect pests at various stages of their life cycle, including eggs, larvae, nymphs and adults.

In particular, the present invention may be used to control insect pests that feed on the roots of turfgrass including white grubs (such as *Cyclocephala* spp. (e.g. masked chafer, *C. lurida*), *Rhizotrogus* spp. (e.g. European chafer, *R. majalis*), *Cotinus* spp. (e.g. Green June beetle, *C. nitida*), *Popillia* spp. (e.g. Japanese beetle, *P. japonica*), *Phyllophaga* spp. (e.g. May/June beetle), *Ataenius* spp. (e.g. Black turfgrass *ataenius, A. spretulus*), *Maladera* spp. (e.g. Asiatic garden beetle, *M. castanea*) and *Tomarus* spp.), ground pearls (*Margarodes* spp.), mole crickets (tawny, southern, and short-winged; *Scapteriscus* spp., *Gryllotalpa africana*) and leatherjackets (European crane fly, *Tipula* spp.).

The present invention may also be used to control insect pests of turfgrass that are thatch dwelling, including armyworms (such as fall armyworm *Spodoptera frugiperda*, and common armyworm *Pseudaletia unipuncta*), cutworms, billbugs (*Sphenophorus* spp., such as *S. venatus verstitus* and *S. parvulus*), and sod webworms (such as *Crambus* spp. and the tropical sod webworm, *Herpetogramma phaeopteralis*).

The present invention may also be used to control insect pests of turfgrass that live above the ground and feed on the turfgrass leaves, including chinch bugs (such as southern chinch bugs, *Blissus insularis*), Bermudagrass mite (*Eriophyes cynodoniensis*), rhodesgrass mealybug (*Antonina graminis*), two-lined spittlebug (*Propsapia bicincta*), leafhoppers, cutworms (Noctuidae family), and greenbugs. The present invention may also be used to control other pests of turfgrass such as red imported fire ants (*Solenopsis invicta*) that create ant mounds in turf.

In the hygiene sector, the compositions according to the invention are active against ectoparasites such as hard ticks, soft ticks, mange mites, harvest mites, flies (biting and licking), parasitic fly larvae, lice, hair lice, bird lice and fleas.

Examples of such parasites are:

Of the order Anoplurida: *Haematopinus* spp., *Linognathus* spp., *Pediculus* spp. and *Phtirus* spp., *Solenopotes* spp.

Of the order Mallophagida: *Trimenopon* spp., *Menopon* spp., *Trinoton* spp., *Bovicola* spp., *Werneckiella* spp., *Lepikentron* spp., *Damalina* spp., *Trichodectes* spp. and *Felicola* spp.

Of the order Diptera and the suborders Nematocerina and Brachycerina, for example *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp. and *Melophagus* spp.

Of the order Siphonapterida, for example *Pulex* spp., *Ctenocephalides* spp., *Xenopsylla* spp., *Ceratophyllus* spp.

Of the order Heteropterida, for example *Cimex* spp., *Triatoma* spp., *Rhodnius* spp., *Panstrongylus* spp.

Of the order Blattarida, for example *Blatta orientalis, Periplaneta americana, Blattelagermanica* and *Supella* spp.

Of the subclass Acaria (Acarida) and the orders Meta- and Meso-stigmata, for example *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Sternostoma* spp. and *Varroa* spp.

Of the orders Actinedida (Prostigmata) and Acaridida (Astigmata), for example *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp. and *Laminosioptes* spp.

The compositions according to the invention are also suitable for protecting against insect infestation in the case of materials such as wood, textiles, plastics, adhesives, glues, paints, paper and card, leather, floor coverings and buildings.

The compositions according to the invention can be used, for example, against the following pests: beetles such as *Hylotrupes bajulus, Chlorophorus pilosis, Anobium punctatum, Xestobium rufovillosum, Ptilinuspecticornis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthesrugicollis, Xyleborus* spec., *Tryptodendron* spec., *Apate monachus, Bostrychus capucins, Heterobostrychus brunneus, Sinoxylon* spec. and *Dinoderus minutus*, and also hymenopterans such as *Sirex juvencus, Urocerus gigas, Urocerus gigas taignus* and *Urocerus augur*, and termites such as *Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis* and *Coptotermes formosanus*, and bristletails such as *Lepisma saccharina*.

The invention therefore also relates to pesticidal compositions such as emulsifiable concentrates, suspension concentrates, microemulsions, oil dispersibles, directly sprayable or dilutable solutions, spreadable pastes, dilute emulsions, soluble powders, dispersible powders, wettable powders, dusts, granules or encapsulations in polymeric substances, which comprise—at least—one of the active ingredients according to the invention and which are to be selected to suit the intended aims and the prevailing circumstances.

In these compositions, the active ingredient is employed in pure form, a solid active ingredient for example in a specific particle size, or, preferably, together with—at least—one of the auxiliaries conventionally used in the art of formulation, such as extenders, for example solvents or solid carriers, or such as surface-active compounds (surfactants).

Examples of suitable solvents are: unhydrogenated or partially hydrogenated aromatic hydrocarbons, preferably the fractions $C_8$ to $C_{12}$ of alkylbenzenes, such as xylene mixtures, alkylated naphthalenes or tetrahydronaphthalene, aliphatic or cycloaliphatic hydrocarbons, such as paraffins or cyclohexane, alcohols such as ethanol, propanol or butanol, glycols and their ethers and esters such as propylene glycol, dipropylene glycol ether, ethylene glycol or ethylene glycol monomethyl ether or ethylene glycol monoethyl ether, ketones, such as cyclohexanone, isophorone or diacetone alcohol, strongly polar solvents, such as N-methylpyrrolid-2-one, dimethyl sulfoxide or N,N-dimethylformamide, water, unepoxidized or epoxidized vegetable oils, such as unexpodized or epoxidized rapeseed, castor, coconut or soya oil, and silicone oils.

Solid carriers which are used for example for dusts and dispersible powders are, as a rule, ground natural minerals such as calcite, talc, kaolin, montmorillonite or attapulgite. To improve the physical properties, it is also possible to add highly disperse silicas or highly disperse absorbtive polymers. Suitable adsorptive carriers for granules are porous types, such as pumice, brick grit, sepiolite or bentonite, and suitable non-sorptive carrier materials are calcite or sand. In addition, a large number of granulated materials of inorganic or organic nature can be used, in particular dolomite or comminuted plant residues.

Suitable surface-active compounds are, depending on the type of the active ingredient to be formulated, non-ionic, cationic and/or anionic surfactants or surfactant mixtures which have good emulsifying, dispersing and wetting properties. The surfactants mentioned below are only to be considered as examples; a large number of further surfactants which are conventionally used in the art of formulation and suitable according to the invention are described in the relevant literature.

Suitable non-ionic surfactants are, especially, polyglycol ether derivatives of aliphatic or cycloaliphatic alcohols, of saturated or unsaturated fatty acids or of alkyl phenols which may contain approximately 3 to approximately 30 glycol ether groups and approximately 8 to approximately 20 carbon atoms in the (cyclo)aliphatic hydrocarbon radical or approximately 6 to approximately 18 carbon atoms in the alkyl moiety of the alkyl phenols. Also suitable are water-soluble polyethylene oxide adducts with polypropylene glycol, ethylenediaminopolypropylene glycol or alkyl polypropylene glycol having 1 to approximately 10 carbon atoms in the alkyl chain and approximately 20 to approximately 250 ethylene glycol ether groups and approximately 10 to approximately 100 propylene glycol ether groups. Normally, the abovementioned compounds contain 1 to approximately 5 ethylene glycol units per propylene glycol unit. Examples which may be mentioned are nonylphenoxypolyethoxyethanol, castor oil polyglycol ether, polypropylene glycol/polyethylene oxide adducts, tributylpheno-xypolyethoxyethanol, polyethylene glycol or octylphenoxypolyethoxyethanol. Also suitable are fatty acid esters of polyoxyethylene sorbitan, such as polyoxyethylene sorbitan trioleate.

The cationic surfactants are, especially, quarternary ammonium salts which generally have at least one alkyl radical of approximately 8 to approximately 22 C atoms as substituents and as further substituents (unhalogenated or halogenated) lower alkyl or hydroxyalkyl or benzyl radicals. The salts are preferably in the form of halides, methylsulfates or ethylsulfates. Examples are stearyltrimethylammonium chloride and benzylbis(2-chloroethyl)ethylammonium bromide. Examples of suitable anionic surfactants are water-soluble soaps or water-soluble synthetic surface-active compounds. Examples of suitable soaps are the alkali, alkaline earth or (unsubstituted or substituted) ammonium salts of fatty acids having approximately 10 to approximately 22 C atoms, such as the sodium or potassium salts of oleic or stearic acid, or of natural fatty acid mixtures which are obtainable for example from coconut or tall oil; mention must also be made of the fatty acid methyl taurates. However, synthetic surfactants are used more frequently, in particular fatty sulfonates, fatty sulfates, sulfonated benzimidazole derivatives or alkylaryl sulfonates. As a rule, the fatty sulfonates and fatty sulfates are present as alkali, alkaline earth or (substituted or unsubstituted) ammonium salts and they generally have an alkyl radical of approximately 8 to approximately 22 C atoms, alkyl also to be understood as including the alkyl moiety of acyl radicals; examples which may be mentioned are the sodium or calcium salts of lignosulfonic acid, of the dodecylsulfuric ester or of a fatty alcohol sulfate mixture prepared from natural fatty acids. This group also includes the salts of the sulfuric esters and sulfonic acids of fatty alcohol/ethylene oxide adducts. The sulfonated benzimidazole derivatives preferably contain 2 sulfonyl groups and a fatty acid radical of approximately 8 to approximately 22 C atoms. Examples of alkylarylsulfonates are the sodium, calcium or triethanolammonium salts of decylbenzenesulfonic acid, of dibutylnaphthalenesulfonic acid or of a naphthalenesulfonic acid/formaldehyde condensate. Also possible are, furthermore, suitable phosphates, such as salts of the phosphoric ester of a p-nonylphenol/(4-14)ethylene oxide adduct, or phospholipids.

As a rule, the compositions comprise 0.1 to 99%, especially 0.1 to 95%, of active ingredient and 1 to 99.9%, especially 5 to 99.9%, of at least one solid or liquid adjuvant, it being possible as a rule for 0 to 25%, especially 0.1 to 20%, of the composition to be surfactants (% in each case meaning percent by weight). Whereas concentrated compositions tend to be preferred for commercial goods, the end consumer as a rule uses dilute compositions which have substantially lower concentrations of active ingredient.

Typically, a pre-mix formulation for foliar application comprises 0.1 to 99.9%, especially 1 to 95%, of the desired ingredients, and 99.9 to 0.1%, especially 99 to 5%, of a solid or liquid adjuvant (including, for example, a solvent such as water), where the auxiliaries can be a surfactant in an amount of 0 to 50%, especially 0.5 to 40%, based on the pre-mix formulation.

Normally, a tank-mix formulation for seed treatment application comprises 0.25 to 80%, especially 1 to 75%, of the desired ingredients, and 99.75 to 20%, especially 99 to 25%, of a solid or liquid auxiliaries (including, for example, a solvent such as water), where the auxiliaries can be a surfactant in an amount of 0 to 40%, especially 0.5 to 30%, based on the tank-mix formulation.

Typically, a pre-mix formulation for seed treatment application comprises 0.5 to 99.9%, especially 1 to 95%, of the desired ingredients, and 99.5 to 0.1%, especially 99 to 5%, of a solid or liquid adjuvant (including, for example, a solvent such as water), where the auxiliaries can be a surfactant in an amount of 0 to 50%, especially 0.5 to 40%, based on the pre-mix formulation.

Whereas commercial products will preferably be formulated as concentrates (e.g., pre-mix composition (formulation)), the end user will normally employ dilute formulations (e.g., tank mix composition).

Preferred seed treatment pre-mix formulations are aqueous suspension concentrates. The formulation can be applied to the seeds using conventional treating techniques and machines, such as fluidized bed techniques, the roller mill method, rotostatic seed treaters, and drum coaters. Other methods, such as spouted beds may also be useful. The seeds may be presized before coating. After coating, the seeds are typically dried and then transferred to a sizing machine for sizing. Such procedures are known in the art.

In general, the pre-mix compositions of the invention contain 0.5 to 99.9 especially 1 to 95, advantageously 1 to 50%, by mass of the desired ingredients, and 99.5 to 0.1, especially 99 to 5%, by mass of a solid or liquid adjuvant (including, for example, a solvent such as water), where the auxiliaries (or adjuvant) can be a surfactant in an amount of 0 to 50, especially 0.5 to 40%, by mass based on the mass of the pre-mix formulation.

Examples of foliar formulation types for pre-mix compositions are:
GR: Granules
WP: wettable powders
WG: water dispersable granules (powders)
SG: water soluble granules
SL: soluble concentrates
EC: emulsifiable concentrate
EW: emulsions, oil in water
ME: micro-emulsion
SC: aqueous suspension concentrate
CS: aqueous capsule suspension
OD: oil-based suspension concentrate, and
SE: aqueous suspo-emulsion.

Whereas, examples of seed treatment formulation types for pre-mix compositions are:
WS: wettable powders for seed treatment slurry
LS: solution for seed treatment ES: emulsions for seed treatment
FS: suspension concentrate for seed treatment
WG: water dispersible granules, and
CS: aqueous capsule suspension.

Examples of formulation types suitable for tank-mix compositions are solutions, dilute emulsions, suspensions, or a mixture thereof, and dusts.

Preferred compositions are composed in particular as follows (%=percent by weight):
Emulsifiable Concentrates:
active ingredient: 1 to 95%, preferably 5 to 20%
surfactant: 1 to 30%, preferably 10 to 20%
solvent: 5 to 98%, preferably 70 to 85%
Dusts:
active ingredient: 0.1 to 10%, preferably 0.1 to 1%
solid carrier: 99.9 to 90%, preferably 99.9 to 99%
Suspension Concentrates:
active ingredient: 5 to 75%, preferably 10 to 50%
water: 94 to 24%, preferably 88 to 30%
surfactant: 1 to 40%, preferably 2 to 30%
Wettable Powders:
active ingredient: 0.5 to 90%, preferably 1 to 80%
surfactant: 0.5 to 20%, preferably 1 to 15%
solid carrier: 5 to 99%, preferably 15 to 98%
Granulates:
active ingredient: 0.5 to 30%, preferably 3 to 15%
solid carrier: 99.5 to 70%, preferably 97 to 85%

PREPARATORY EXAMPLES

"Mp" means melting point in ° C. Free radicals represent methyl groups. $^1$H NMR measurements were recorded on a Brucker 400 MHz spectrometer, chemical shifts are given in ppm relevant to a TMS standard. Spectra measured in deuterated solvents as indicated. Common abbreviations: aq=aqueous, min=minute, h=hour, sat=saturated, $R_t$=retention time, mCPBA=meta-chloroperoxybenzoic acid, MeOH=methanol, NaHCO$_3$=sodium hydrogen carbonate, Na$_2$CO$_3$=sodium carbonate, HCl=hydrogen chloride, NBS=N-bromosuccinimide, PdCl$_2$(dppf)=[1,1-bis (diphenylphosphino)ferrocene]dichloropalladium(II).
LCMS Methods:
Method 1:

SC_BASE, Apparatus: Agilent 1100 Bin. Pump: G1312A, degasser; autosampler, ColCom, DAD: Agilent G1315B, 220-320 nm, MSD: Agilent LC/MSD G6130B ESI, pos/neg 100-800; ELSD PL-ELS2100 gas flow 1.1 ml/min, gas temp: 50° C.; column: Waters XSelect™ C18, 30×2.1 mm, 3.5μ, Temp: 25° C., Flow: 1 mL/min, Gradient: $t_0$=2% A, $t_{1.6\ min}$=98% A, $t_{3\ min}$=98% A, Posttime: 1.3 min, Eluent A: 95% acetonitrile+5% 10 mM ammonium bicarbonate in water in acetonitrile, Eluent B: 10 mM ammonium bicarbonate in water (pH=9.5).
Method 2:

AN_BASE, Apparatus: Agilent 1100 Bin. Pump: G1312A, degasser; autosampler, ColCom, DAD: Agilent G1315B, 220-320 nm, MSD: Agilent LC/MSD G6130B ESI, pos/neg 100-800; ELSD PL-ELS2100 gas flow 1.1 ml/min, gas temp: 50° C.; column: Waters XSelect™ C18, 50×2.1 mm, 3.5μ, Temp: 25° C., Flow: 0.8 mL/min, Gradient: $t_0$=2% A, $t_{3.5\ min}$=98% A, $t_{6\ min}$=98% A, Posttime: 2 min, Eluent A: 95% acetonitrile+5% 10 mM ammonium bicarbonate in water in acetonitrile, Eluent B: 10 mM ammonium bicarbonate in water (pH=9.5).
Method 3:

Spectra were recorded on a Mass Spectrometer from Waters (SQD or ZQ Single quadrupole mass spectrometer) equipped with an electrospray source (Polarity: positive or negative ions, Capillary: 3.00 kV, Cone range: 30-60 V, Extractor: 2.00 V, Source Temperature: 150° C., Desolvation Temperature: 350° C., Cone Gas Flow: 0 L/Hr, Desolvation Gas Flow: 650 L/Hr, Mass range: 100 to 900 Da) and an Acquity UPLC from Waters: Binary pump, heated column compartment and diode-array detector. Solvent degasser, binary pump, heated column compartment and diode-array detector. Column: Waters UPLC HSS T3, 1.8 μm, 30×2.1 mm, Temp: 60° C., DAD Wavelength range (nm): 210 to 500, Solvent Gradient: A=water+5% MeOH+0.05% HCOOH, B=Acetonitrile+0.05% HCOOH; gradient: 0 min 0% B, 100% A; 2.7-3.0 min 100% B; Flow (ml/min) 0.85.
Method 4:

Spectra were recorded on a Mass Spectrometer from Waters (SQD, SODII or ZQ Single quadrupole mass spectrometer) equipped with an electrospray source (Polarity: positive or negative ions, Capillary: 3.00 kV, Cone range: 30-60 V, Extractor: 2.00 V, Source Temperature: 150° C., Desolvation Temperature: 350° C., Cone Gas Flow: 0 L/Hr, Desolvation Gas Flow: 650 L/Hr, Mass range: 100 to 900 Da) and an Acquity UPLC from Waters: Binary pump, heated column compartment and diode-array detector. Solvent degasser, binary pump, heated column compartment and diode-array detector. Column: Waters UPLC HSS T3, 1.8 mm, 30×2.1 mm, Temp: 60° C., DAD Wavelength range (nm): 210 to 500, Solvent Gradient: A=water+5% MeOH+0.05% HCOOH, B=Acetonitrile+0.05% HCOOH; gradient: 10-100% B in 1.2 min; Flow (ml/min) 0.85.
Method 5:

Spectra were recorded on an ACQUITY SQD Mass Spectrometer from Waters (Single quadrupole mass spectrometer). Ionisation method: Electrospray. Polarity: positive ions. Capillary (kV) 3.00, Cone (V) 20.00, Extractor (V) 3.00, Source Temperature (° C.) 150, Desolvation Temperature (° C.) 400, Cone Gas Flow (L/Hr) 60, Desolvation Gas Flow (L/Hr) 700; Mass range: 100 to 800 Da; DAD Wavelength range (nm): 210 to 400.

Method Waters ACQUITY UPLC with the following HPLC gradient conditions (Solvent A: Water/Methanol 9:1, 0.1% formic acid and Solvent B: Acetonitrile, 0.1% formic acid)

| Time (minutes) | A (%) | B (%) | Flow rate (ml/min) |
| --- | --- | --- | --- |
| 0 | 100 | 0 | 0.75 |
| 2.5 | 0 | 100 | 0.75 |
| 2.8 | 0 | 100 | 0.75 |
| 3.0 | 100 | 0 | 0.75 |

Type of column: Waters ACQUITY UPLC HSS T3; Column length: 30 mm; Internal diameter of column: 2.1 mm; Particle Size: 1.8 micron; Temperature: 60° C.

Example P1: Preparation of 3-ethylsulfonyl-2-[1-methyl-5-[3-(trifluoromethyl)phenyl] imidazol-2-yl]-5-(trifluoromethyl)pyridine (compound P1)

Step 1: Preparation of 3-chloro-2-(1H-imidazol-2-yl)-5-(trifluoromethyl)pyridine

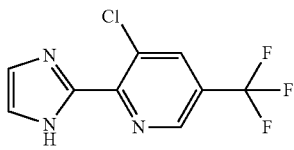

To a solution of 3-chloro-5-(trifluoromethyl)pyridine-2-carbonitrile (4.0 g, 19.37 mmol) in methanol (25 ml) was added sodium methoxide (30% (w/w) in MeOH) (0.192 g, 1.066 mmol, 0.20 ml, 30%) and the mixture was stirred at ambient temperature for 18 hours. 2,2-Diethoxy-ethanamine (2.75 g, 20.63 mmol, 3.0 ml) and acetic acid (2.36 g, 39.3 mmol, 2.25 ml) were added and the reaction mixture was heated at reflux for 30 min. The reaction mixture was cooled to ambient temperature, 6N HCl (aq) (10 ml) was added and the mixture was heated at reflux for 3 h. The reaction mixture was concentrated. To the residue was added water and the pH of the aqueous mixture was adjusted to ~9 with sat. Na$_2$CO$_3$ (aq). The precipitated solid was filtered off, washed twice with water and dried. The crude product was purified over silica by flash column chromatography (0-50% ethyl acetate gradient in heptane) to afford the title compound (2.94 g) as a solid. LCMS (method 1): 248 (M+H)$^+$, retention time 2.03 min. $^1$H-NMR (DMSO-d6, ppm) 7.31 (2H), 8.52 (1H), 8.95 (1H), 13.09 (1H).

Step 2: Preparation of 3-chloro-2-(1-methylimidazol-2-yl)-5-(trifluoromethyl)pyridine

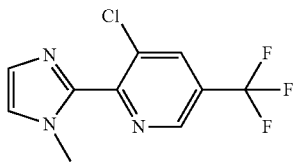 [SMILES: Cn1ccnc1-c1ncc(C(F)(F)F)cc1Cl]

To a solution of 3-chloro-2-(1H-imidazol-2-yl)-5-(trifluoromethyl)pyridine (2.9 g, 11.71 mmol) in dry tetrahydrofuran (90 ml) was added sodium hydride (0.703 g, 17.57 mmol, 60 wt %). After stirring for 10 min a yellow suspension was obtained. Iodomethane (3.18 g, 22.39 mmol, 1.4 ml) was added and the mixture was stirred at ambient temperature for 18 hours. An almost clear brown solution was obtained. The reaction mixture was poured into water and brine was added (water/brine ~1/1). The aqueous mixture was extracted twice with ethyl acetate. The combined organic layers were dried over sodium sulfate and concentrated. The crude product was purified over silica by flash column chromatography (10-50% ethyl acetate gradient in heptane) to afford the title compound (2.75 g) as an oil. LCMS (method 1): 262 (M+H)$^+$, retention time 1.94 min. $^1$H-NMR (CDCl$_3$, ppm) 3.85 (3H), 7.06 (1H), 7.26 (1H), 8.09 (1H), 8.82 (1H).

Step 3: Preparation of 3-ethylsulfanyl-2-(1-methyl-imidazol-2-yl)-5-(trifluoromethyl)pyridine

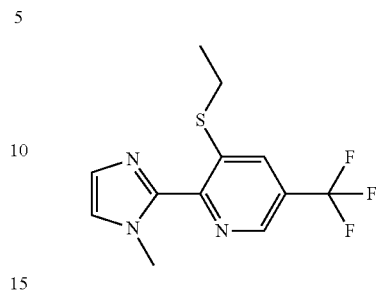

To a solution of 3-chloro-2-(1-methylimidazol-2-yl)-5-(trifluoromethyl)pyridine (2.75 g, 10.51 mmol) in dry N,N-dimethylformamide (20 ml) was added sodium ethanethiolate (1.061 g, 12.61 mmol) and the mixture was stirred at ambient temperature for 1 hour. The reaction mixture was poured into water/brine (1/1) and the aqueous mixture was extracted with ethyl acetate. The organic layer was washed twice with water/brine (1/1), dried over sodium sulfate and concentrated. The residue was purified over silica by flash column chromatography (5-50% ethyl acetate gradient in heptane) to afford the title compound (2.67 g) as a solid, mp 87-88° C. LCMS (method 2): 288 (M+H)$^+$, retention time 3.35 min. $^1$H-NMR (CDCl$_3$, ppm) 1.40 (3H), 2.96 (2H), 3.93 (3H), 7.03 (1H), 7.26 (1H), 7.79 (1H), 8.60 (1H).

Step 4: Preparation of 3-ethylsulfonyl-2-(1-methyl-imidazol-2-yl)-5-(trifluoromethyl)pyridine

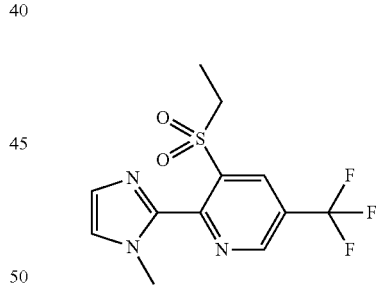

To a solution of 3-ethylsulfanyl-2-(1-methylimidazol-2-yl)-5-(trifluoromethyl)pyridine (2.67 g, 9.29 mmol) in dichloromethane (80 ml) was added mCPBA (70 wt % in water) (6.29 g, 25.5 mmol, 70%) in one portion. The mixture was stirred at ambient temperature for 4 hours. The reaction mixture was diluted with dichloromethane, washed with sat. aqueous sodium thiosulfate solution/sat. NaHCO$_3$ (1/1), with sat. NaHCO$_3$, dried over sodium sulfate and concentrated. The residue was purified over silica by flash column chromatography (10-75% ethyl acetate gradient in heptane) to afford the title compound (2.48 g) as a solid, mp 149-150° C. LCMS (method 2): 320 (M+H)$^+$, retention time 3.10 min. $^1$H-NMR (CDCl$_3$, ppm) 1.37 (3H), 3.77 (3H), 4.05 (2H), 7.09 (1H), 7.18 (1H), 8.71 (1H), 9.11 (1H).

Step 5: Preparation of 2-(5-bromo-1-methyl-imidazol-2-yl)-3-ethylsulfonyl-5-(trifluoromethyl)pyridine

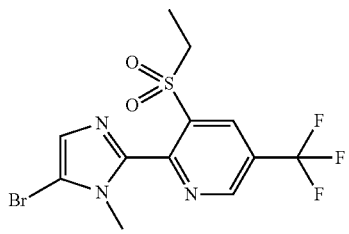 [SMILES: CCS(=O)(=O)c1cc(C(F)(F)F)cnc1-c1ncc(Br)n1C]

To a solution of 3-ethylsulfonyl-2-(1-methylimidazol-2-yl)-5-(trifluoromethyl)pyridine (319 mg, 0.999 mmol) in chloroform (10 ml) was added NBS (190 mg, 1.068 mmol) and the mixture was heated at 60° C. (oil bath temperature) for 1 hour. The reaction mixture was concentrated and the residue was purified over silica by flash column chromatography (5-40% ethyl acetate gradient in heptane) to afford the title compound (290 mg) as a solid. LCMS (method 1): 398/400 (M+H)+, retention time 2.17 min. 1H-NMR (CDCl3, ppm) 1.38 (3H), 3.70 (3H), 3.99 (2H), 7.18 (1H), 8.71 (1H), 9.20 (1H).

Step 6: Preparation of 3-ethylsulfonyl-2-[1-methyl-5-[3-(trifluoromethyl)phenyl]imidazol-2-yl]-5-(trifluoromethyl)pyridine (title compound P1)

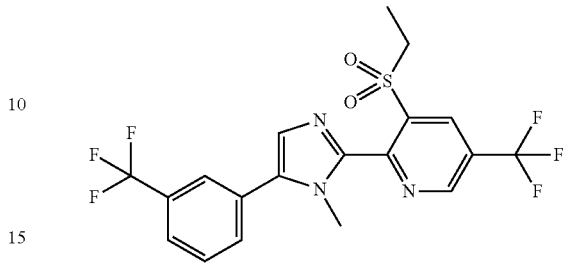

In a microwave vial, a mixture of 2-(5-bromo-1-methyl-imidazol-2-yl)-3-ethylsulfonyl-5-(trifluoromethyl)pyridine (199 mg, 0.50 mmol), (3-(trifluoromethyl)phenyl)boronic acid (142 mg, 0.750 mmol) and sodium carbonate (159 mg, 1.500 mmol) in 1,2-dimethoxyethane (2 ml) and water (0.5 ml) was flushed with argon for 5 min. To this was added PdCl2(dppf) (14.63 mg, 0.020 mmol), the vial was closed and heated in the microwave at 120° C. for 1 h. The reaction mixture was diluted with ethyl acetate and washed with water, brine, dried over sodium sulfate and concentrated. The residue was purified over silica by flash column chromatography (5-40% ethyl acetate gradient in heptane). The fractions containing product were combined, concentrated and again purified over silica by flash column chromatography (0-2.5% methanol gradient in dichloromethane). The fractions containing product were combined, concentrated and the product was recrystallized from heptane to afford the title compound (72 mg) as a solid, mp 149-150° C. LCMS (method 2): 464 (M+H)+, retention time 4.06 min. 1H-NMR (CDCl3, ppm) 1.41 (3H), 3.69 (3H), 4.07 (2H), 7.29 (1H), 7.61-7.71 (3H), 7.76 (1H), 8.74 (1H), 9.15 (1H).

TABLE P1

Examples of compounds of formula (I)

| Compound No. | Structures | Melting Point | MS/NMR |
|---|---|---|---|
| P1 | | 149-150° C. | LCMS (method 2): 464 (M + H)+ Rt = 4.06 min |
| P2 | | 136-137° C. | LCMS (method 2): 464 (M + H)+ Rt = 3.93 min |

| Compound No. | Structures | LCMS Rt (min) | [M + H]+ (measured) | Method | Mp (° C.) |
|---|---|---|---|---|---|
| P3 | 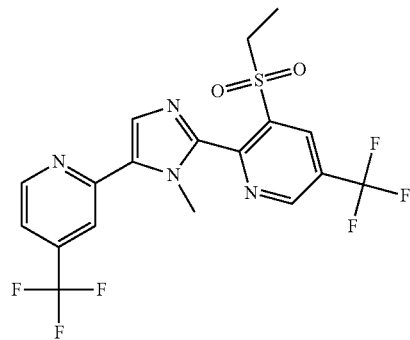 [SMILES: CCS(=O)(=O)c1cc(C(F)(F)F)cnc1-c1ncc(-c2cc(C(F)(F)F)ccn2)n1C] | 3.85 | 465 | 2 | 147-148 |

TABLE P1-continued

Examples of compounds of formula (I)

| | | | | | |
|---|---|---|---|---|---|
| P4 | (structure) | 3.69 | 465 | 2 | 168-169 |
| P5 | (structure) | 3.63 | 465 | 2 | 197-198 |
| P6 | (structure) | 3.71 | 465 | 2 | 148.5-149.5 |
| P7 | (structure) | 4.24 | 498/500 | 2 | 159-160 |
| P8 | (structure) | 3.93 | 465 | 2 | 148-150 |

TABLE P1-continued

Examples of compounds of formula (I)

| | | | | | |
|---|---|---|---|---|---|
| P9 | (structure) | 1.06 | 463 | 4 | 139-141 |
| P10 | (structure) | 0.99 | 464 | 4 | 153-155 |
| P11 | (structure) | 1.65 | 479 | 3 | 139-140 |
| P12 | (structure) | 3.92 | 528 | 2 | 155-157 |
| P13 | (structure) | 4.14 | 496 | 2 | 151-153 |

TABLE P1-continued

Examples of compounds of formula (I)

| P14 | [structure] | 3.89 | 528 | 2 | 191-192 |
| P15 | [structure] | 4.15 | 496 | 2 | 117-118 |
| P16 | [structure] | 4.06 | 478 | 2 | 186-187 |
| P17 | [structure] | 1.92 | 464 | 5 | |
| P18 | [structure] | 1.75 | 430 | 5 | |

TABLE P1-continued

Examples of compounds of formula (I)

| | Structure | | | |
|---|---|---|---|---|
| P19 | | 1.49 | 465 | 5 |
| P20 | | 1.81 | 482 | 5 |
| P21 | | 1.50 | 438 | 5 |
| P22 | | 1.85 | 480 | 5 |
| P23 | | 1.48 | 431 | 5 |
| P24 | | 2.03 | 564 | 5 |

TABLE P1-continued
Examples of compounds of formula (I)
| P25 | 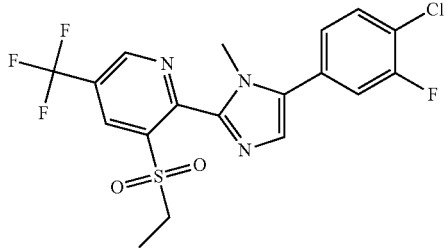 [SMILES: CCS(=O)(=O)c1cc(C(F)(F)F)cnc1-c1ncc(-c2ccc(Cl)c(F)c2)n1C] | 1.79 | 448 | 5 |
| P26 | 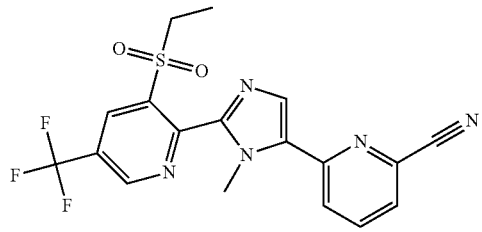 [SMILES: CCS(=O)(=O)c1cc(C(F)(F)F)cnc1-c1ncc(-c2cccc(C#N)n2)n1C] | 1.48 | 422 | 5 |
| P27 | 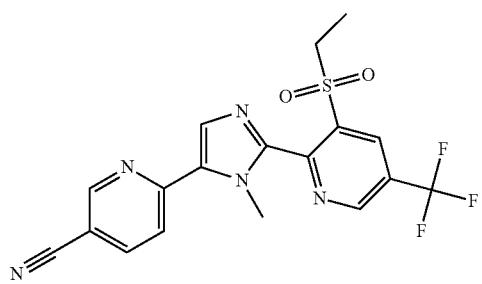 [SMILES: CCS(=O)(=O)c1cc(C(F)(F)F)cnc1-c1ncc(-c2ccc(C#N)cn2)n1C] | 1.51 | 422 | 5 |
| P28 | 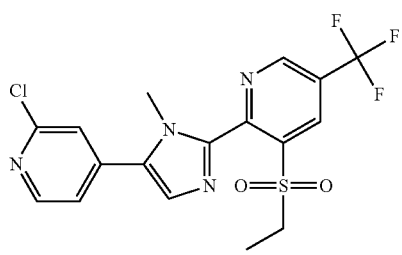 [SMILES: CCS(=O)(=O)c1cc(C(F)(F)F)cnc1-c1ncc(-c2ccnc(Cl)c2)n1C] | 1.48 | 431 | 5 |
| P29 | 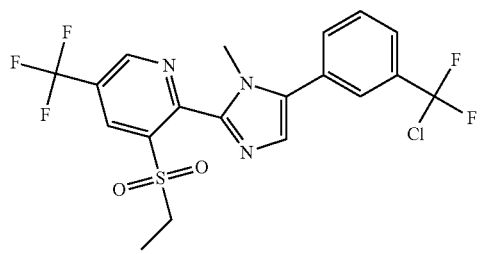 [SMILES: CCS(=O)(=O)c1cc(C(F)(F)F)cnc1-c1ncc(-c2cccc(C(F)(F)Cl)c2)n1C] | 1.87 | 480 | 5 |

TABLE P1-continued

Examples of compounds of formula (I)

| | | | | |
|---|---|---|---|---|
| P30 | | 1.91 | 498 | 5 |
| P31 | | 1.92 | 532 | 5 |
| P32 | | 1.61 | 455 | 5 |
| P33 | | 1.90 | 482 | 5 |
| P34 | | 1.75 | 430 | 5 |
| P35 | | 1.88 | 464 | 5 |

TABLE P1-continued
Examples of compounds of formula (I)
| P36 | 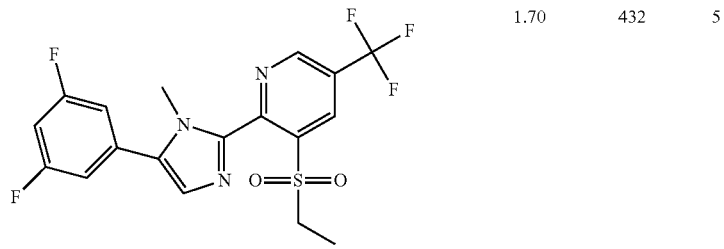 | 1.70 | 432 | 5 |
| P37 | 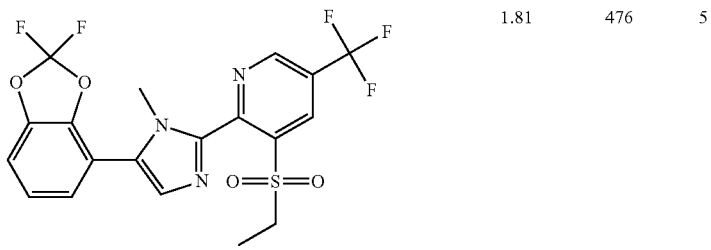 | 1.81 | 476 | 5 |
| P38 | 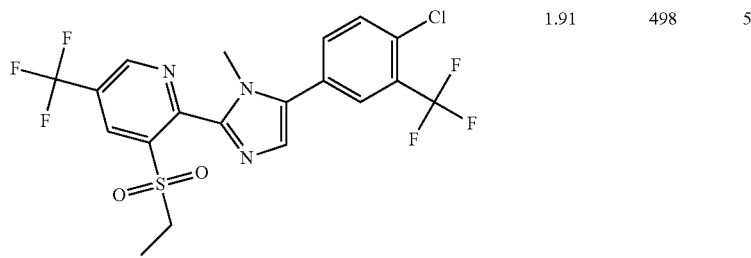 | 1.91 | 498 | 5 |
| P39 | 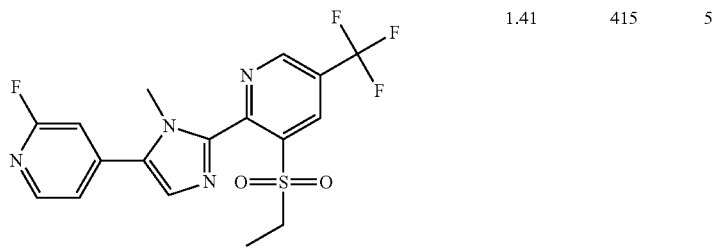 | 1.41 | 415 | 5 |
| P40 | 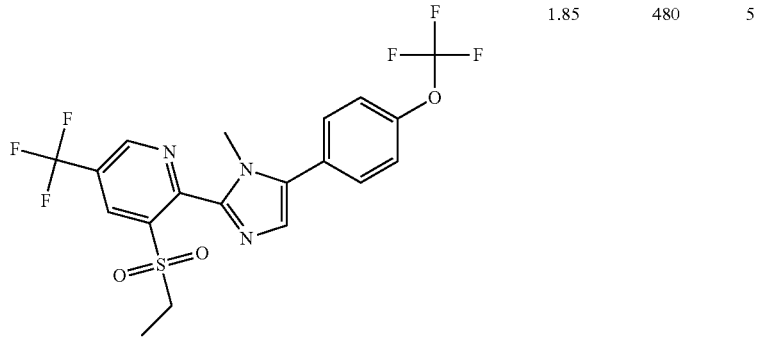 | 1.85 | 480 | 5 |

TABLE P1-continued

Examples of compounds of formula (I)

| | | | | |
|---|---|---|---|---|
| P41 | | 1.51 | 421 | 5 |
| P42 | | 1.50 | 438 | 5 |
| P43 | | 1.68 | 432 | 5 |
| P44 | | 1.75 | 450 | 5 |
| P45 | | 1.52 | 421 | 5 |
| P46 | | 1.32 | 422 | 5 |

TABLE P1-continued

Examples of compounds of formula (I)

| | | | | |
|---|---|---|---|---|
| P47 | (structure) | 1.37 | 422 | 5 |
| P48 | (structure) | 1.81 | 476 | 5 |
| P49 | (structure) | 1.94 | 532 | 5 |
| P50 | (structure) | 1.55 | 466 | 5 |
| P51 | (structure) | 1.92 | 499 | 5 |

TABLE P1-continued

Examples of compounds of formula (I)

| | | | | |
|---|---|---|---|---|
| P52 | (structure) | 1.97 | 532 | 5 |
| P53 | (structure) | 1.77 | 448 | 5 |
| P54 | (structure) | 1.39 | 415 | 5 |
| P55 | (structure) | 1.46 | 422 | 5 |

TABLE P2

Examples of intermediates of formula (IIIa) and (IVa)

| Compound No. | Structures | LCMS R_t (min) | [M + H]⁺ (measured) | Method | Mp (° C.) |
|---|---|---|---|---|---|
| P2.1 | (structure) | | | | 132-133 |
| | $^1$H-NMR (CDCl$_3$, ppm) 1.38 (3H), 3.69 (3H), 4.10 (2H), 7.12 (1H), 8.72 (1H), 9.12 (1H). | | | | |
| P2.2 | (structure) | 3.10 | 320 | 2 | 149-150 |
| P2.3 | (structure) | 3.35 | 288 | 2 | 87-88 |
| P2.4 | (structure) | 1.11 | 334 | 3 | 144-116 |
| P2.5 | (structure) | 2.17 | 398/400 | 1 | 148-150 |

TABLE P2-continued

Examples of intermediates of formula (IIIa) and (IVa)

| Compound No. | Structures | R$_t$ (min) | [M + H]$^+$ (measured) | Method | Mp (° C.) |
|---|---|---|---|---|---|
| P2.6 | (structure shown) | 1.60 | 412/414 | 3 | 126-129 |

FORMULATION EXAMPLES (%=PERCENT BY WEIGHT)

Example F1: Emulsion Concentrates

| | a) | b) | c) |
|---|---|---|---|
| Active ingredient | 25% | 40% | 50% |
| Calcium dodecylbenzenesulfonate | 5% | 8% | 6% |
| Castor oil polyethylene glycol ether (36 mol of EO) | 5% | — | — |
| Tributylphenoxypolyethylene glycol ether (30 mol of EO) | — | 12% | 4% |
| Cyclohexanone | — | 15% | 20% |
| Xylene mixture | 65% | 25% | 20% |

Emulsions of any desired concentration can be prepared from such concentrates by dilution with water.

Example F2: Solutions

| | a) | b) | c) | d) |
|---|---|---|---|---|
| Active ingredient | 80% | 10% | 5% | 95% |
| Ethylene glycol monomethyl ether | 20% | — | — | — |
| Polyethylene glycol MW 400 | — | 70% | — | — |
| N-Methylpyrrolid-2-one | — | 20% | — | — |
| Epoxidized coconut oil | — | — | 1% | 5% |
| Petroleum ether (boiling range: 160-190°) | — | — | 94% | — |

The solutions are suitable for use in the form of microdrops.

Example F3: Granules

| | a) | b) | c) | d) |
|---|---|---|---|---|
| Active ingredient | 5% | 10% | 8% | 21% |
| Kaolin | 94% | — | 79% | 54% |
| Highly disperse silica | 1% | — | 13% | 7% |
| Attapulgite | — | 90% | — | 18% |

The active ingredient is dissolved in dichloromethane, the solution is sprayed onto the carrier(s), and the solvent is subsequently evaporated in vacuo.

Example F4: Dusts

| | a) | b) |
|---|---|---|
| Active ingredient | 2% | 5% |
| Highly disperse silica | 1% | 5% |
| Talc | 97% | — |
| Kaolin | — | 90% |

Ready-to-use dusts are obtained by intimately mixing the carriers and the active ingredient.

Example F5: Wettable Powders

| | a) | b) | c) |
|---|---|---|---|
| Active ingredient | 25% | 50% | 75% |
| Sodium lignosulfonate | 5% | 5% | — |
| Sodium lauryl sulfate | 3% | — | 5% |
| Sodium diisobutylnaphthalenesulfonate | — | 6% | 10% |
| Octylphenoxypolyethylene glycol ether (7-8 mol of EO) | — | 2% | — |
| Highly disperse silica | 5% | 10% | 10% |
| Kaolin | 62% | 27% | — |

The active ingredient is mixed with the additives and the mixture is ground thoroughly in a suitable mill. This gives wettable powders, which can be diluted with water to give suspensions of any desired concentration.

Example F6: Extruder Granules

| | |
|---|---|
| Active ingredient | 10% |
| Sodium lignosulfonate | 2% |
| Carboxymethylcellulose | 1% |
| Kaolin | 87% |

The active ingredient is mixed with the additives, and the mixture is ground, moistened with water, extruded, granulated and dried in a stream of air.

Example F7: Coated Granules

| | |
|---|---|
| Active ingredient | 3% |
| Polyethylene glycol (MW 200) | 3% |
| Kaolin | 94% |

In a mixer, the finely ground active ingredient is applied uniformly to the kaolin, which has been moistened with the polyethylene glycol. This gives dust-free coated granules.

Example F8: Suspension Concentrate

| | |
|---|---|
| Active ingredient | 40% |
| Ethylene glycol | 10% |
| Nonylphenoxypolyethylene glycol ether (15 mol of EO) | 6% |
| Sodium lignosulfonate | 10% |
| Carboxymethylcellulose | 1% |
| 37% aqueous formaldehyde solution | 0.2% |
| Silicone oil (75% aqueous emulsion) | 0.8% |
| Water | 32% |

The finely ground active ingredient is mixed intimately with the additives. Suspensions of any desired concentration can be prepared from the thus resulting suspension concentrate by dilution with water.

Example F9: Powders for Dry Seed Treatment

| | a) | b) | c) |
|---|---|---|---|
| active ingredient | 25% | 50% | 75% |
| light mineral oil | 5% | 5% | 5% |
| highly dispersed silicic acid | 5% | 5% | — |
| Kaolin | 65% | 40% | — |
| Talcum | — | — | 20% |

The combination is thoroughly mixed with the adjuvants and the mixture is thoroughly ground in a suitable mill, affording powders that can be used directly for seed treatment.

Example F10: Emulsifiable Concentrate

| | |
|---|---|
| active ingredient | 10% |
| octylphenol polyethylene glycol ether (4-5 mol of ethylene oxide) | 3% |
| calcium dodecylbenzenesulfonate | 3% |
| castor oil polyglycol ether (35 mol of ethylene oxide) | 4% |
| Cyclohexanone | 30% |
| xylene mixture | 50% |

Emulsions of any required dilution, which can be used in plant protection, can be obtained from this concentrate by dilution with water.

Example F11: Flowable Concentrate for Seed Treatment

| | |
|---|---|
| active ingredients | 40% |
| propylene glycol | 5% |
| copolymer butanol PO/EO | 2% |
| Tristyrenephenole with 10-20 moles EO | 2% |
| 1,2-benzisothiazolin-3-one (in the form of a 20% solution in water) | 0.5% |
| monoazo-pigment calcium salt | 5% |
| Silicone oil (in the form of a 75% emulsion in water) | 0.2% |
| Water | 45.3% |

The finely ground combination is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

The activity of the compositions according to the invention can be broadened considerably, and adapted to prevailing circumstances, by adding other insecticidally, acaricidally and/or fungicidally active ingredients. The mixtures of the compounds of formula I with other insecticidally, acaricidally and/or fungicidally active ingredients may also have further surprising advantages which can also be described, in a wider sense, as synergistic activity. For example, better tolerance by plants, reduced phytotoxicity, insects can be controlled in their different development stages or better behaviour during their production, for example during grinding or mixing, during their storage or during their use. Suitable additions to active ingredients here are, for example, representatives of the following classes of active ingredients: organophosphorus compounds, nitrophenol derivatives, thioureas, juvenile hormones, formamidines, benzophenone derivatives, ureas, pyrrole derivatives, carbamates, pyrethroids, chlorinated hydrocarbons, acylureas, pyridylmethyleneamino derivatives, macrolides, neonicotinoids and *Bacillus thuringiensis* preparations.

The following mixtures of the compounds of formula I with active ingredients are preferred (the abbreviation "TX" means "one compound selected from the group consisting of the compounds described in Tables 1 to 6 of the present invention"):
an adjuvant selected from the group of substances consisting of petroleum oils (alternative name) (628)+TX,
an acaricide selected from the group of substances consisting of 1,1-bis(4-chlorophenyl)-2-ethoxyethanol (IUPAC name) (910)+TX, 2,4-dichlorophenyl benzenesulfonate (IUPAC/Chemical Abstracts name) (1059)+TX, 2-fluoro-N-methyl-N-1-naphthylacetamide (IUPAC name) (1295)+TX, 4-chlorophenyl phenyl sulfone (IUPAC name) (981)+TX, abamectin (1)+TX, acequinocyl (3)+TX, acetoprole [CCN]+TX, acrinathrin (9)+TX, aldicarb (16)+TX, aldoxycarb (863)+TX, alpha-cypermethrin (202)+TX, amidithion (870)+TX, amidoflumet [CCN]+TX, amidothioate (872)+TX, amiton (875)+TX, amiton hydrogen oxalate (875)+TX, amitraz (24)+TX, aramite (881)+TX, arsenous oxide (882)+TX, AVI 382 (compound code)+TX, AZ 60541 (compound code)+TX, azinphos-ethyl (44)+TX, azinphos-methyl (45)+TX, azobenzene (IUPAC name) (888)+TX, azocyclotin (46)+TX, azothoate (889)+TX, benomyl (62)+TX, benoxafos (alternative name) [CCN]+TX, benzoximate (71)+TX, benzyl benzoate (IUPAC name) [CCN]+TX, bifenazate (74)+TX, bifenthrin (76)+TX, binapacryl (907)+TX, brofenvalerate (alternative name)+TX, bromocyclen (918)+TX, bromophos (920)+TX, bromophos-ethyl (921)+TX, bromopropylate (94)+TX, buprofezin (99)+TX, butocarboxim (103)+TX, butoxycarboxim (104)+TX, butylpyridaben (alternative name)+TX, calcium polysulfide (IUPAC name) (111)+TX, camphechlor (941)+TX, carbanolate (943)+TX, carbaryl (115)+TX, carbofuran (118)+TX, carbophenothion (947)+TX, CGA 50'439 (development code) (125)+TX, chinomethionat (126)+TX, chlorbenside (959)+TX, chlordimeform (964)+TX, chlordimeform hydrochloride (964)+TX, chlorfenapyr (130)+TX, chlorfenethol (968)+TX, chlorfenson (970)+TX, chlorfensulfide (971)+TX, chlorfenvinphos (131)+TX, chlorobenzilate (975)+TX, chloromebuform (977)+TX, chloromethiuron (978)+TX, chloropropylate (983)+TX, chlorpyrifos (145)+TX, chlorpyrifos-methyl (146)+TX, chlorthiophos (994)+TX, cinerin I (696)+TX, cinerin II (696)+TX, cinerins (696)+TX, clofentezine (158)+TX, closantel (alternative name) [CCN]+TX, coumaphos (174)+TX, crotamiton (alternative name) [CCN]+TX, crotoxyphos (1010)+TX, cufraneb (1013)+TX, cyanthoate (1020)+TX, cyflumetofen (CAS Reg. No.: 400882-07-7)+TX, cyhalothrin (196)+TX, cyhexatin (199)+TX, cypermethrin (201)+TX, DCPM (1032)+TX, DDT (219)+TX, demephion (1037)+TX, demephion-O (1037)+TX, demephion-S (1037)+TX, demeton (1038)+TX, demeton-methyl (224)+TX, demeton-O (1038)+TX, demeton-O-methyl (224)+TX, demeton-S (1038)+TX, demeton-S-methyl (224)+TX, demeton-S-methylsulfon (1039)+TX, diafenthiuron (226)+TX, dialifos (1042)+TX, diazinon (227)+TX, dichlofluanid (230)+TX, dichlorvos (236)+TX, dicliphos (alternative name)+TX, dicofol (242)+TX, dicrotophos (243)+TX, dienochlor (1071)+TX, dimefox (1081)+TX, dimethoate (262)+TX, dinactin (alternative name) (653)+TX, dinex (1089)+TX, dinex-diclexine (1089)+TX, dinobuton (269)+TX, dinocap (270)+TX, dinocap-4 [CCN]+TX, dinocap-6 [CCN]+TX, dinocton (1090)+TX, dinopenton (1092)+TX, dinosulfon (1097)+TX, dinoterbon (1098)+TX, dioxathion (1102)+TX, diphenyl sulfone (IUPAC name) (1103)+TX, disulfiram (alternative name) [CCN]+TX, disulfoton (278)+TX, DNOC (282)+TX, dofenapyn (1113)+TX, doramectin (alternative name) [CCN]+TX, endosulfan (294)+TX, endothion (1121)+TX, EPN (297)+TX, eprinomectin (alternative name) [CCN]+TX, ethion (309)+TX, ethoate-methyl (1134)+TX, etoxazole (320)+TX, etrimfos (1142)+TX, fenazaflor (1147)+TX, fenazaquin (328)+TX, fenbutatin oxide (330)+TX, fenothiocarb (337)+TX, fenpropathrin (342)+TX, fenpyrad (alternative name)+TX, fenpyroximate (345)+TX, fenson (1157)+TX, fentrifanil (1161)+TX, fenvalerate (349)+TX, fipronil (354)+TX, fluacrypyrim (360)+TX, fluazuron (1166)+TX, flubenzimine (1167)+TX, flucycloxuron (366)+TX, flucythrinate (367)+TX, fluenetil (1169)+TX, flufenoxuron (370)+TX, flumethrin (372)+TX, fluorbenside (1174)+TX, fluvalinate (1184)+TX, FMC 1137 (development code) (1185)+TX, formetanate (405)+TX, formetanate hydrochloride (405)+TX, formothion (1192)+TX, formparanate (1193)+TX, gamma-HCH (430)+TX, glyodin (1205)+TX, halfenprox (424)+TX, heptenophos (432)+TX, hexadecyl cyclopropanecarboxylate (IUPAC/Chemical Abstracts name) (1216)+TX, hexythiazox (441)+TX, iodomethane (IUPAC name) (542)+TX, isocarbophos (alternative name) (473)+TX, isopropyl O-(methoxyaminothiophosphoryl)salicylate (IUPAC name) (473)+TX, ivermectin (alternative name) [CCN]+TX, jasmolin I (696)+TX, jasmolin II (696)+TX, jodfenphos (1248)+TX, lindane (430)+TX, lufenuron (490)+TX, malathion (492)+TX, malonoben (1254)+TX, mecarbam (502)+TX, mephosfolan (1261)+TX, mesulfen (alternative name) [CCN]+TX, methacrifos (1266)+TX, methamidophos (527)+TX, methidathion (529)+TX, methiocarb (530)+TX, methomyl (531)+TX, methyl bromide (537)+TX, metolcarb (550)+TX, mevinphos (556)+TX, mexacarbate (1290)+TX, milbemectin (557)+TX, milbemycin oxime (alternative name) [CCN]+TX, mipafox (1293)+TX, monocrotophos (561)+TX, morphothion (1300)+TX, moxidectin (alternative name) [CCN]+TX, naled (567)+TX, NC-184 (compound code)+TX, NC-512 (compound code)+TX, nifluridide (1309)+TX, nikkomycins (alternative name) [CCN]+TX, nitrilacarb (1313)+TX, nitrilacarb 1:1 zinc chloride complex (1313)+TX, NNI-0101 (compound code)+TX, NNI-0250 (compound code)+TX, omethoate (594)+TX, oxamyl (602)+TX, oxydeprofos (1324)+TX, oxydisulfoton (1325)+TX, pp'-DDT (219)+TX, parathion (615)+TX, permethrin (626)+TX, petroleum oils (alternative name) (628)+TX, phenkapton (1330)+TX, phenthoate (631)+TX, phorate (636)+TX, phosalone (637)+TX, phosfolan (1338)+TX, phosmet (638)+TX, phosphamidon (639)+TX, phoxim (642)+TX, pirimiphos-methyl (652)+TX, polychloroterpenes (traditional name) (1347)+TX, polynactins (alternative name) (653)+TX, proclonol (1350)+TX, profenofos (662)+TX, promacyl (1354)+TX, propargite (671)+TX, propetamphos (673)+TX, propoxur (678)+TX, prothidathion (1360)+TX, prothoate (1362)+TX, pyrethrin I (696)+TX, pyrethrin II (696)+TX, pyrethrins (696)+TX, pyridaben (699)+TX, pyridaphenthion (701)+TX, pyrimidifen (706)+TX, pyrimitate (1370)+TX, quinalphos (711)+TX, quintiofos (1381)+TX, R-1492 (development code) (1382)+TX, RA-17 (development code) (1383)+TX, rotenone (722)+TX, schradan (1389)+TX, sebufos (alternative name)+TX, selamectin (alternative name) [CCN]+TX, SI-0009 (compound code)+TX, sophamide (1402)+TX, spirodiclofen (738)+TX, spiromesifen (739)+TX, SSI-121 (development code) (1404)+TX, sulfiram (alternative name) [CCN]+TX, sulfluramid (750)+TX, sulfotep (753)+TX, sulfur (754)+TX, SZI-121 (development code) (757)+TX, tau-fluvalinate (398)+TX, tebufenpyrad (763)+TX, TEPP (1417)+TX, terbam (alternative name)+TX, tetrachlorvinphos (777)+TX, tetradifon (786)+TX, tetranactin (alternative name) (653)+TX, tetrasul (1425)+TX, thiafenox (alternative name)+TX, thiocarboxime (1431)+TX, thiofanox (800)+TX, thiometon (801)+TX, thioquinox (1436)+TX, thuringiensin (alternative name) [CCN]+TX, triamiphos (1441)+TX, triarathene (1443)+TX, triazophos (820)+TX, triazuron (alternative name)+TX, trichlorfon (824)+TX, trifenofos (1455)+TX, trinactin (alternative name) (653)+TX, vamidothion (847)+TX, vaniliprole [CCN] and YI-5302 (compound code)+TX, an algicide selected from the group of substances consisting of bethoxazin [CCN]+TX, copper dioctanoate (IUPAC name) (170)+TX, copper sulfate (172)+TX, cybutryne [CCN]+TX, dichlone (1052)+TX, dichlorophen (232)+TX, endothal (295)+TX, fentin (347)+TX, hydrated lime [CCN]+TX, nabam (566)+TX, quinoclamine (714)+TX, quinonamid (1379)+TX, simazine (730)+TX, triphenyltin acetate (IUPAC name) (347) and triphenyltin hydroxide (IUPAC name) (347)+TX, an anthelmintic selected from the group of substances consisting of abamectin (1)+TX, crufomate (1011)+TX, doramectin (alternative name) [CCN]+TX, emamectin (291)+TX, emamectin benzoate (291)+TX, eprinomectin (alternative name) [CCN]+TX, ivermectin (alternative name) [CCN]+TX, milbemycin oxime (alternative name) [CCN]+TX, moxidectin (alternative name) [CCN]+TX, piperazine [CCN]+TX, selamectin (alternative name) [CCN]+TX, spinosad (737) and thiophanate (1435)+TX, an avicide selected from the group of substances consisting of chloralose (127)+TX, endrin (1122)+TX, fenthion (346)+TX, pyridin-4-amine (IUPAC name) (23) and strychnine (745)+TX, a bactericide selected from the group of substances consisting of 1-hydroxy-1H-pyridine-2-thione (IUPAC name) (1222)+TX, 4-(quinoxalin-2-ylamino)benzenesulfonamide (IUPAC name) (748)+TX, 8-hydroxyquinoline sulfate (446)+TX, bronopol (97)+TX, copper dioctanoate (IUPAC name) (170)+TX, copper hydroxide (IUPAC name) (169)+TX, cresol [CCN]+TX, dichlorophen (232)+TX, dipyrithione (1105)+TX, dodicin (1112)+TX, fenaminosulf (1144)+TX, formaldehyde (404)+TX, hydrargaphen (alternative name) [CCN]+TX, kasugamycin (483)+TX, kasugamycin hydrochloride hydrate (483)+TX, nickel bis(dimethyldithiocarbamate) (IUPAC name) (1308)+TX, nitrapyrin (580)+TX, octhilinone (590)+TX, oxolinic acid (606)+TX, oxytetracycline (611)+TX, potassium hydroxyquinoline sulfate (446)+TX, probenazole (658)+TX, streptomycin (744)+TX, streptomycin sesquisulfate (744)+TX, tecloftalam (766)+TX, and thiomersal (alternative name) [CCN]+TX, a biological agent selected from the group of substances consisting of *Adoxophyes orana* GV (alternative name) (12)+TX, *Agrobacterium radiobacter* (alternative name) (13)+TX, *Amblyseius* spp. (alternative name) (19)+TX, *Anagrapha falcifera* NPV (alternative name) (28)+TX, *Anagrus atomus* (alternative name) (29)+TX, *Aphelinus abdominalis* (alternative name) (33)+TX, *Aphidius colemani* (alternative name) (34)+TX, *Aphidoletes aphidimyza* (alternative name) (35)+TX, *Autographa californica* NPV (alternative name) (38)+TX, *Bacillus firmus* (alternative name) (48)+TX, *Bacillus sphaericus* Neide (scientific name) (49)+TX, *Bacillus thuringiensis* Berliner (scientific name) (51)+TX, *Bacillus thuringiensis* subsp. *aizawai* (scientific name) (51)+TX, *Bacillus thuringiensis* subsp. *israelensis* (scientific name) (51)+TX, *Bacillus thuringiensis* subsp. *japonensis* (scientific name) (51)+TX, *Bacillus thuringiensis* subsp. *kurstaki* (scientific name) (51)+TX, *Bacillus thuringiensis* subsp. *tenebrionis* (scientific name) (51)+TX, *Beauveria bassiana* (alternative name) (53)+TX, *Beauveria brongniartii* (alternative name) (54)+TX, *Chrysoperla carnea* (alternative name) (151)+TX, *Cryptolaemus montrouzieri* (alternative name) (178)+TX, *Cydia pomonella* GV (alternative name) (191)+TX, *Dacnusa sibirica* (alternative name) (212)+TX, *Diglyphus isaea* (alternative name) (254)+TX, *Encarsia formosa* (scientific name) (293)+TX, *Eretmocerus eremicus* (alternative name) (300)+TX, *Helicoverpa zea* NPV (alternative name) (431)+TX, *Heterorhabditis bacteriophora* and *H. megidis* (alternative name) (433)+TX, *Hippodamia convergens* (alternative name) (442)+TX, *Leptomastix dactylopii* (alternative name) (488)+TX, *Macrolophus caliginosus* (alternative name) (491)+TX, *Mamestra brassicae* NPV (alternative name) (494)+TX, *Metaphycus helvolus* (alternative name) (522)+TX, *Metarhizium anisopliae* var. *acridum* (scientific name) (523)+TX, *Metarhizium anisopliae* var. *anisopliae* (scientific name) (523)+TX, *Neodiprion sertifer* NPV and *N. lecontei* NPV (alternative name) (575)+TX, *Orius* spp. (alternative name) (596)+TX, *Paecilomyces fumosoroseus* (alternative name) (613)+TX, *Phytoseiulus persimilis* (alternative name) (644)+TX, *Spodoptera exigua* multicapsid nuclear polyhedrosis virus (scientific name) (741)+TX, *Steinernema bibionis* (alternative name) (742)+TX, *Steinernema carpocapsae* (alternative name) (742)+TX, *Steinernema feltiae* (alternative name) (742)+TX, *Steinernema glaseri* (alternative name) (742)+TX, *Steinernema riobrave* (alternative name) (742)+TX, *Steinernema riobravis* (alternative name) (742)+TX, *Steinernema scapterisci* (alternative name) (742)+TX, *Steinernema* spp. (alternative name) (742)+TX, *Trichogramma* spp. (alternative name) (826)+TX, *Typhlodromus occidentalis* (alternative name) (844) and *Verticillium lecanii* (alternative name) (848)+TX, a soil sterilant selected from the group of substances consisting of iodomethane (IUPAC name) (542) and methyl bromide (537)+TX, a chemosterilant selected from the group of substances consisting of apholate [CCN]+TX, bisazir (alternative name) [CCN]+TX, busulfan (alternative name) [CCN]+TX, diflubenzuron (250)+TX, dimatif (alternative name) [CCN]+TX, hemel [CCN]+TX, hempa [CCN]+TX, metepa [CCN]+TX, methiotepa [CCN]+TX, methyl apholate [CCN]+TX, morzid [CCN]+TX, penfluron (alternative name) [CCN]+TX, tepa [CCN]+TX, thiohempa (alternative name) [CCN]+TX, thiotepa (alternative name) [CCN]+TX, tretamine (alternative name) [CCN] and uredepa (alternative name) [CCN]+TX, an insect pheromone selected from the group of substances consisting of (E)-dec-5-en-1-yl acetate with (E)-dec-5-en-1-ol (IUPAC name) (222)+TX, (E)-tridec-4-en-1-yl acetate (IUPAC name) (829)+TX, (E)-6-methylhept-2-en-4-ol (IUPAC name) (541)+TX, (E,Z)-tetradeca-4,10-dien-1-yl acetate (IUPAC name) (779)+TX, (Z)-dodec-7-en-1-yl acetate (IUPAC name) (285)+TX, (Z)-hexadec-11-enal (IUPAC name) (436)+TX, (Z)-hexadec-11-en-1-yl acetate (IUPAC name) (437)+TX, (Z)-hexadec-13-en-11-yn-1-yl acetate (IUPAC name) (438)+TX, (Z)-icos-13-en-10-one (IUPAC name) (448)+TX, (Z)-tetradec-7-en-1-al (IUPAC name) (782)+TX, (Z)-tetradec-9-en-1-ol (IUPAC name) (783)+TX, (Z)-tetradec-9-en-1-yl acetate (IUPAC name) (784)+TX, (7E,9Z)-dodeca-7,9-dien-1-yl acetate (IUPAC name) (283)+TX, (9Z,11E)-tetradeca-9,11-dien-1-yl acetate (IUPAC name) (780)+TX, (9Z,12E)-tetradeca-9,12-dien-1-yl acetate (IUPAC name) (781)+TX, 14-methyloctadec-1-ene (IUPAC name) (545)+TX, 4-methylnonan-5-ol with 4-methylnonan-5-one (IUPAC name) (544)+TX, alpha-multistriatin (alternative name) [CCN]+TX, brevicomin (alternative name) [CCN]+TX, codlelure (alternative name) [CCN]+TX, codlemone (alternative name) (167)+TX, cuelure (alternative name) (179)+TX, disparlure (277)+TX, dodec-8-en-1-yl acetate (IUPAC name) (286)+TX, dodec-9-en-1-yl acetate (IUPAC name) (287)+TX, dodeca-8+TX, 10-dien-1-yl acetate (IUPAC name) (284)+TX, dominicalure (alternative name) [CCN]+TX, ethyl 4-methyloctanoate (IUPAC name) (317)+TX, eugenol (alternative name) [CCN]+TX, frontalin (alternative name) [CCN]+TX, gossyplure (alternative name) (420)+TX, grandlure (421)+TX, grandlure I (alternative name) (421)+TX, grandlure II (alternative name) (421)+TX, grandlure III (alternative name) (421)+TX, grandlure IV (alternative name) (421)+TX, hexalure [CCN]+TX, ipsdienol (alternative name) [CCN]+TX, ipsenol (alternative name) [CCN]+TX, japonilure (alternative name) (481)+TX, lineatin (alternative name) [CCN]+TX, litlure (alternative name) [CCN]+TX, looplure (alternative name) [CCN]+TX, medlure [CCN]+TX, megatomoic acid (alternative name) [CCN]+TX, methyl eugenol (alternative name) (540)+TX, muscalure (563)+TX, octadeca-2,13-dien-1-yl acetate (IUPAC name) (588)+TX, octadeca-3,13-dien-1-yl acetate (IUPAC name) (589)+TX, orfralure (alternative name) [CCN]+TX, oryctalure (alternative name) (317)+TX, ostramone (alternative name) [CCN]+TX, siglure [CCN]+TX, sordidin (alternative name) (736)+TX, sulcatol (alternative name) [CCN]+TX, tetradec-11-en-1-yl acetate (IUPAC name) (785)+TX, trimedlure (839)+TX, trimedlure A (alternative name) (839)+TX, trimedlure $B_1$ (alternative name) (839)+TX, trimedlure $B_2$ (alternative name) (839)+TX, trimedlure C (alternative name) (839) and trunc-call (alternative name) [CCN]+TX, an insect repellent selected from the group of substances consisting of 2-(octylthio)ethanol (IUPAC name) (591)+TX, butopyronoxyl (933)+TX, butoxy(polypropylene glycol) (936)+TX, dibutyl adipate (IUPAC name) (1046)+TX, dibutyl phthalate (1047)+TX, dibutyl succinate (IUPAC name) (1048)+TX, diethyltoluamide [CCN]+TX, dimethyl carbate [CCN]+TX, dimethyl phthalate [CCN]+TX, ethyl hexanediol (1137)+TX, hexamide [CCN]+TX, methoquin-butyl (1276)+TX, methylneodecanamide [CCN]+TX, oxamate [CCN] and picaridin [CCN]+TX, an insecticide selected from the group of substances consisting of 1-dichloro-1-nitroethane (IUPAC/Chemical Abstracts name) (1058)+TX, 1,1-dichloro-2,2-bis(4-ethylphenyl)ethane (IUPAC name) (1056), +TX, 1,2-dichloropropane (IUPAC/Chemical Abstracts name) (1062)+TX, 1,2-dichloropropane with 1,3-dichloropropene (IUPAC name) (1063)+TX, 1-bromo-2-chloroethane (IUPAC/Chemical Abstracts name) (916)+TX, 2,2,2-trichloro-1-(3,4-dichlorophenyl)ethyl acetate (IUPAC name) (1451)+TX, 2,2-dichlorovinyl 2-ethylsulfinylethyl methyl phosphate (IUPAC name) (1066)+TX, 2-(1,3-dithiolan-2-yl)phenyl dimethylcarbamate (IUPAC/Chemical Abstracts name) (1109)+TX, 2-(2-butoxyethoxy)ethyl thiocyanate (IUPAC/Chemical Abstracts name) (935)+TX, 2-(4,5-dimethyl-1,3-dioxolan-2-yl)phenyl methylcarbamate (IUPAC/Chemical Abstracts name) (1084)+TX, 2-(4-chloro-3,5-xylyloxy) ethanol (IUPAC name) (986)+TX, 2-chlorovinyl diethyl phosphate (IUPAC name) (984)+TX, 2-imidazolidone (IUPAC name) (1225)+TX, 2-isovalerylindan-1,3-dione (IUPAC name) (1246)+TX, 2-methyl(prop-2-ynyl)aminophenyl methylcarbamate (IUPAC name) (1284)+TX, 2-thiocyanatoethyl laurate (IUPAC name) (1433)+TX, 3-bromo-1-chloroprop-1-ene (IUPAC name) (917)+TX, 3-methyl-1-phenylpyrazol-5-yl dimethylcarbamate (IUPAC name) (1283)+TX, 4-methyl(prop-2-ynyl)amino-3,5-xylyl methylcarbamate (IUPAC name) (1285)+TX, 5,5-dimethyl-3-oxocyclohex-1-enyl dimethylcarbamate (IUPAC name) (1085)+TX, abamectin (1)+TX, acephate (2)+TX, acetamiprid (4)+TX, acethion (alternative name) [CCN]+TX, acetoprole [CCN]+TX, acrinathrin (9)+TX, acrylonitrile (IUPAC name) (861)+TX, alanycarb (15)+TX, aldicarb (16)+TX, aldoxycarb (863)+TX, aldrin (864)+TX, allethrin (17)+TX, allosamidin (alternative name) [CCN]+TX, allyxycarb (866)+TX, alpha-cypermethrin (202)+TX, alpha-ecdysone (alternative name) [CCN]+TX, aluminium phosphide (640)+TX, amidithion (870)+TX, amidothioate (872)+TX, aminocarb (873)+TX, amiton (875)+TX, amiton hydrogen oxalate (875)+TX, amitraz (24)+TX, anabasine (877)+TX, athidathion (883)+TX, AVI 382 (compound code)+TX, AZ 60541 (compound code)+TX, azadirachtin (alternative name) (41)+TX, azamethiphos (42)+TX, azinphos-ethyl (44)+TX, azinphos-methyl (45)+TX, azothoate (889)+TX, *Bacillus thuringiensis* delta endotoxins (alternative name) (52)+TX, barium hexafluorosilicate (alternative name) [CCN]+TX, barium polysulfide (IUPAC/Chemical Abstracts name) (892)+TX, barthrin [CCN]+TX, Bayer 22/190 (development code) (893)+TX, Bayer 22408 (development code) (894)+TX, bendiocarb (58)+TX, benfuracarb (60)+TX, bensultap (66)+TX, beta-cyfluthrin (194)+TX, beta-cypermethrin (203)+TX, bifenthrin (76)+TX, bioallethrin (78)+TX, bioallethrin S-cyclopentenyl isomer (alternative name) (79)+TX, bioethanomethrin [CCN]+TX, biopermethrin (908)+TX, bioresmethrin (80)+TX, bis(2-chloroethyl) ether (IUPAC name) (909)+TX, bistrifluron (83)+TX, borax (86)+TX, brofenvalerate (alternative name)+TX, bromfenvinfos (914)+TX, bromocyclen (918)+ TX, bromo-DDT (alternative name) [CCN]+TX, bromophos (920)+TX, bromophos-ethyl (921)+TX, bufencarb (924)+ TX, buprofezin (99)+TX, butacarb (926)+TX, butathiofos (927)+TX, butocarboxim (103)+TX, butonate (932)+TX, butoxycarboxim (104)+TX, butylpyridaben (alternative name)+TX, cadusafos (109)+TX, calcium arsenate [CCN]+ TX, calcium cyanide (444)+TX, calcium polysulfide (IUPAC name) (111)+TX, camphechlor (941)+TX, carbanolate (943)+TX, carbaryl (115)+TX, carbofuran (118)+TX, carbon disulfide (IUPAC/Chemical Abstracts name) (945)+TX, carbon tetrachloride (IUPAC name) (946)+TX, carbophenothion (947)+TX, carbosulfan (119)+TX, cartap (123)+TX, cartap hydrochloride (123)+TX, cevadine (alternative name) (725)+TX, chlorbicyclen (960)+TX, chlordane (128)+TX, chlordecone (963)+TX, chlordimeform (964)+TX, chlordimeform hydrochloride (964)+TX, chlorethoxyfos (129)+ TX, chlorfenapyr (130)+TX, chlorfenvinphos (131)+TX, chlorfluazuron (132)+TX, chlormephos (136)+TX, chloroform [CCN]+TX, chloropicrin (141)+TX, chlorphoxim (989)+TX, chlorprazophos (990)+TX, chlorpyrifos (145)+ TX, chlorpyrifos-methyl (146)+TX, chlorthiophos (994)+ TX, chromafenozide (150)+TX, cinerin I (696)+TX, cinerin II (696)+TX, cinerins (696)+TX, cis-resmethrin (alternative name)+TX, cismethrin (80)+TX, clocythrin (alternative name)+TX, cloethocarb (999)+TX, closantel (alternative name) [CCN]+TX, clothianidin (165)+TX, copper acetoarsenite [CCN]+TX, copper arsenate [CCN]+TX, copper oleate [CCN]+TX, coumaphos (174)+TX, coumithoate (1006)+ TX, crotamiton (alternative name) [CCN]+TX, crotoxyphos (1010)+TX, crufomate (1011)+TX, cryolite (alternative name) (177)+TX, CS 708 (development code) (1012)+TX, cyanofenphos (1019)+TX, cyanophos (184)+TX, cyanthoate (1020)+TX, cyclethrin [CCN]+TX, cycloprothrin (188)+TX, cyfluthrin (193)+TX, cyhalothrin (196)+TX, cypermethrin (201)+TX, cyphenothrin (206)+TX, cyromazine (209)+TX, cythioate (alternative name) [CCN]+TX, d-limonene (alternative name) [CCN]+TX, d-tetramethrin (alternative name) (788)+TX, DAEP (1031)+TX, dazomet (216)+TX, DDT (219)+TX, decarbofuran (1034)+TX, deltamethrin (223)+TX, demephion (1037)+TX, demephion-O (1037)+TX, demephion-S (1037)+TX, demeton (1038)+TX, demeton-methyl (224)+TX, demeton-O (1038)+TX, demeton-O-methyl (224)+TX, demeton-S (1038)+TX, demeton-S-methyl (224)+TX, demeton-S-methylsulphon (1039)+TX, diafenthiuron (226)+TX, dialifos (1042)+TX, diamidafos (1044)+TX, diazinon (227)+TX, dicapthon (1050)+TX, dichlofenthion (1051)+TX, dichlorvos (236)+TX, dicliphos (alternative name)+TX, dicresyl (alternative name) [CCN]+ TX, dicrotophos (243)+TX, dicyclanil (244)+TX, dieldrin (1070)+TX, diethyl 5-methylpyrazol-3-yl phosphate (IUPAC name) (1076)+TX, diflubenzuron (250)+TX, dilor (alternative name) [CCN]+TX, dimefluthrin [CCN]+TX, dimefox (1081)+TX, dimetan (1085)+TX, dimethoate (262)+TX, dimethrin (1083)+TX, dimethylvinphos (265)+TX, dimetilan (1086)+TX, dinex (1089)+TX, dinex-diclexine (1089)+ TX, dinoprop (1093)+TX, dinosam (1094)+TX, dinoseb (1095)+TX, dinotefuran (271)+TX, diofenolan (1099)+TX, dioxabenzofos (1100)+TX, dioxacarb (1101)+TX, dioxathion (1102)+TX, disulfoton (278)+TX, dithicrofos (1108)+ TX, DNOC (282)+TX, doramectin (alternative name) [CCN]+TX, DSP (1115)+TX, ecdysterone (alternative name) [CCN]+TX, EI 1642 (development code) (1118)+TX, emamectin (291)+TX, emamectin benzoate (291)+TX, EMPC (1120)+TX, empenthrin (292)+TX, endosulfan (294)+TX, endothion (1121)+TX, endrin (1122)+TX, EPBP (1123)+TX, EPN (297)+TX, epofenonane (1124)+TX, eprinomectin (alternative name) [CCN]+TX, esfenvalerate (302)+TX, etaphos (alternative name) [CCN]+TX, ethiofencarb (308)+TX, ethion (309)+TX, ethiprole (310)+TX, ethoate-methyl (1134)+TX, ethoprophos (312)+TX, ethyl formate (IUPAC name) [CCN]+TX, ethyl-DDD (alternative name) (1056)+TX, ethylene dibromide (316)+TX, ethylene dichloride (chemical name) (1136)+TX, ethylene oxide [CCN]+TX, etofenprox (319)+TX, etrimfos (1142)+TX, EXD (1143)+TX, famphur (323)+TX, fenamiphos (326)+TX, fenazaflor (1147)+TX, fenchlorphos (1148)+TX, fenethacarb (1149)+TX, fenfluthrin (1150)+TX, fenitrothion (335)+TX, fenobucarb (336)+TX, fenoxacrim (1153)+TX, fenoxycarb (340)+TX, fenpirithrin (1155)+TX, fenpropathrin (342)+TX, fenpyrad (alternative name)+TX, fensulfothion (1158)+TX, fenthion (346)+TX, fenthion-ethyl [CCN]+TX, fenvalerate (349)+TX, fipronil (354)+TX, flonicamid (358)+TX, flubendiamide (CAS. Reg. No.: 272451-65-7)+TX, flucofuron (1168)+TX, flucycloxuron (366)+TX, flucythrinate (367)+TX, fluenetil (1169)+TX, flufenerim [CCN]+TX, flufenoxuron (370)+TX, flufenprox (1171)+TX, flumethrin (372)+TX, fluvalinate (1184)+TX, FMC 1137 (development code) (1185)+TX, fonofos (1191)+TX, formetanate (405)+TX, formetanate hydrochloride (405)+TX, formothion (1192)+TX, formparanate (1193)+TX, fosmethilan (1194)+TX, fospirate (1195)+TX, fosthiazate (408)+TX, fosthietan (1196)+TX, furathiocarb (412)+TX, furethrin (1200)+TX, gamma-cyhalothrin (197)+TX, gamma-HCH (430)+TX, guazatine (422)+TX, guazatine acetates (422)+TX, GY-81 (development code) (423)+TX, halfenprox (424)+TX, halofenozide (425)+TX, HCH (430)+TX, HEOD (1070)+TX, heptachlor (1211)+TX, heptenophos (432)+TX, heterophos [CCN]+TX, hexaflumuron (439)+TX, HHDN (864)+TX, hydramethylnon (443)+TX, hydrogen cyanide (444)+TX, hydroprene (445)+TX, hyquincarb (1223)+TX, imidacloprid (458)+TX, imiprothrin (460)+TX, indoxacarb (465)+TX, iodomethane (IUPAC name) (542)+TX, IPSP (1229)+TX, isazofos (1231)+TX, isobenzan (1232)+TX, isocarbophos (alternative name) (473)+TX, isodrin (1235)+TX, isofenphos (1236)+TX, isolane (1237)+TX, isoprocarb (472)+TX, isopropyl O-(methoxy-aminothiophosphoryl)salicylate (IUPAC name) (473)+TX, isoprothiolane (474)+TX, isothioate (1244)+TX, isoxathion (480)+TX, ivermectin (alternative name) [CCN]+TX, jasmolin I (696)+TX, jasmolin II (696)+TX, jodfenphos (1248)+TX, juvenile hormone I (alternative name) [CCN]+TX, juvenile hormone II (alternative name) [CCN]+TX, juvenile hormone III (alternative name) [CCN]+TX, kelevan (1249)+TX, kinoprene (484)+TX, lambda-cyhalothrin (198)+TX, lead arsenate [CCN]+TX, lepimectin (CCN)+TX, leptophos (1250)+TX, lindane (430)+TX, lirimfos (1251)+TX, lufenuron (490)+TX, lythidathion (1253)+TX, m-cumenyl methylcarbamate (IUPAC name) (1014)+TX, magnesium phosphide (IUPAC name) (640)+TX, malathion (492)+TX, malonoben (1254)+TX, mazidox (1255)+TX, mecarbam (502)+TX, mecarphon (1258)+TX, menazon (1260)+TX, mephosfolan (1261)+TX, mercurous chloride (513)+TX, mesulfenfos (1263)+TX, metaflumizone (CCN)+TX, metam (519)+TX, metam-potassium (alternative name) (519)+TX, metam-sodium (519)+TX, methacrifos (1266)+TX, methamidophos (527)+TX, methanesulfonyl fluoride (IUPAC/Chemical Abstracts name) (1268)+TX, methidathion (529)+TX, methiocarb (530)+TX, methocrotophos (1273)+TX, methomyl (531)+TX, methoprene (532)+TX, methoquin-butyl (1276)+TX, methothrin (alternative name) (533)+TX, methoxychlor (534)+TX, methoxyfenozide (535)+TX, methyl bromide (537)+TX, methyl isothiocyanate (543)+TX, methylchloroform (alternative name) [CCN]+TX, methylene chloride [CCN]+TX, metofluthrin [CCN]+TX, metolcarb (550)+TX, metoxadiazone (1288)+TX, mevinphos (556)+TX, mexacarbate (1290)+TX, milbemectin (557)+TX, milbemycin oxime (alternative name) [CCN]+TX, mipafox (1293)+TX, mirex (1294)+TX, monocrotophos (561)+TX, morphothion (1300)+TX, moxidectin (alternative name) [CCN]+TX, naftalofos (alternative name) [CCN]+TX, naled (567)+TX, naphthalene (IUPAC/Chemical Abstracts name) (1303)+TX, NC-170 (development code) (1306)+TX, NC-184 (compound code)+TX, nicotine (578)+TX, nicotine sulfate (578)+TX, nifluridide (1309)+TX, nitenpyram (579)+TX, nithiazine (1311)+TX, nitrilacarb (1313)+TX, nitrilacarb 1:1 zinc chloride complex (1313)+TX, NNI-0101 (compound code)+TX, NNI-0250 (compound code)+TX, nornicotine (traditional name) (1319)+TX, novaluron (585)+TX, noviflumuron (586)+TX, O-5-dichloro-4-iodophenyl O-ethyl ethylphosphonothioate (IUPAC name) (1057)+TX, O,O-diethyl O-4-methyl-2-oxo-2H-chromen-7-yl phosphorothioate (IUPAC name) (1074)+TX, O,O-diethyl O-6-methyl-2-propylpyrimidin-4-yl phosphorothioate (IUPAC name) (1075)+TX, O,O,O',O'-tetrapropyl dithiopyrophosphate (IUPAC name) (1424)+TX, oleic acid (IUPAC name) (593)+TX, omethoate (594)+TX, oxamyl (602)+TX, oxydemetonmethyl (609)+TX, oxydeprofos (1324)+TX, oxydisulfoton (1325)+TX, pp'-DDT (219)+TX, para-dichlorobenzene [CCN]+TX, parathion (615)+TX, parathion-methyl (616)+TX, penfluron (alternative name) [CCN]+TX, pentachlorophenol (623)+TX, pentachlorophenyl laurate (IUPAC name) (623)+TX, permethrin (626)+TX, petroleum oils (alternative name) (628)+TX, PH 60-38 (development code) (1328)+TX, phenkapton (1330)+TX, phenothrin (630)+TX, phenthoate (631)+TX, phorate (636)+TX, phosalone (637)+TX, phosfolan (1338)+TX, phosmet (638)+TX, phosnichlor (1339)+TX, phosphamidon (639)+TX, phosphine (IUPAC name) (640)+TX, phoxim (642)+TX, phoxim-methyl (1340)+TX, pirimetaphos (1344)+TX, pirimicarb (651)+TX, pirimiphos-ethyl (1345)+TX, pirimiphos-methyl (652)+TX, polychlorodicyclopentadiene isomers (IUPAC name) (1346)+TX, polychloroterpenes (traditional name) (1347)+TX, potassium arsenite [CCN]+TX, potassium thiocyanate [CCN]+TX, prallethrin (655)+TX, precocene I (alternative name) [CCN]+TX, precocene II (alternative name) [CCN]+TX, precocene III (alternative name) [CCN]+TX, primidophos (1349)+TX, profenofos (662)+TX, profluthrin [CCN]+TX, promacyl (1354)+TX, promecarb (1355)+TX, propaphos (1356)+TX, propetamphos (673)+TX, propoxur (678)+TX, prothidathion (1360)+TX, prothiofos (686)+TX, prothoate (1362)+TX, protrifenbute [CCN]+TX, pymetrozine (688)+TX, pyraclofos (689)+TX, pyrazophos (693)+TX, pyresmethrin (1367)+TX, pyrethrin I (696)+TX, pyrethrin II (696)+TX, pyrethrins (696)+TX, pyridaben (699)+TX, pyridalyl (700)+TX, pyridaphenthion (701)+TX, pyrimidifen (706)+TX, pyrimitate (1370)+TX, pyriproxyfen (708)+TX, quassia (alternative name) [CCN]+TX, quinalphos (711)+TX, quinalphos-methyl (1376)+TX, quinothion (1380)+TX, quintiofos (1381)+TX, R-1492 (development code) (1382)+TX, rafoxanide (alternative name) [CCN]+TX, resmethrin (719)+TX, rotenone (722)+TX, RU 15525 (development code) (723)+TX, RU 25475 (development code) (1386)+TX, ryania (alternative name) (1387)+TX, ryanodine (traditional name) (1387)+TX, sabadilla (alternative name) (725)+TX, schradan (1389)+TX, sebufos (alternative name)+TX, selamectin (alternative name) [CCN]+TX, SI-0009 (compound code)+TX, SI-0205 (compound code)+TX, SI-0404 (compound code)+TX, SI-0405 (compound code)+TX, silafluofen (728)+TX, SN 72129 (development code) (1397)+TX, sodium arsenite [CCN]+TX, sodium cyanide (444)+TX, sodium fluoride (IUPAC/Chemical Abstracts name) (1399)+TX, sodium hexafluorosilicate (1400)+TX, sodium pentachlorophenoxide (623)+TX, sodium selenate (IUPAC name) (1401)+TX, sodium thiocyanate [CCN]+TX, sophamide (1402)+TX, spinosad (737)+TX, spiromesifen (739)+TX, spirotetrmat (CCN)+TX, sulcofuron (746)+TX, sulcofuron-sodium (746)+TX, sulfluramid (750)+TX, sulfotep (753)+TX, sulfuryl fluoride (756)+TX, sulprofos (1408)+TX, tar oils (alternative name) (758)+TX, tau-fluvalinate (398)+TX, tazimcarb (1412)+TX, TDE (1414)+TX, tebufenozide (762)+TX, tebufenpyrad (763)+TX, tebupirimfos (764)+TX, teflubenzuron (768)+TX, tefluthrin (769)+TX, temephos (770)+TX, TEPP (1417)+TX, terallethrin (1418)+TX, terbam (alternative name)+TX, terbufos (773)+TX, tetrachloroethane [CCN]+TX, tetrachlorvinphos (777)+TX, tetramethrin (787)+TX, theta-cypermethrin (204)+TX, thiacloprid (791)+TX, thiafenox (alternative name)+TX, thiamethoxam (792)+TX, thicrofos (1428)+TX, thiocarboxime (1431)+TX, thiocyclam (798)+TX, thiocyclam hydrogen oxalate (798)+TX, thiodicarb (799)+TX, thiofanox (800)+TX, thiometon (801)+TX, thionazin (1434)+TX, thiosultap (803)+TX, thiosultap-sodium (803)+TX, thuringiensin (alternative name) [CCN]+TX, tolfenpyrad (809)+TX, tralomethrin (812)+TX, transfluthrin (813)+TX, transpermethrin (1440)+TX, triamiphos (1441)+TX, triazamate (818)+TX, triazophos (820)+TX, triazuron (alternative name)+TX, trichlorfon (824)+TX, trichlormetaphos-3 (alternative name) [CCN]+TX, trichloronat (1452)+TX, trifenofos (1455)+TX, triflumuron (835)+TX, trimethacarb (840)+TX, triprene (1459)+TX, vamidothion (847)+TX, vaniliprole [CCN]+TX, veratridine (alternative name) (725)+TX, veratrine (alternative name) (725)+TX, XMC (853)+TX, xylylcarb (854)+TX, YI-5302 (compound code)+TX, zeta-cypermethrin (205)+TX, zetamethrin (alternative name)+TX, zinc phosphide (640)+TX, zolaprofos (1469) and ZXI 8901 (development code) (858)+TX, cyantraniliprole [736994-63-19+TX, chlorantraniliprole [500008-45-7]+TX, cyenopyrafen [560121-52-0]+TX, cyflumetofen [400882-07-7]+TX, pyrifluquinazon [337458-27-2]+TX, spinetoram [187166-40-1+187166-15-0]+TX, spirotetramat [203313-25-1]+TX, sulfoxaflor [946578-00-3]+TX, flufiprole [704886-18-0]+TX, meperfluthrin [915288-13-0]+TX, tetramethylfluthrin [84937-88-2]+TX, triflumezopyrim (disclosed in WO 2012/092115)+TX, fluxametamide (WO 2007/026965)+TX, epsilon-metofluthrin [240494-71-7]+TX, epsilon-momfluorothrin [1065124-65-3]+TX, fluazaindolizine [1254304-22-7]+TX, chloroprallethrin [399572-87-3]+TX, fluxametamide [928783-29-3]+TX, cyhalodiamide [1262605-53-7]+TX, tioxazafen [330459-31-9]+TX, broflanilide [1207727-04-5]+TX, flufiprole [704886-18-0]+TX, cyclaniliprole [1031756-98-5]+TX, tetraniliprole [1229654-66-3]+TX, guadipyr (described in WO2010/060231)+TX, cycloxaprid (described in WO2005/077934)+TX, a molluscicide selected from the group of substances consisting of bis(tributyltin) oxide (IUPAC name) (913)+TX, bromoacetamide [CCN]+TX, calcium arsenate [CCN]+TX, cloethocarb (999)+TX, copper acetoarsenite [CCN]+TX, copper sulfate (172)+TX, fentin (347)+TX, ferric phosphate (IUPAC name) (352)+TX, metaldehyde (518)+TX, methiocarb (530)+TX, niclosamide (576)+TX, niclosamide-olamine (576)+TX, pentachlorophenol (623)+TX, sodium pentachlorophenoxide (623)+TX, tazimcarb (1412)+TX, thiodicarb (799)+TX, tributyltin oxide (913)+TX, trifenmorph (1454)+TX, trimethacarb (840)+TX, triphenyltin acetate (IUPAC name) (347) and triphenyltin hydroxide (IUPAC name) (347)+TX, pyriprole [394730-71-3]+TX, a nematicide selected from the group of substances consisting of AKD-3088 (compound code)+TX, 1,2-dibromo-3-chloropropane (IUPAC/Chemical Abstracts name) (1045)+TX, 1,2-dichloropropane (IUPAC/Chemical Abstracts name) (1062)+TX, 1,2-dichloropropane with 1,3-dichloropropene (IUPAC name) (1063)+TX, 1,3-dichloropropene (233)+TX, 3,4-dichlorotetrahydrothiophene 1,1-dioxide (IUPAC/Chemical Abstracts name) (1065)+TX, 3-(4-chlorophenyl)-5-methylrhodanine (IUPAC name) (980)+TX, 5-methyl-6-thioxo-1,3,5-thiadiazinan-3-ylacetic acid (IUPAC name) (1286)+TX, 6-isopentenylaminopurine (alternative name) (210)+TX, abamectin (1)+TX, acetoprole [CCN]+TX, alanycarb (15)+TX, aldicarb (16)+TX, aldoxycarb (863)+TX, AZ 60541 (compound code)+TX, benclothiaz [CCN]+TX, benomyl (62)+TX, butylpyridaben (alternative name)+TX, cadusafos (109)+TX, carbofuran (118)+TX, carbon disulfide (945)+TX, carbosulfan (119)+TX, chloropicrin (141)+TX, chlorpyrifos (145)+TX, cloethocarb (999)+TX, cytokinins (alternative name) (210)+TX, dazomet (216)+TX, DBCP (1045)+TX, DCIP (218)+TX, diamidafos (1044)+TX, dichlofenthion (1051)+TX, dicliphos (alternative name)+TX, dimethoate (262)+TX, doramectin (alternative name) [CCN]+TX, emamectin (291)+TX, emamectin benzoate (291)+TX, eprinomectin (alternative name) [CCN]+TX, ethoprophos (312)+TX, ethylene dibromide (316)+TX, fenamiphos (326)+TX, fenpyrad (alternative name)+TX, fensulfothion (1158)+TX, fosthiazate (408)+TX, fosthietan (1196)+TX, furfural (alternative name) [CCN]+TX, GY-81 (development code) (423)+TX, heterophos [CCN]+TX, iodomethane (IUPAC name) (542)+TX, isamidofos (1230)+TX, isazofos (1231)+TX, ivermectin (alternative name) [CCN]+TX, kinetin (alternative name) (210)+TX, mecarphon (1258)+TX, metam (519)+TX, metam-potassium (alternative name) (519)+TX, metam-sodium (519)+TX, methyl bromide (537)+TX, methyl isothiocyanate (543)+TX, milbemycin oxime (alternative name) [CCN]+TX, moxidectin (alternative name) [CCN]+TX, *Myrothecium verrucaria* composition (alternative name) (565)+TX, NC-184 (compound code)+TX, oxamyl (602)+TX, phorate (636)+TX, phosphamidon (639)+TX, phosphocarb [CCN]+TX, sebufos (alternative name)+TX, selamectin (alternative name) [CCN]+TX, spinosad (737)+TX, terbam (alternative name)+TX, terbufos (773)+TX, tetrachlorothiophene (IUPAC/Chemical Abstracts name) (1422)+TX, thiafenox (alternative name)+TX, thionazin (1434)+TX, triazophos (820)+TX, triazuron (alternative name)+TX, xylenols [CCN]+TX, YI-5302 (compound code) and zeatin (alternative name) (210)+TX, fluensulfone [318290-98-1]+TX, a nitrification inhibitor selected from the group of substances consisting of potassium ethylxanthate [CCN] and nitrapyrin (580)+TX, a plant activator selected from the group of substances consisting of acibenzolar (6)+TX, acibenzolar-S-methyl (6)+TX, probenazole (658) and *Reynoutria sachalinensis* extract (alternative name) (720)+TX, a rodenticide selected from the group of substances consisting of 2-isovalerylindan-1,3-dione (IUPAC name) (1246)+TX, 4-(quinoxalin-2-ylamino)benzenesulfonamide (IUPAC name) (748)+TX, alpha-chlorohydrin [CCN]+TX, aluminium phosphide (640)+TX, antu (880)+TX, arsenous oxide (882)+TX, barium carbonate (891)+TX, bisthiosemi (912)+TX, brodifacoum (89)+TX, bromadiolone (91)+TX, bromethalin (92)+TX, calcium cyanide (444)+TX, chloralose (127)+TX, chlorophacinone (140)+TX, cholecalciferol (alternative name) (850)+TX, coumachlor (1004)+TX, coumafuryl (1005)+TX, coumatetralyl (175)+TX, crimidine (1009)+TX, difenacoum (246)+TX, difethialone (249)+TX, diphacinone (273)+TX, ergocalciferol (301)+TX, flocoumafen (357)+TX, fluoroacetamide (379)+TX, flupropadine (1183)+TX, flupropadine hydrochloride (1183)+TX, gamma-HCH (430)+TX, HCH (430)+TX, hydrogen cyanide (444)+TX, iodomethane (IUPAC name) (542)+TX, lindane (430)+TX, magnesium phosphide (IUPAC name) (640)+TX, methyl bromide (537)+TX, norbormide (1318)+TX, phosacetim (1336)+TX, phosphine (IUPAC name) (640)+TX, phosphorus [CCN]+TX, pindone (1341)+TX, potassium arsenite [CCN]+TX, pyrinuron (1371)+TX, scilliroside (1390)+TX, sodium arsenite [CCN]+TX, sodium cyanide (444)+TX, sodium fluoroacetate (735)+TX, strychnine (745)+TX, thallium sulfate [CCN]+TX, warfarin (851) and zinc phosphide (640)+TX,
a synergist selected from the group of substances consisting of 2-(2-butoxyethoxy)ethyl piperonylate (IUPAC name) (934)+TX, 5-(1,3-benzodioxol-5-yl)-3-hexylcyclohex-2-enone (IUPAC name) (903)+TX, farnesol with nerolidol (alternative name) (324)+TX, MB-599 (development code) (498)+TX, MGK 264 (development code) (296)+TX, piperonyl butoxide (649)+TX, piprotal (1343)+TX, propyl isomer (1358)+TX, S421 (development code) (724)+TX, sesamex (1393)+TX, sesasmolin (1394) and sulfoxide (1406)+TX,
an animal repellent selected from the group of substances consisting of anthraquinone (32)+TX, chloralose (127)+TX, copper naphthenate [CCN]+TX, copper oxychloride (171)+TX, diazinon (227)+TX, dicyclopentadiene (chemical name) (1069)+TX, guazatine (422)+TX, guazatine acetates (422)+TX, methiocarb (530)+TX, pyridin-4-amine (IUPAC name) (23)+TX, thiram (804)+TX, trimethacarb (840)+TX, zinc naphthenate [CCN] and ziram (856)+TX,
a virucide selected from the group of substances consisting of imanin (alternative name) [CCN] and ribavirin (alternative name) [CCN]+TX,
a wound protectant selected from the group of substances consisting of mercuric oxide (512)+TX, octhilinone (590) and thiophanate-methyl (802)+TX,
and biologically active compounds selected from the group consisting of azaconazole (60207-31-0)+TX, bitertanol [70585-36-3]+TX, bromuconazole [116255-48-2]+TX, cyproconazole [94361-06-5]+TX, difenoconazole [119446-68-3]+TX, diniconazole [83657-24-3]+TX, epoxiconazole [106325-08-0]+TX, fenbuconazole [114369-43-6]+TX, fluquinconazole [136426-54-5]+TX, flusilazole [85509-19-9]+TX, flutriafol [76674-21-0]+TX, hexaconazole [79983-71-4]+TX, imazalil [35554-44-0]+TX, imibenconazole [86598-92-7]+TX, ipconazole [125225-28-7]+TX, metconazole [125116-23-6]+TX, myclobutanil [88671-89-0]+TX, pefurazoate [101903-30-4]+TX, penconazole [66246-88-6]+TX, prothioconazole [178928-70-6]+TX, pyrifenox [88283-41-4]+TX, prochloraz [67747-09-5]+TX, propiconazole [60207-90-1]+TX, simeconazole [149508-90-7]+TX, tebuconazole [107534-96-3]+TX, tetraconazole [112281-77-3]+TX, triadimefon [43121-43-3]+TX, triadimenol [55219-65-3]+TX, triflumizole [99387-89-0]+TX, triticonazole [131983-72-7]+TX, ancymidol [12771-68-5]+TX, fenarimol [60168-88-9]+TX, nuarimol [63284-71-9]+TX, bupirimate [41483-43-6]+TX, dimethirimol [5221-53-4]+TX, ethirimol [23947-60-6]+TX, dodemorph [1593-77-7]+TX, fenpropidine [67306-00-7]+TX, fenpropimorph [67564-91-4]+TX, spiroxamine [118134-30-8]+TX, tridemorph [81412-43-3]+TX, cyprodinil [121552-61-2]+TX, mepanipyrim [110235-47-7]+TX, pyrimethanil [53112-28-0]+TX, fenpiclonil [74738-17-3]+TX, fludioxonil [131341-86-1]+TX, benalaxyl [71626-11-4]+TX, furalaxyl [57646-30-7]+TX, metalaxyl [57837-19-1]+TX, R-metalaxyl [70630-17-0]+TX, ofurace [58810-48-3]+TX, oxadixyl [77732-09-3]+TX, benomyl [17804-35-2]+TX, carbendazim [10605-21-7]+TX, debacarb [62732-91-6]+TX, fuberidazole [3878-19-1]+TX, thiabendazole [148-79-8]+TX, chlozolinate [84332-86-5]+TX, dichlozoline [24201-58-9]+TX, iprodione [36734-19-7]+TX, myclozoline [54864-61-8]+TX, procymidone [32809-16-8]+TX, vinclozoline [50471-44-8]+TX, boscalid [188425-85-6]+TX, carboxin [5234-68-4]+TX, fenfuram [24691-80-3]+TX, flutolanil [66332-96-5]+TX, mepronil [55814-41-0]+TX, oxycarboxin [5259-88-1]+TX, penthiopyrad [183675-82-3]+TX, thifluzamide [130000-40-7]+TX, guazatine [108173-90-6]+TX, dodine [2439-10-3][112-65-2] (free base)+TX, iminoctadine [13516-27-3]+TX, azoxystrobin [131860-33-8]+TX, dimoxystrobin [149961-52-4]+TX, enestroburin {Proc. BCPC, Int. Congr., Glasgow, 2003, 1, 93}+TX, fluoxastrobin [361377-29-9]+TX, kresoxim-methyl [143390-89-0]+TX, metominostrobin [133408-50-1]+TX, trifloxystrobin [141517-21-7]+TX, orysastrobin [248593-16-0]+TX, picoxystrobin [117428-22-5]+TX, pyraclostrobin [175013-18-0]+TX, ferbam [14484-64-1]+TX, mancozeb [8018-01-7]+TX, maneb [12427-38-2]+TX, metiram [9006-42-2]+TX, propineb [12071-83-9]+TX, thiram [137-26-8]+TX, zineb [12122-67-7]+TX, ziram [137-30-4]+TX, captafol [2425-06-1]+TX, captan [133-06-2]+TX, dichlofluanid [1085-98-9]+TX, fluoroimide [41205-21-4]+TX, folpet [133-07-3]+TX, tolylfluanid [731-27-1]+TX, bordeaux mixture [8011-63-0]+TX, copperhydroxid [20427-59-2]+TX, copperoxychlorid [1332-40-7]+TX, coppersulfat [7758-98-7]+TX, copperoxid [1317-39-1]+TX, mancopper [53988-93-5]+TX, oxine-copper [10380-28-6]+TX, dinocap [131-72-6]+TX, nitrothal-isopropyl [10552-74-6]+TX, edifenphos [17109-49-8]+TX, iprobenphos [26087-47-8]+TX, isoprothiolane [50512-35-1]+TX, phosdiphen [36519-00-3]+TX, pyrazophos [13457-18-6]+TX, tolclofos-methyl [57018-04-9]+TX, acibenzo-lar-S-methyl [135158-54-2]+TX, anilazine [101-05-3]+TX, benthiavalicarb [413615-35-7]+TX, blasticidin-S [2079-00-7]+TX, chinomethionat [2439-01-2]+TX, chloroneb [2675-77-6]+TX, chlorothalonil [1897-45-6]+TX, cyflufenamid [180409-60-3]+TX, cymoxanil [57966-95-7]+TX, dichlone [117-80-6]+TX, diclocymet [139920-32-4]+TX, diclomezine [62865-36-5]+TX, dicloran [99-30-9]+TX, diethofencarb [87130-20-9]+TX, dimethomorph [110488-70-5]+TX, SYP-LI90 (Flumorph) [211867-47-9]+TX, dithianon [3347-22-6]+TX, ethaboxam [162650-77-3]+TX, etridiazole [2593-15-9]+TX, famoxadone [131807-57-3]+TX, fenamidone [161326-34-7]+TX, fenoxanil [115852-48-7]+TX, fentin [668-34-8]+TX, ferimzone [89269-64-7]+TX, fluazinam [79622-59-6]+TX, fluopicolide [239110-15-7]+TX, flusulfamide [106917-52-6]+TX, fenhexamid [126833-17-8]+TX, fosetyl-aluminium [39148-24-8]+TX, hymexazol [10004-44-1]+TX, iprovalicarb [140923-17-7]+TX, IKF-916 (Cyazofamid) [120116-88-3]+TX, kasugamycin [6980-18-3]+TX, methasulfocarb [66952-49-6]+TX, metrafenone [220899-03-6]+TX, pencycuron [66063-05-6]+TX, phthalide [27355-22-2]+TX, polyoxins [11113-80-7]+TX, probenazole [27605-76-1]+TX, propamocarb [25606-41-1]+TX, proquinazid [189278-12-4]+TX, pyroquilon [57369-32-1]+TX, quinoxyfen [124495-18-7]+TX, quintozene [82-68-8]+TX, sulfur [7704-34-9]+TX, tiadinil [223580-51-6]+TX, triazoxide [72459-58-6]+TX, tricyclazole [41814-78-2]+TX, triforine [26644-46-2]+TX, validamycin [37248-47-8]+TX, zoxamide (RH7281) [156052-68-5]+TX, mandipropamid [374726-62-2]+TX, isopyrazam [881685-58-1]+TX, sedaxane [874967-67-6]+TX, 3-difluoromethyl-1-methyl-1H-pyrazole-4-carboxylic acid (9-dichloromethylene-1,2,3,4-tetrahydro-1,4-methano-naphthalen-5-yl)-amide (disclosed in WO 2007/048556)+TX, 3-difluoromethyl-1-methyl-1H-pyrazole-4-carboxylic acid (3',4',5'-trifluoro-biphenyl-2-yl)-amide (disclosed in WO 2006/087343)+TX, [(3S,4R,4aR,6S,6aS,12R,12aS,12bS)-3-[(cyclopropylcarbonyl)oxy]-1,3,4,4a,5,6,6a,12,12a,12b-decahydro-6,12-dihydroxy-4,6a,12b-trimethyl-11-oxo-9-(3-pyridinyl)-2H,11Hnaphtho[2,1-b]pyrano[3,4-e]pyran-4-yl] methyl-cyclopropanecarboxylate [915972-17-7]+TX and 1,3,5-trimethyl-N-(2-methyl-1-oxopropyl)-N-[3-(2-methylpropyl)-4-[2,2,2-trifluoro-1-methoxy-1-(trifluoromethyl) ethyl]phenyl]-1H-pyrazole-4-carboxamide [926914-55-8]+TX.

The references in brackets behind the active ingredients, e.g. [3878-19-1] refer to the Chemical Abstracts Registry number. The above described mixing partners are known. Where the active ingredients are included in "The Pesticide Manual" [The Pesticide Manual—A World Compendium; Thirteenth Edition; Editor: C. D. S. TomLin; The British Crop Protection Council], they are described therein under the entry number given in round brackets hereinabove for the particular compound; for example, the compound "abamectin" is described under entry number (1). Where "[CCN]" is added hereinabove to the particular compound, the compound in question is included in the "Compendium of Pesticide Common Names", which is accessible on the internet [A. Wood; *Compendium of Pesticide Common Names*, Copyright © 1995-2004]; for example, the compound "acetoprole" is described under the internet address http://www.alanwood.net/pesticides/acetoprole.html.

Most of the active ingredients described above are referred to hereinabove by a so-called "common name", the relevant "ISO common name" or another "common name" being used in individual cases. If the designation is not a "common name", the nature of the designation used instead is given in round brackets for the particular compound; in that case, the IUPAC name, the IUPAC/Chemical Abstracts name, a "chemical name", a "traditional name", a "compound name" or a "development code" is used or, if neither one of those designations nor a "common name" is used, an "alternative name" is employed. "CAS Reg. No" means the Chemical Abstracts Registry Number.

The active ingredient mixture of the compounds of formula I selected from Tables 1 to 6 with active ingredients described above comprises a compound selected from Tables 1 to 6 and an active ingredient as described above preferably in a mixing ratio of from 100:1 to 1:6000, especially from 50:1 to 1:50, more especially in a ratio of from 20:1 to 1:20, even more especially from 10:1 to 1:10, very especially from 5:1 and 1:5, special preference being given to a ratio of from 2:1 to 1:2, and a ratio of from 4:1 to 2:1 being likewise preferred, above all in a ratio of 1:1, or 5:1, or 5:2, or 5:3, or 5:4, or 4:1, or 4:2, or 4:3, or 3:1, or 3:2, or 2:1, or 1:5, or 2:5, or 3:5, or 4:5, or 1:4, or 2:4, or 3:4, or 1:3, or 2:3, or 1:2, or 1:600, or 1:300, or 1:150, or 1:35, or 2:35, or 4:35, or 1:75, or 2:75, or 4:75, or 1:6000, or 1:3000, or 1:1500, or 1:350, or 2:350, or 4:350, or 1:750, or 2:750, or 4:750. Those mixing ratios are by weight.

The mixtures as described above can be used in a method for controlling pests, which comprises applying a composition comprising a mixture as described above to the pests or their environment, with the exception of a method for treatment of the human or animal body by surgery or therapy and diagnostic methods practised on the human or animal body.

The mixtures comprising a compound of formula I selected from Tables 1 to 6 and one or more active ingredients as described above can be applied, for example, in a single "ready-mix" form, in a combined spray mixture composed from separate formulations of the single active ingredient components, such as a "tank-mix", and in a combined use of the single active ingredients when applied in a sequential manner, i.e. one after the other with a reasonably short period, such as a few hours or days. The order of applying the compounds of formula I selected from Tables 1 to 6 and the active ingredients as described above is not essential for working the present invention.

The compositions according to the invention can also comprise further solid or liquid auxiliaries, such as stabilizers, for example unepoxidized or epoxidized vegetable oils (for example epoxidized coconut oil, rapeseed oil or soya oil), antifoams, for example silicone oil, preservatives, viscosity regulators, binders and/or tackifiers, fertilizers or other active ingredients for achieving specific effects, for example bactericides, fungicides, nematocides, plant activators, molluscicides or herbicides.

The compositions according to the invention are prepared in a manner known per se, in the absence of auxiliaries for example by grinding, screening and/or compressing a solid active ingredient and in the presence of at least one auxiliary for example by intimately mixing and/or grinding the active ingredient with the auxiliary (auxiliaries). These processes for the preparation of the compositions and the use of the compounds I for the preparation of these compositions are also a subject of the invention.

The application methods for the compositions, that is the methods of controlling pests of the abovementioned type, such as spraying, atomizing, dusting, brushing on, dressing, scattering or pouring—which are to be selected to suit the intended aims of the prevailing circumstances—and the use of the compositions for controlling pests of the abovementioned type are other subjects of the invention. Typical rates of concentration are between 0.1 and 1000 ppm, preferably between 0.1 and 500 ppm, of active ingredient. The rate of application per hectare is generally 1 to 2000 g of active ingredient per hectare, in particular 10 to 1000 g/ha, preferably 10 to 600 g/ha.

A preferred method of application in the field of crop protection is application to the foliage of the plants (foliar application), it being possible to select frequency and rate of application to match the danger of infestation with the pest in question. Alternatively, the active ingredient can reach the plants via the root system (systemic action), by drenching the locus of the plants with a liquid composition or by incorporating the active ingredient in solid form into the locus of the plants, for example into the soil, for example in the form of granules (soil application). In the case of paddy rice crops, such granules can be metered into the flooded paddy-field.

The compounds of the invention and compositions thereof are also be suitable for the protection of plant propagation material, for example seeds, such as fruit, tubers or kernels, or nursery plants, against pests of the abovementioned type. The propagation material can be treated with the compound prior to planting, for example seed can be treated prior to sowing. Alternatively, the compound can be applied to seed kernels (coating), either by soaking the kernels in a liquid composition or by applying a layer of a solid composition. It is also possible to apply the compositions when the propagation material is planted to the site of application, for example into the seed furrow during drilling. These treatment methods for plant propagation material and the plant propagation material thus treated are further subjects of the invention. Typical treatment rates would depend on the plant and pest/fungi to be controlled and are generally between 1 to 200 grams per 100 kg of seeds, preferably between 5 to 150 grams per 100 kg of seeds, such as between 10 to 100 grams per 100 kg of seeds.

The term seed embraces seeds and plant propagules of all kinds including but not limited to true seeds, seed pieces, suckers, corns, bulbs, fruit, tubers, grains, rhizomes, cuttings, cut shoots and the like and means in a preferred embodiment true seeds.

The present invention also comprises seeds coated or treated with or containing a compound of formula I. The term "coated or treated with and/or containing" generally signifies that the active ingredient is for the most part on the surface of the seed at the time of application, although a greater or lesser part of the ingredient may penetrate into the seed material, depending on the method of application. When the said seed product is (re)planted, it may absorb the active ingredient. In an embodiment, the present invention makes available a plant propagation material adhered thereto with a compound of formula (I). Further, it is hereby made available, a composition comprising a plant propagation material treated with a compound of formula (I).

Seed treatment comprises all suitable seed treatment techniques known in the art, such as seed dressing, seed coating, seed dusting, seed soaking and seed pelleting. The seed treatment application of the compound formula (I) can be carried out by any known methods, such as spraying or by dusting the seeds before sowing or during the sowing/planting of the seeds.

BIOLOGICAL EXAMPLES

Example B1: Activity Against *Spodoptera littoralis* (Egyptian Cotton Leaf Worm)

(Larvicide, Feeding/Residual Contact Activity, Preventive)

Cotton leaf discs were placed on agar in a 24-well microtiter plate and sprayed with test solutions. After drying, the leaf discs were infested with five L1 larvae. The samples were checked for mortality, repellent effect, feeding behaviour, and growth regulation 3 days after treatment (DAT). Control of *Spodoptera littoralis* by a test sample is when at least one of mortality, anti-feedant effect, and growth inhibition is higher than an untreated sample.

In this test, compounds P1, P2, P3, P4, P5, P6, P7, P8, P9, P10, P11, P12, P13, P14, P15, P17, P18, P22, P23, P24, P25, P28, P29, P30, P33, P35, P38, P39, P40, P41, P43, P44, P45, P47, P48, P49, P50, P51, P52, P53 and P54 gave an effect of at least 80% in at least one of the three categories (mortality, anti-feedancy, or growth inhibition) at a concentration of 400 ppm.

Example B2: Activity Against *Spodoptera littoralis* (Egyptian Cotton Leaf Worm)

(Systemic Activity)

Test compounds were applied by pipette into 24 well plates and mixed with agar. Lettuce seeds were placed on the agar and the multi well plate is closed by another plate which contains also agar. After 7 days the roots have absorbed the compound and the lettuce has grown into the lid plate. The lettuce leaves were now cut off into the lid plate. *Spodoptera* eggs were pipetted through a plastic stencil on a humid gel blotting paper and the plate closed with it. The samples are checked for mortality, repellent effect, feeding behavior, and growth regulation 5 days after infestation.

In this test, compound P2, P3, P4, P9, P10, P12 and P15 gave an effect of at least 80% in at least one of the three categories (mortality, anti-feedancy, or growth inhibition) at a concentration of 12.5 ppm.

Example B3: Activity Against *Plutella xylostella* (Diamond Back Moth)

(Larvicide, Feeding/Residual Contact Activity, Preventive)

24-well microtiter plate (MTP) with artificial diet was treated with test solutions by pipetting. After drying, the MTPs were infested with L2 larvae (10-15 per well). After an incubation period of 5 days, samples were checked for larval mortality, antifeedant and growth regulation.

In this test, compound P2, P4, P6, P9, P10, P11, P12, P15, P17, P18, P23, P24, P25, P28, P29, P33, P35, P38, P39, P40, P43, P44, P45, P48, P49, P50, P51, P52, P53 and P54 showed an activity of over 80% at a concentration of 400 ppm.

Example B4: Activity Against *Diabrotica balteata* (Corn Root Worm)

(Larvae L2 on Maize Sprouts, Feeding/Contact, Preventative)

Maize sprouts, placed on an agar layer in 24 well micro titer plates were treated with test solutions by spraying. After drying, the MTPs were infested with L2 larvae (6-10 per well). After an incubation period of 5 days, samples were checked for larval mortality and growth regulation.

In this test, compounds P1, P2, P3, P4, P6, P7, P9, P10, P11, P12, P15, P16, P17, P18, P20, P22, P23, P24, P25, P26, P28, P29, P30, P32, P33, P34, P35, P36, P38, P39, P40, P41, P43, P44, P45, P47, P48, P49, P50, P51, P52, P53 and P54 showed an activity of over 80% at a concentration of 400 ppm.

Example B5: Activity Against *Myzus persicae* (Green Peach Aphid)

(Feeding/Residual Contact Activity, Preventive), Mixed Population

Sunflower leaf discs were placed on agar in a 24-well microtiter plate and sprayed with test solutions. After drying, the leaf discs were infested with an aphid population of mixed ages. After an incubation period of 6 DAT, samples were checked for mortality and special effects (e.g. phytotoxicity).

In this test, compounds P1, P2, P3, P4, P5, P6, P8, P9, P10, P11, P14 and P15 showed an activity of over 80% at a concentration of 400 ppm.

Example B6: Activity Against *Myzus persicae* (Green Peach Aphid)

(Feeding Activity Sachet Test), Mixed Population

Test compounds were applied by pipette into 24 well plates and mixed with Sucrose solution. The plates were closed with a stretched Parafilm. A plastic stencil with 24 holes is placed onto the plate and infested pea seedlings were placed directly on the Parafilm. The infested plate is closed with a gel blotting paper and another plastic stencil and then turned upside down. 5 days after infestation the samples were checked on mortality. Application rate: 12.5 ppm.

In this test, compounds P1, P2, P23, P25, P38, P39, P40, P41, P43, P45, P50 and P54 showed an activity of at least 80% at a concentration of 12.5 ppm.

Example B7: Activity Against *Bemisia tabaci* (Cotton White Fly)

(Adulticide Contact Activity, Preventative), Adult

Cotton leaf discs were placed on agar in a 24-well microtiter plate and sprayed with test solutions. After drying, the leaf discs were infested with adult white flies. After an incubation period of 7 DAT, samples were checked for mortality and special effects (e.g. phytotoxicity).

In this test, compounds P2, P4, P6, P9, P10 and P15 showed an activity of over 80% at a concentration of 400 ppm.

Example B8: Activity Against *Euschistus heros* (Neotropical Brown Stink Bug)

Soybean leaf on agar in 24-well microtiter plates were sprayed with aqueous test solutions prepared from 10,000 ppm DMSO stock solutions. After drying the leaf were infested with N-2 nymphs. The samples were assessed for mortality 5 days after infestation.

In this test, compounds P2, P4, P8, P15, P25, P29, P35, P38 and P40 showed an activity of over 80% at a concentration of 400 ppm.

Example B9: Activity Against *Myzus persicae* (Green Peach Aphid)

(Systemic/Feeding Activity, Curative), Mixed Population

Roots of pea seedlings, infested with an aphid population of mixed ages, were placed directly in the test solutions. 6 days after introduction, samples were checked for mortality and special effects on the plant.

In this test, compounds P4, P39, P50 and P54 showed an activity of at least 80% at a concentration of 24 ppm.

Example B10: Activity Against *Tetranychus urticae* (Two-Spotted Spider Mite)

Bean leaf discs on agar in 24-well microtiter plates were sprayed with aqueous test solutions prepared from 10'000 ppm DMSO stock solutions. After drying the leaf discs were infested with a mite population of mixed ages. The samples were assessed for mortality on mixed population (mobile stages) 8 days after infestation.

The following compounds resulted in at least 80% mortality at an application rate of 400 ppm: P3.

Example B11: Activity Against *Aedes aegypti* (Yellow Fever Mosquito)

Test solutions, at an application rate of 200 ppm in ethanol, were applied to 12-well tissue culture plates. Once the deposits were dry, five, two to five days old adult female *Aedes aegypti* were added to each well, and sustained with a 10% sucrose solution in a cotton wool plug. Assessment of knockdown was made one hour after introduction, and mortality was assessed at 24 and 48 hours after introduction.

The following compounds gave at least 80% control of *Aedes aegypti* after 48 h: P3, P4 and P9.

The invention claimed is:

1. A compound of formula I,

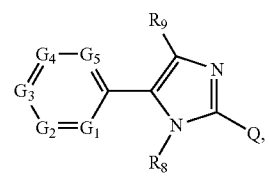

(I)

wherein
$G_1$ is nitrogen or $CR_2$;
$G_2$ is nitrogen or $CR_3$;
$G_3$ is nitrogen or $CR_4$;
$G_4$ is nitrogen or $CR_5$;
$G_5$ is nitrogen or $CR_6$, with the proviso that not more than 2 nitrogens as G may follow consecutively;
$R_2$, $R_3$, $R_4$, $R_5$ and $R_6$ are, independently from each other, hydrogen, halogen, $C_1$-$C_4$haloalkyl, $C_1$-$C_4$haloalkyl substituted by one or two hydroxy, $C_1$-$C_4$haloalkyl substituted by one or two methoxy, $C_1$-$C_4$haloalkyl substituted by one or two cyano, $C_1$-$C_4$haloalkylthio, $C_1$-$C_4$haloalkylsulfinyl, $C_1$-$C_4$haloalkylsulfonyl, O($C_1$-$C_4$haloalkyl), $SF_5$, phenylcarbonylthio, cyano, mercapto, $C_1$-$C_4$alkoxycarbonyl, $C_1$-$C_4$alkylcarbonyl or —C(O)$C_1$-$C_4$haloalkyl; or
two adjacent $R_i$, wherein $R_i$ is selected from $R_2$, $R_3$, $R_4$, $R_5$ and $R_6$, taken together form a fragment —OCH$_2$O— or —OCF$_2$O—;
Q is a radical selected from the group consisting of formula $Q_1$ and $Q_2$

Q₁

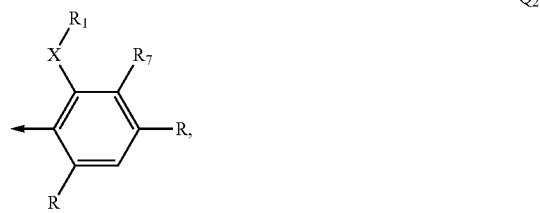

Q₂ wherein the arrow denotes the point of attachment to the imidazole ring;
X is S, SO or $SO_2$;
each R is, independently from each other, hydrogen, halogen, $C_1$-$C_4$haloalkoxy or $C_1$-$C_4$haloalkyl;
each $R_1$ is, independently from each other, $C_1$-$C_4$alkyl, $C_1$-$C_4$haloalkyl, $C_3$-$C_6$cycloalkyl, $C_3$-$C_6$cycloalkyl-$C_1$-$C_4$alkyl, $C_3$-$C_6$halocycloalkyl, $C_2$-$C_6$alkenyl, $C_2$-$C_6$haloalkenyl or $C_2$-$C_6$alkynyl;
each $R_7$ is, independently from each other, hydrogen or halogen;
$R_8$ is hydrogen, $C_1$-$C_4$alkyl or $C_1$-$C_4$haloalkyl; and
$R_9$ is hydrogen, $C_1$-$C_4$alkyl, $C_1$-$C_4$haloalkyl or halogen;
or an agrochemically acceptable salt, stereoisomer, enantiomer, tautomer or N-oxide thereof; with the exception of the compound 4-methyl-2-(2-methylthiophenyl)-5-(3-pyridyl)imidazole.

2. A compound of formula I according to claim 1, represented by the compounds of formula I-1, (I-1)

wherein
G$_1$, G$_2$, G$_3$, G$_4$, and G$_5$ are as defined under formula I in claim 1;
X$_1$ is S, SO or SO$_2$;
Ra$_1$ is hydrogen, halogen or C$_1$-C$_4$haloalkyl;
R$_{11}$ is methyl, ethyl, n-propyl, i-propyl or cyclopropylmethyl;
R$_8$ is as defined under formula I in claim 1; and
R$_9$ is as defined above under formula I in claim 1;
or an agrochemically acceptable salt, stereoisomer, enantiomer, tautomer or N-oxide thereof.

3. A compound of formula I-1 according to claim 2, wherein G$_1$ is CH; G$_2$ is CH; G$_3$ is C(CF$_3$), C(OCF$_3$), C(CN), C(C(O)CH$_3$), C(SCF$_3$), C(SO$_2$CF$_3$) or C(halogen); G$_4$ is CH; and G5 is CH.

4. A compound of formula I-1 according to claim 2, wherein G$_1$ is CH; G$_2$ is C(CF$_3$), C(OCF$_3$), C(CN), C(C(O)CH$_3$), C(SCF$_3$), C(SO$_2$CF$_3$) or C(halogen); G$_3$ is CH; G$_4$ is CH; and G$_5$ is CH.

5. A compound of formula I according to claim 1, represented by the compounds of formula I-2, (I-2)

wherein
G$_1$, G$_2$, G$_3$, G$_4$, and G$_5$ are as defined under formula I in claim 1;
X$_2$ is S, SO or SO$_2$;
Ra$_2$ is hydrogen, halogen or C$_1$-C$_4$haloalkyl;
R$_{12}$ is methyl, ethyl, n-propyl, i-propyl or cyclopropylmethyl;
R$_8$ is as defined under formula I in claim 1; and
R$_9$ is as defined above under formula I in claim 1;
or an agrochemically acceptable salt, stereoisomer, enantiomer, tautomer or N-oxide thereof.

6. A compound of formula I-2 according to claim 5, wherein G$_1$ is CH; G$_2$ is CH; G$_3$ is C(CF$_3$), C(OCF$_3$), C(CN), C(C(O)CH$_3$), C(SCF$_3$), C(SO$_2$CF$_3$) or C(halogen); G$_4$ is CH; and G5 is CH.

7. A compound of formula 1-2 according to claim 5, wherein G$_1$ is CH; G$_2$ is C(CF$_3$), C(OCF$_3$), C(CN), C(C(O)CH$_3$), C(SCF$_3$), C(SO$_2$CF$_3$) or C(halogen); G$_3$ is CH; G$_4$ is CH; and G$_5$ is CH.

8. A compound of formula I according to claim 1, represented by the compounds of formula I-3, (I-3)

wherein
A is N or CH;
R$_{10}$ is phenyl mono- or polysubstituted by substituents independently selected from the group consisting of halogen, cyano, C$_1$-C$_4$haloalkoxy, C$_1$-C$_4$haloalkyl and C$_1$-C$_4$alkylcarbonyl; or
R$_{10}$ is phenyl monosubstituted by substituents independently selected from the group consisting of C$_1$-C$_4$haloalkylsulfanyl, C$_1$-C$_4$haloalkylsulfinyl and C$_1$-C$_4$haloalkylsulfonyl; or
R$_{10}$ is phenyl substituted by a fragment —OCF$_2$O— on two adjacent positions; or
R$_{10}$ is pyridyl mono- or polysubstituted by substituents independently selected from the group consisting of halogen, cyano, C$_1$-C$_4$haloalkoxy, C$_1$-C$_4$haloalkyl and C$_1$-C$_4$alkylcarbonyl; or
R$_{10}$ is pyridyl monosubstituted by substituents independently selected from the group consisting of C$_1$-C$_4$haloalkylsulfanyl, C$_1$-C$_4$haloalkylsulfinyl and C$_1$-C$_4$haloalkylsulfonyl; or
R$_{10}$ is pyridyl substituted by a fragment —OCF$_2$O— on two adjacent positions;
X$_3$ is S, SO or SO$_2$;
Ra$_3$ is hydrogen or C$_1$-C$_4$haloalkyl;
R$_{13}$ is C$_1$-C$_4$alkyl;
R$_8$ is hydrogen or C$_1$-C$_4$alkyl; and
R$_9$ is hydrogen, C$_1$-C$_4$alkyl or halogen.

9. A compound of formula I according to claim 1, represented by the compounds of formula I-4, (I-4)

wherein A is N or CH;
R$_{10'}$ is a diazine radical selected from the group consisting of formula DA1 to DA5,

DA1

-continued

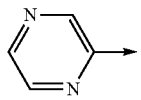
DA2

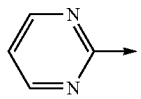
DA3

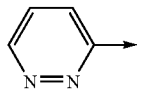
DA4

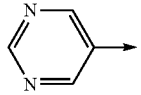
DA5 wherein the arrow denotes the point of attachment to the triazole ring; and said group $R_{10'}$ may be mono- or polysubstituted by substituents independently selected from the group consisting of halogen, cyano, $C_1$-$C_4$haloalkoxy and $C_1$-$C_4$haloalkyl;

$X_4$ is S, SO or $SO_2$;

$Ra_4$ is hydrogen or $C_1$-$C_4$haloalkyl;

$R_{14}$ is $C_1$-$C_4$alkyl;

$R_8$ is hydrogen or $C_1$-$C_4$alkyl; and $R_9$ is hydrogen, $C_1$-$C_4$alkyl or halogen.

10. A pesticidal composition, which comprises at least one compound of formula I according to claim 1 as active ingredient and at least one auxiliary.

11. A method for controlling pests, which comprises applying a composition according to claim 10 to the pests or their environment with the exception of a method for treatment of the human or animal body by surgery or therapy and diagnostic methods practiced on the human or animal body.

12. A method for the protection of plant propagation material from the attack by pests, which comprises treating the propagation material or the site where the propagation material is planted with a composition according to claim 10.

13. Plant propagation material treated with a composition according to claim 10.

14. A compound of formula (IIIa),

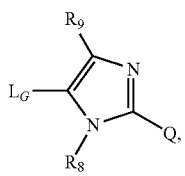
(IIIa)

wherein

Q is a radical selected from the group consisting of formula $Q_1$ and $Q_2$,

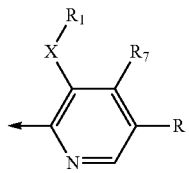
$Q_1$

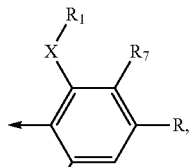
$Q_2$ wherein the arrow denotes the point of attachment to the imidazole ring;

X is S, SO or $SO_2$;

each R is, independently from each other, hydrogen, halogen, $C_1$-$C_4$haloalkoxy or $C_1$-$C_4$haloalkyl;

$R_1$ is $C_1$-$C_4$alkyl, $C_1$-$C_4$haloalkyl, $C_3$-$C_6$cycloalkyl, $C_3$-$C_6$cycloalkyl-$C_1$-$C_4$alkyl, $C_3$-$C_6$halocycloalkyl, $C_2$-$C_6$alkenyl, $C_2$-$C_6$haloalkenyl or $C_2$-$C_6$alkynyl;

$R_7$ is hydrogen or halogen;

$R_8$ is hydrogen, $C_1$-$C_4$alkyl or $C_1$-$C_4$haloalkyl;

$R_9$ is hydrogen; and $L_G$ is iodine or bromine.

15. A compound of formula (IVa),

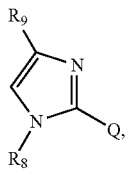
(IVa)

wherein

Q is a radical selected from the group consisting of formula $Q_1$ and $Q_2$,

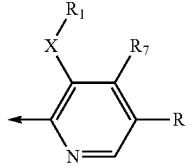
$Q_1$

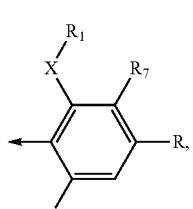
$Q_2$ wherein the arrow denotes the point of attachment to the imidazole ring;

X is S, SO or SO2;
each R is, independently from each other, hydrogen, halogen, $C_1$-$C_4$haloalkoxy or $C_1$-$C_4$haloalkyl;
$R_1$ is $C_1$-$C_4$alkyl, $C_1$-$C_4$haloalkyl, $C_3$-$C_6$cycloalkyl, $C_3$-$C_6$cycloalkyl-$C_1$-$C_4$alkyl, $C_3$-$C_6$halocycloalkyl, $C_2$-$C_6$alkenyl, $C_2$-$C_6$haloalkenyl or $C_2$-$C_6$alkynyl;
$R_7$ is hydrogen or halogen;
$R_8$ is hydrogen, $C_1$-$C_4$alkyl or $C_1$-$C_4$haloalkyl; and
$R_9$ is hydrogen;
with the exception of 2-[2-(methylthio)phenyl]-1H-imidazole hydrochloride.

* * * * *